(12) United States Patent
Meuleman et al.

(10) Patent No.: US 10,378,051 B2
(45) Date of Patent: Aug. 13, 2019

(54) CONTINUOUS EXTENSION AND DEBLOCKING IN REACTIONS FOR NUCLEIC ACIDS SYNTHESIS AND SEQUENCING

(71) Applicant: ILLUMINA CAMBRIDGE LIMITED, Nr Saffron Walden (GB)

(72) Inventors: Wouter Meuleman, Nr Saffron Walden (GB); Elena Cressina, Nr Saffron Walden (GB); Geoffrey Paul Smith, Nr Saffron Walden (GB); Rosamond Jackson, Nr Saffron Walden (GB); Xiaohai Liu, Nr Saffron Walden (GB)

(73) Assignee: Illumina Cambridge Limited, Nr Saffron Walden (GB)

( * ) Notice: Subject to any disclaimer, the term of this patent is extended or adjusted under 35 U.S.C. 154(b) by 1219 days.

(21) Appl. No.: 13/627,134

(22) Filed: Sep. 26, 2012

(65) Prior Publication Data
US 2013/0085073 A1    Apr. 4, 2013

Related U.S. Application Data

(60) Provisional application No. 61/540,714, filed on Sep. 29, 2011.

(51) Int. Cl.
*C40B 20/00* (2006.01)
*C12Q 1/68* (2018.01)
*C12Q 1/6874* (2018.01)

(52) U.S. Cl.
CPC ................................ *C12Q 1/6874* (2013.01)

(58) Field of Classification Search
None
See application file for complete search history.

(56) References Cited

U.S. PATENT DOCUMENTS

| | | | |
|---|---|---|---|
| 5,629,177 A | 5/1997 | Hyman | |
| 5,641,658 A | 6/1997 | Adams et al. | |
| 6,090,592 A | 7/2000 | Adams et al. | |
| 6,172,218 B1 | 1/2001 | Brenner | |
| 6,232,465 B1 | 5/2001 | Hiatt et al. | |
| 6,306,597 B1 | 10/2001 | Macevicz | |
| 6,664,079 B2 | 12/2003 | Ju et al. | |
| 6,969,488 B2 | 11/2005 | Bridgham et al. | |
| 7,057,026 B2 | 6/2006 | Barnes et al. | |
| 7,329,860 B2 | 2/2008 | Feng et al. | |
| 7,414,116 B2 | 8/2008 | Milton et al. | |
| 7,427,673 B2 | 9/2008 | Balasubramanian et al. | |
| 7,541,444 B2 | 6/2009 | Milton et al. | |
| 2002/0051994 A1* | 5/2002 | Kwiatkowski et al. | 435/6 |
| 2002/0182686 A1 | 12/2002 | Yang | |
| 2005/0042648 A1 | 2/2005 | Griffiths et al. | |
| 2005/0079510 A1 | 4/2005 | Berka et al. | |
| 2005/0130173 A1 | 6/2005 | Leamon et al. | |
| 2005/0244870 A1 | 11/2005 | Chee et al. | |
| 2006/0240439 A1 | 10/2006 | Smith et al. | |
| 2007/0099208 A1 | 5/2007 | Drmanac et al. | |
| 2007/0128624 A1 | 6/2007 | Gormley et al. | |
| 2007/0219367 A1 | 9/2007 | Shchepinov et al. | |
| 2007/0254885 A1* | 11/2007 | Perry | 514/248 |
| 2008/0037008 A1 | 2/2008 | Shepard et al. | |
| 2008/0293071 A1* | 11/2008 | Gelfand et al. | 435/6 |
| 2009/0026082 A1 | 1/2009 | Rothberg et al. | |
| 2009/0127589 A1 | 5/2009 | Rothberg et al. | |
| 2010/0041053 A1* | 2/2010 | Fiss et al. | 435/6 |
| 2010/0092957 A1* | 4/2010 | Zhao et al. | 435/6 |
| 2010/0093068 A1 | 4/2010 | Williams | |
| 2010/0111768 A1 | 5/2010 | Banerjee et al. | |
| 2010/0137143 A1 | 6/2010 | Rothberg et al. | |
| 2010/0282617 A1 | 11/2010 | Rothberg et al. | |
| 2011/0059865 A1 | 3/2011 | Smith et al. | |
| 2011/0300534 A1 | 12/2011 | Chiou et al. | |

FOREIGN PATENT DOCUMENTS

| | | |
|---|---|---|
| EP | 1 689 881 | 5/2005 |
| WO | WO 91/06678 | 5/1991 |
| WO | WO 98/59066 | 12/1998 |

(Continued)

OTHER PUBLICATIONS

Jones et al. Mutagenesis vol. 25 No. 1 pp. 3-16, 2010.*
Fuller, Carl et al., "The challenges of sequencing by synthesis," Nature Biotechnology, 27(11), 2009, 1013-1023.
Guo, J. et al., "Four-color DNA sequencing with 3'-O-modified nucleotide reversible terminators and chemically cleavable fluorescent dideoxynucleotides," PNAS, 105(27), 2008, 9145-9150.
Metzker, et al., "Electrophoretically uniform fluorescent dyes for automated DNA sequencing," Science, 271 (5254), 1996, 1420-1422.

(Continued)

*Primary Examiner* — Tracy Vivlemore
*Assistant Examiner* — Sahana S Kaup
(74) *Attorney, Agent, or Firm* — Knobbe, Martens, Olson & Bear, LLP

(57) ABSTRACT

A reaction mixture including (a) a nucleic acid having a primer hybridized to a template, (b) nucleotide analogs, wherein the nucleotide analogs have a blocking moiety; (c) a polymerase that is capable of forming an extended primer by adding the nucleotide analogs to the primer, and (d) a deblocking agent that is capable of removing the blocking moiety from the extended primer. Also provided is a method of synthesizing a polynucleotide including sequentially adding a plurality of the different nucleotides analogs to the nucleic acid via several reaction cycles in the reaction mixture, wherein each reaction cycle includes (i) the polymerase adding a nucleotide analog to the nucleic acid to form a transient nucleic acid species comprising a blocking moiety, and (ii) the deblocking agent modifying the transient nucleic acid species to remove the blocking moiety.

38 Claims, 24 Drawing Sheets

Specification includes a Sequence Listing.

(56) References Cited

FOREIGN PATENT DOCUMENTS

| WO | 2004/018497 A2 | | 3/2004 |
|---|---|---|---|
| WO | WO 05/010145 | | 2/2005 |
| WO | WO 05/065814 | | 7/2005 |
| WO | WO 2007/010251 | | 1/2007 |
| WO | WO2007075967 | * | 7/2007 |
| WO | WO 2007/123744 | | 11/2007 |
| WO | WO2008042067 | * | 10/2008 |
| WO | WO2010017932 | * | 2/2010 |
| WO | WO 2011/159942 | | 12/2011 |

OTHER PUBLICATIONS

Metzker, M.L., "Sequencing technologies-the next generation," Nature Reviews Genetics, vol. 11, Dec. 8, 2009, 31-46.

Adessi et al., "Solid Phase DNA amplification: Characterisation of primer attachment and amplification mechanisms", Nucleic Acids Research 28, 2000, 1-8.

Bentley et al., "Accurate whole human genome sequencing using reversible terminator chemistry", Nature, 456, 2008, 53-59.

Bordo, "Suggestions for "Safe" Residue Substitutions in Site-directed Mutagenesis", J. Mol. Biol. 217, 1991, 721-729.

Canard et al., "Catalytic editing properties of DNA polymerases", Proc. Natl. Acad. Sci., vol. 92, 1995, 10859-10863.

Canard and, Sarfati, "DNA polymerase fluorescent substrates with reversible 3'-tags", Gene, vol. 148, 1994, 1-6.

Dressman et al., "Transforming single DNA molecules into fluorescent magnetic particles for detection and enumeration of genetic variations", PNAS, 100(15), 2003, 8817-8822.

Fedurco et al., "BTA, a novel reagent for DNA attachment on glass and efficient generation of solid-phase amplified DNA colonies", Nucleic Acids Res. 34(3), 2006, e22.

Giraud et al., "Fluorescence lifetime biosensing with DNA microarrays and a CMOS-SPAD imager", Biomedical Optics Express, 1(5), 2010, 1302-1308.

Hayes et al., "Combining computational and experimental screening for rapid optimization of protein properties", PNAS, 99(25), 2002, 15926-15931.

Mitra et al., "In situ localized amplification and contact replication of many individual DNA molecules", Nucleic Acids Research, vol. 27, No. 24, 1999, e34.

Mol et al., "DNA-bound structures and mutants reveal abasic DNA binding by APE1 DNA repair and coordination", Nature, 403, 2000, 451-456.

Stoppa et al., "A 32×32-Pixel Array with In-Pixel Photon Counting and Arrival Time Measurement in the Analog Domain", IEEE European Solid-State Device Conference (ESSCIRC), Athens, Greece, IEEE, 2009, 204-207.

Suh et al., "34-Phosphodiesterase activity of human apurinic/apyrimidinic endonuclease at DNA double-strand break ends", Nucleic Acids Research, 12, 1997, 2495-2500.

Turcatti, et al., "A new class of cleavable fluorescent nucleotides: synthesis and optimization as reversible terminators for DNA sequencing by synthesis", Nucleic Acids Research, vol. 36, No. 4, 2008, e25.

* cited by examiner

SEQUENCE LISTING

<160> NUMBER OF SEQ ID NOS: 1

<210> SEQ ID NO 1
<211> LENGTH: 18
<212> TYPE: DNA
<213> ORGANISM: Artificial Sequence
<220> FEATURE:
<223> OTHER INFORMATION: non-naturally occuring sequence

<400> SEQUENCE: 1
acggatttca gtacgcca                                             18

CONTINUOUS EXTENSION AND DEBLOCKING IN REACTIONS FOR NUCLEIC ACIDS SYNTHESIS AND SEQUENCING

This application claims the benefit of U.S. Provisional Application No. 61/540,714, filed Sep. 29, 2011, which is incorporated herein by reference.

BACKGROUND

This disclosure relates generally to detection and characterization of nucleic acids. More specifically this disclosure relates to determining the sequences of nucleic acids using, for example, sequencing-by-synthesis techniques.

Our genome provides a blue print for predicting many of our inherent predispositions such as our likes and dislikes, talents, susceptibility to disease and responsiveness to therapeutic drugs. The human genome contains a sequence of over 3 billion nucleotides and it is the differences in just a fraction of those nucleotides that impart many of our unique characteristics. The research community is making impressive strides in unraveling the features that make up the blue print and with that a more complete understanding of how the information in each blue print relates to human health. However, a more complete understanding of how the information in each blue print relates to the living structures they encode, will require that tens-of-thousands or millions of genomes be sequenced. Only then will scientists be able to correlate the complexities of the genetic code with the variety of human characteristics. Furthermore, beyond the research effort the costs must come down in order to usher in the day when each person will have a copy of their own personal genome so that they can sit down with their doctor to determine appropriate choices for a healthy lifestyle or a proper course of treatment.

The most prevalent method for reading the sequence of nucleotides in a genome is sequencing-by-synthesis (SBS). In a typical SBS protocol, millions of genome fragments are attached to individual locations on the surface of a chip or microscope slide. The surface-attached fragments are subjected to repeated cycles of reagent delivery and detection such that the nucleotides in each fragment are 'read' one by one. The repeated cycles amount to a synthesis process in which each fragment acts as a template for synthesis of a complementary polynucleotide, one nucleotide per cycle. Each cycle includes (1) delivering blocked, labeled nucleotides (e.g., A, T, G, C) and a polymerase under conditions where the polymerase adds a single nucleotide to the growing complementary polynucleotide; (2) washing the surface to remove excess monomeric nucleotides that did not react; (3) detecting a label that was recruited to each fragment by the addition of the respective nucleotide to the complementary polynucleotide; (4) delivering a deblocking agent that removes a blocking group that was also recruited to each fragment by the addition of the respective nucleotide to the complementary polynucleotide; and (5) washing the surface to remove the deblocking agent from the surface so that it will not interfere with the next nucleotide addition step in the next cycle. Several cycles of reagent delivery and detection can be repeated to determine the sequences of the genomic DNA fragments.

In the above SBS protocol the blocking group prevents more than one nucleotide from being added to the growing complementary polynucleotide during each cycle. The blocking group is recruited to the complementary polynucleotide when the single nucleotide is added and a subsequent nucleotide cannot be added until the deblocking agent removes it. In each cycle of the SBS protocol, the deblocking agent is introduced to the surface bound fragments after the nucleotide monomers and polymerase have been washed away and after the detection step. Furthermore, extensive washing of the surface is carried out after the deblocking step. As such, the deblocking agent(s) are not present with the reagents used for nucleotide addition. This separation of deblocking agents from extension reagents provides for the incremental control of the SBS reaction whereby only a single nucleotide is added to a complementary polynucleotide during each cycle. The incremental control in turn provides for accuracy in detecting each nucleotide addition individually and in proper order.

Sequencing-by-synthesis has been a very successful methodology, but is still relatively expensive. A variety of approaches can be taken to address this problem. For example, the efficiency of manufacturing SBS reagents can be improved. Indeed, this approach has been taken by commercial suppliers of SBS platforms and has achieved incremental improvements. Another approach is miniaturization, for example, by increasing the density of fragments on detection surfaces or reducing reagent volumes used in fluidic steps. Several techniques have been devised that remove fluidic steps. For example, SBS has been carried out using nucleotides that do not have blocking moieties, thereby avoiding the need for a separate deblocking step and deblocking agents. Other techniques have been developed that avoid the need for nucleotides having label moieties and/or optical detection. However, many of the above approaches have inherent limitations that have to date limited their effectiveness at bringing down the cost of sequencing and that may ultimately prevent them from doing so.

What is needed is a reduction in the cost of sequencing that drives large genetic correlation studies carried out by research scientists and that makes sequencing accessible in the clinical environment for the treatment of individual patients making life changing decisions. The invention set forth herein satisfies this need and provides other advantages as well.

BRIEF SUMMARY

This disclosure provides reaction mixtures. A reaction mixture can include (a) a nucleic acid having a primer hybridized to a template, (b) a nucleotide analog, wherein the nucleotide analog has a blocking moiety; (c) a polymerase that is capable of forming an extended primer by adding the nucleotide analog to the primer, and (d) a deblocking agent that is capable of removing the blocking moiety from the extended primer.

In particular embodiments, a reaction mixture can include (a) a nucleic acid having a primer hybridized to a template, (b) a collection of at least four different nucleotide analogs, wherein each of the different nucleotide analogs has a different base moiety and a blocking moiety, (c) a polymerase that is capable of forming an extended primer by adding at least one of the different nucleotide analogs to the primer, and (d) a deblocking agent that is capable of removing the blocking moiety from the extended primer.

A reaction mixture can include (a) a nucleic acid having a primer hybridized to a template, (b) a collection of at least four different nucleotide analogs, wherein each of the different nucleotide analogs has a different base moiety, a blocking moiety having a different label moiety, and a label-modifier moiety, each of the different label moieties being correlated with one of the different base moieties, (c)

a polymerase that is capable of forming an extended primer by adding at least one of the different nucleotide analogs to the primer and removing the label-modifier from the at least one of the different nucleotides that is added to the primer, and (d) a deblocking agent that is capable of removing the blocking moiety from the extended primer.

In some embodiments, a reaction mixture can includes (a) a nucleic acid having a primer hybridized to a template, (b) a nucleotide analog, wherein the nucleotide analog has a phosphotriester blocking moiety; (c) a polymerase that is capable of forming an extended primer by adding the nucleotide analog to the primer, and (d) a deblocking agent that is capable of removing the blocking moiety from the extended primer, wherein the deblocking agent includes a phosphotriesterase and a phosphodiesterase.

A reaction mixture can include (a) a nucleic acid having a primer hybridized to a template, (b) a collection of at least four different nucleotide analogs, wherein each of the different nucleotide analogs has a different base moiety and a phosphotriester blocking moiety, (c) a polymerase that is capable of forming an extended primer by adding at least one of the different nucleotide analogs to the primer, and (d) a deblocking agent that is capable of removing the phosphotriester blocking moiety from the extended primer, wherein the deblocking agent includes a phosphotriesterase and a phosphodiesterase.

Provided herein are methods of synthesizing a polynucleotide. A method can include the steps of (a) providing a mixture including a nucleic acid, a collection of different nucleotide analogs, a polymerase and a deblocking agent, and (b) allowing sequential addition of a plurality of the different nucleotides analogs to the nucleic acid to proceed via several reaction cycles in the mixture, wherein each reaction cycle includes the steps of (i) the polymerase adding a nucleotide analog to the nucleic acid to form a transient nucleic acid species comprising a blocking moiety, and (ii) the deblocking agent modifying the transient nucleic acid species to remove the blocking moiety.

A method of synthesizing a polynucleotide can include the steps of (a) providing a mixture comprising (i) a nucleic acid having a primer hybridized to a template, (ii) a collection of different nucleotide analogs, wherein each of the different nucleotide analogs has a different base moiety and a blocking moiety, (iii) a polymerase, and (iv) a deblocking agent; (b) carrying out a reaction cycle in the mixture wherein (i) the polymerase adds one of the different nucleotide analogs to the primer, thereby forming an extended primer having the blocking moiety from the one of the different nucleotide analogs, and (ii) the deblocking agent removes the blocking moiety from the extended primer; and (c) performing several repetitions of the reaction cycle in the mixture.

Further provided is a method of synthesizing a polynucleotide that includes the steps of (a) providing a mixture including a nucleic acid, a collection of different nucleotide analogs, a polymerase, a phosphotriesterase and a phosphodiesterase, wherein the different nucleotide analogs each have a phosphotriester blocking moiety, and (b) sequentially adding a plurality of the different nucleotides analogs to the nucleic acid by several reaction cycles in the mixture, wherein each reaction cycle includes: (i) the polymerase adding a nucleotide analog to the nucleic acid to form a transient nucleic acid species having a phosphotriester blocking moiety, (ii) the phosphotriesterase converting the phosphotriester blocking moiety to a phosphodiester blocking moiety, and (iii) the phosphodiesterase removing the phosphodiester blocking moiety from the nucleic acid.

A method of synthesizing a polynucleotide can include the steps of (a) providing a mixture including (i) a nucleic acid having a primer hybridized to a template, (ii) a collection of different nucleotide analogs, wherein each of the different nucleotide analogs has a different base moiety, and a phosphotriester blocking moiety, (iii) a polymerase, (iv) a phosphotriesterase, and (v) a phosphodiesterase; (b) carrying out a reaction cycle in the mixture wherein (i) the polymerase adds one of the different nucleotide analogs to the primer, thereby forming an extended primer having the phosphotriester blocking moiety from the one of the different nucleotide analogs, (ii) the phosphotriesterase converts the phosphotriester blocking moiety to a phosphodiester blocking moiety, and (iii) the phosphodiesterase removes the phosphodiester blocking moiety from the extended primer; and (c) performing several repetitions of the reaction cycle in the mixture.

Methods of sequencing a polynucleotide are also provided. The method can include the steps of (a) providing a mixture comprising (i) a nucleic acid having a primer hybridized to a template, (ii) a collection of different nucleotide analogs, wherein each of the different nucleotide analogs has a different base moiety, and a blocking moiety having a different label moiety, each of the different label moieties being correlated with one of the different base moieties, (iii) a polymerase, and (iv) a deblocking agent; (b) carrying out a reaction cycle in the mixture wherein (i) the polymerase adds one of the different nucleotide analogs to the primer, thereby forming an extended primer having the blocking moiety and the different label moiety from the one of the different nucleotide analogs, and (ii) the deblocking agent removes the blocking moiety and the different label moiety from the extended primer; (c) performing several repetitions of the reaction cycle in the mixture; (d) detecting the label moiety that is on the extended primer during the repetitions of the reaction cycle.

A method of sequencing a polynucleotide can include the steps of (a) providing a mixture comprising (i) a nucleic acid having a primer hybridized to a template, (ii) a collection of different nucleotide analogs, wherein each of the different nucleotide analogs has a different base moiety, a blocking moiety having a different label moiety, and a label-modifier moiety, each of the different label moieties being correlated with one of the different base moieties, (iii) a polymerase, and (iv) a deblocking agent; (b) carrying out a reaction cycle in the mixture wherein (i) the polymerase adds one of the different nucleotide analogs to the primer and removes the label-modifier from the one of the different nucleotide analogs, thereby forming an extended primer having the blocking moiety and the different label moiety from the one of the different nucleotide analogs, and (ii) the deblocking agent removes the blocking moiety and the different label moiety from the extended primer; (c) performing several repetitions of the reaction cycle in the mixture; (d) detecting the label moiety that is on the extended primer during the repetitions of the reaction cycle.

A method of sequencing a polynucleotide can include the steps of (a) providing a mixture including (i) a nucleic acid having a primer hybridized to a template, (ii) a collection of different nucleotide analogs, wherein each of the different nucleotide analogs has a different base moiety, and a phosphotriester blocking moiety having a different label moiety, each of the different label moieties being correlated with one of the different base moieties, (iii) a polymerase, (iv) a phosphotriesterase, and (v) a phosphodiesterase; (b) carrying out a reaction cycle in the mixture wherein (i) the polymerase adds one of the different nucleotide analogs to the primer, thereby forming an extended primer having the phosphotriester blocking moiety and the different label moiety from the one of the different nucleotide analogs, (ii) the phosphotriesterase converts the phosphotriester blocking moiety to a phosphodiester blocking moiety, and (iii) the phosphodiesterase removes the phosphodiester blocking moiety and the different label moiety from the extended primer; (c) performing several repetitions of the reaction cycle in the mixture; and (d) detecting the label moiety that is on the extended primer during the repetitions of the reaction cycle.

A method of sequencing a polynucleotide can include the steps of (a) providing a mixture including (i) a nucleic acid having a primer hybridized to a template, (ii) a collection of different nucleotide analogs, wherein each of the different nucleotide analogs has a different base moiety, a phosphotriester blocking moiety having a different label moiety, and a label-modifier moiety, each of the different label moieties being correlated with one of the different base moieties, (iii) a polymerase, (iv) a phosphotriesterase, and (v) a phosphodiesterase; (b) carrying out a reaction cycle in the mixture wherein (i) the polymerase adds one of the different nucleotide analogs to the primer and removes the label-modifier from the one of the different nucleotide analogs, thereby forming an extended primer having the phosphotriester blocking moiety and the different label moiety from the one of the different nucleotide analogs, (ii) the phosphotriesterase converts the phosphotriester blocking moiety to a phosphodiester blocking moiety, and (iii) the phosphodiesterase removes the phosphodiester blocking moiety and the different label moiety from the extended primer; (c) performing several repetitions of the reaction cycle in the mixture; and (d) detecting the label moiety that is on the extended primer during the repetitions of the reaction cycle.

The details of one or more embodiments are set forth in the accompanying drawings and the description below. Other features, objects, and advantages will be apparent from the description and drawings, and from the claims.

AcOH, H$_2$O, MeCN; c) 1) POCl$_3$, proton Sponge®, PO(OEt)$_3$; 2) P$_2$O$_7^{2-}$(Bu$_3$NH$^+$)$_2$, DMF, Bu$_3$N; 3) TEAB 1M, aq.

Figure 17:
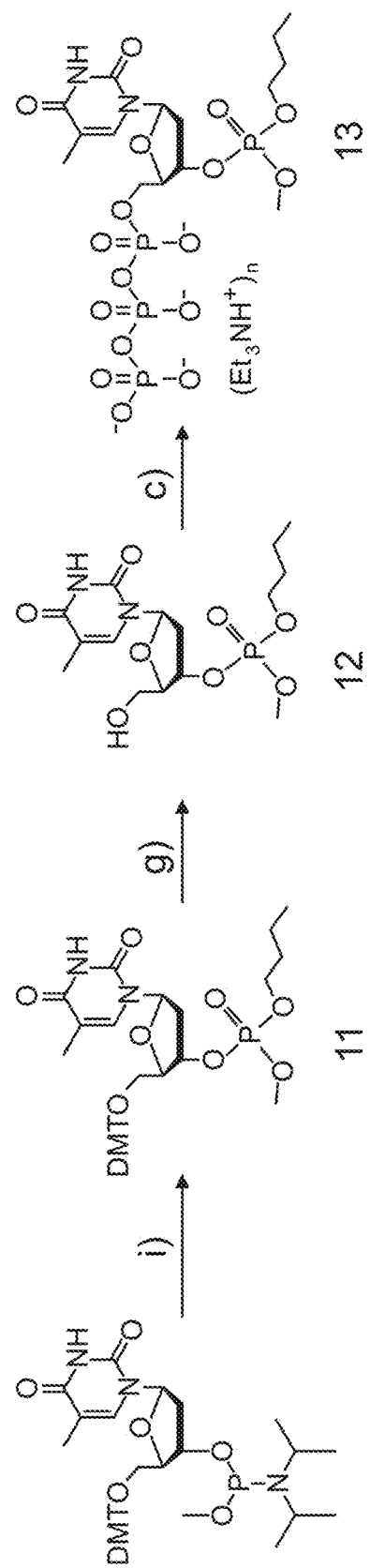

FIG. 17 shows synthesis of a nucleotide 5'-triphosphate 3'-phosphotriester (pppT-3'PO$_4$MeBu). Reagents: i) 1) ETT, n-BuOH, MeCN; 2) I$_2$, THF, Pyridine, H$_2$O; g) AcOH, H$_2$O, MeCN; c) 1) POCl$_3$, proton Sponge®, PO(OEt)$_3$); 2) P$_2$O$_7^{2-}$ (Bu$_3$NH$^+$)$_2$, DMF, Bu$_3$N; 2) TEAB 1M, aq.

Figure 18:
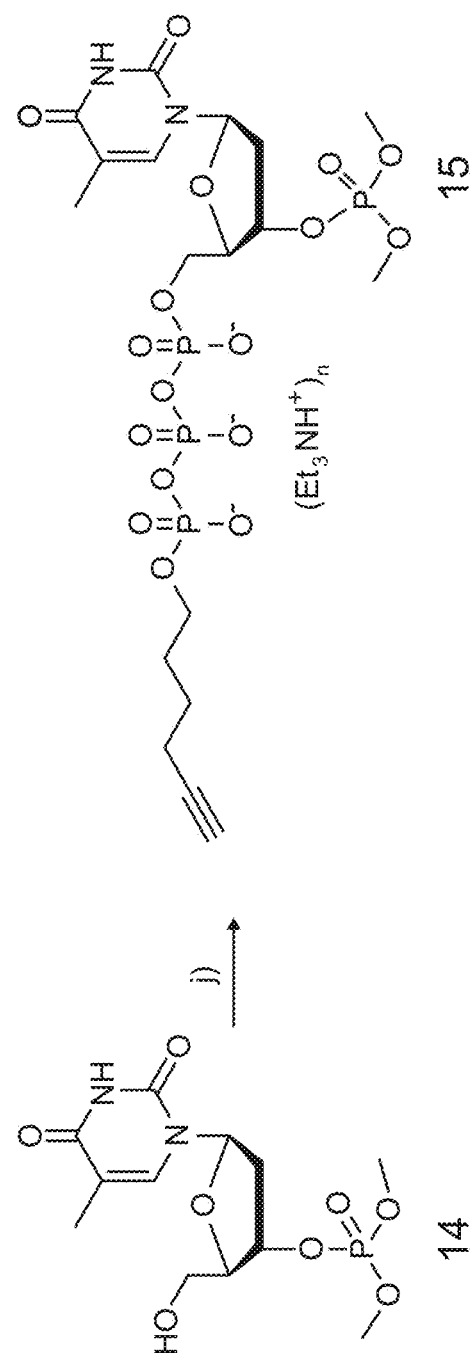

FIG. 18 shows synthesis of 5'-(γ-alkyl)triphosphate 3'-phosphotriester. Reagents: j) 1) POCl$_3$, proton Sponge®, PO(OEt)$_3$ 2) P$_2$O$_7^{2-}$(Bu$_3$NH$^+$)$_2$, DMF, Bu$_3$N 3) 5-hexyn-1-ol 4) TEAB 1M, aq.

Figure 19:
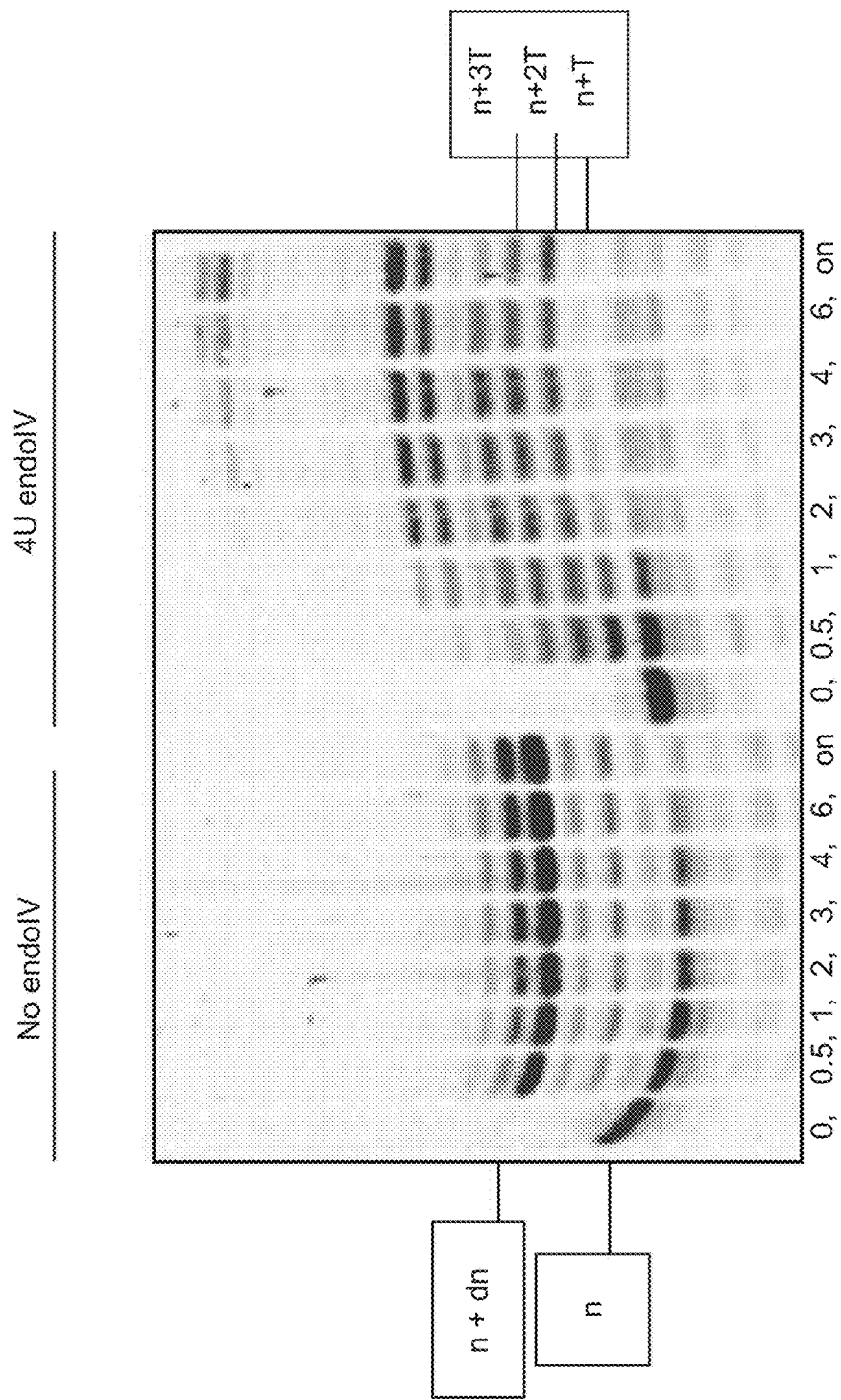

FIG. 19 shows a 12% urea sequencing gel loaded with extension reaction products in the presence and absence of endo IV.

Figure 20:
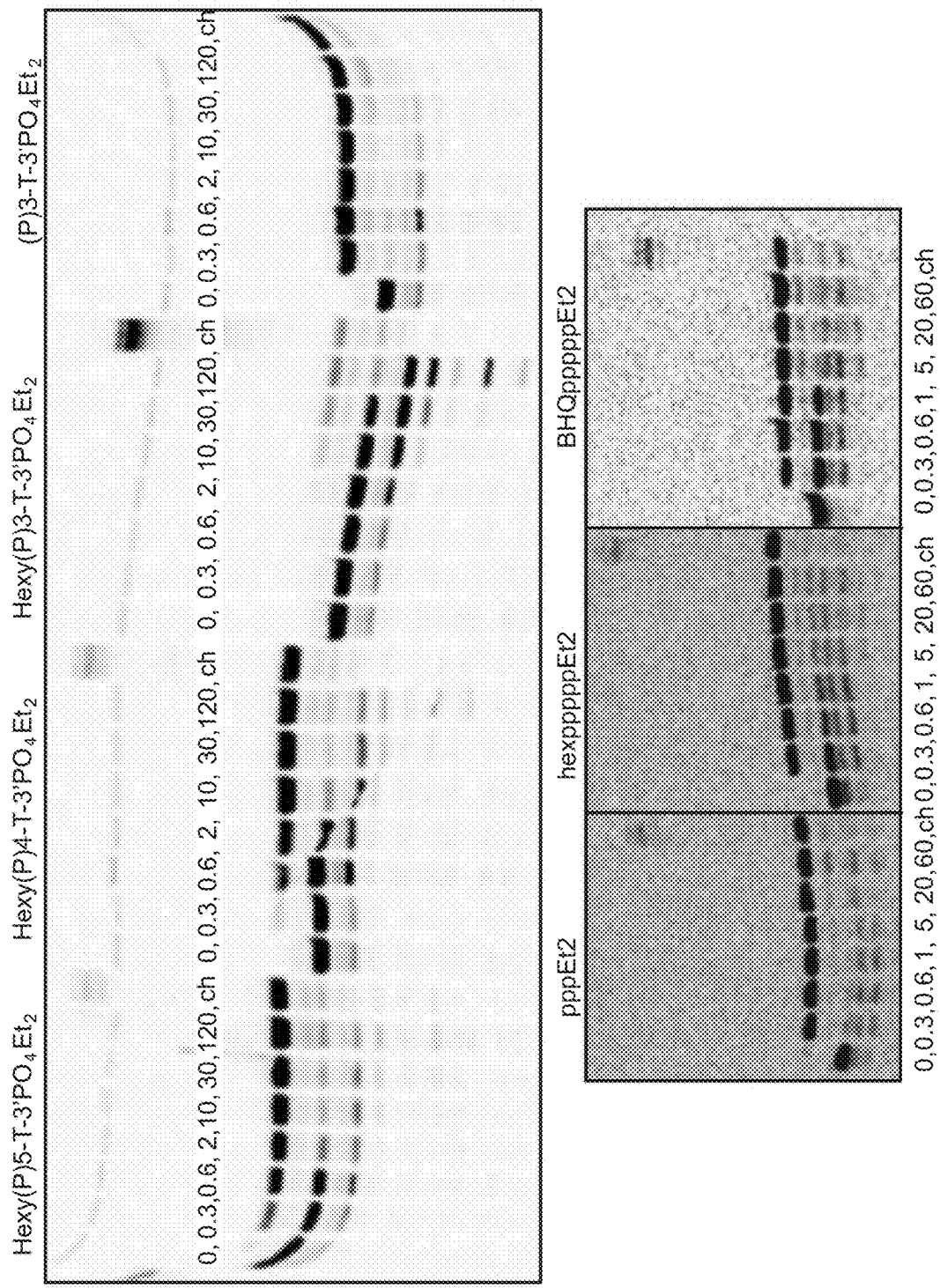

FIG. 20 shows 12% urea sequencing gels loaded with extension reaction products in the presence of nucleotides having different 5' moieties.

Figure 21:
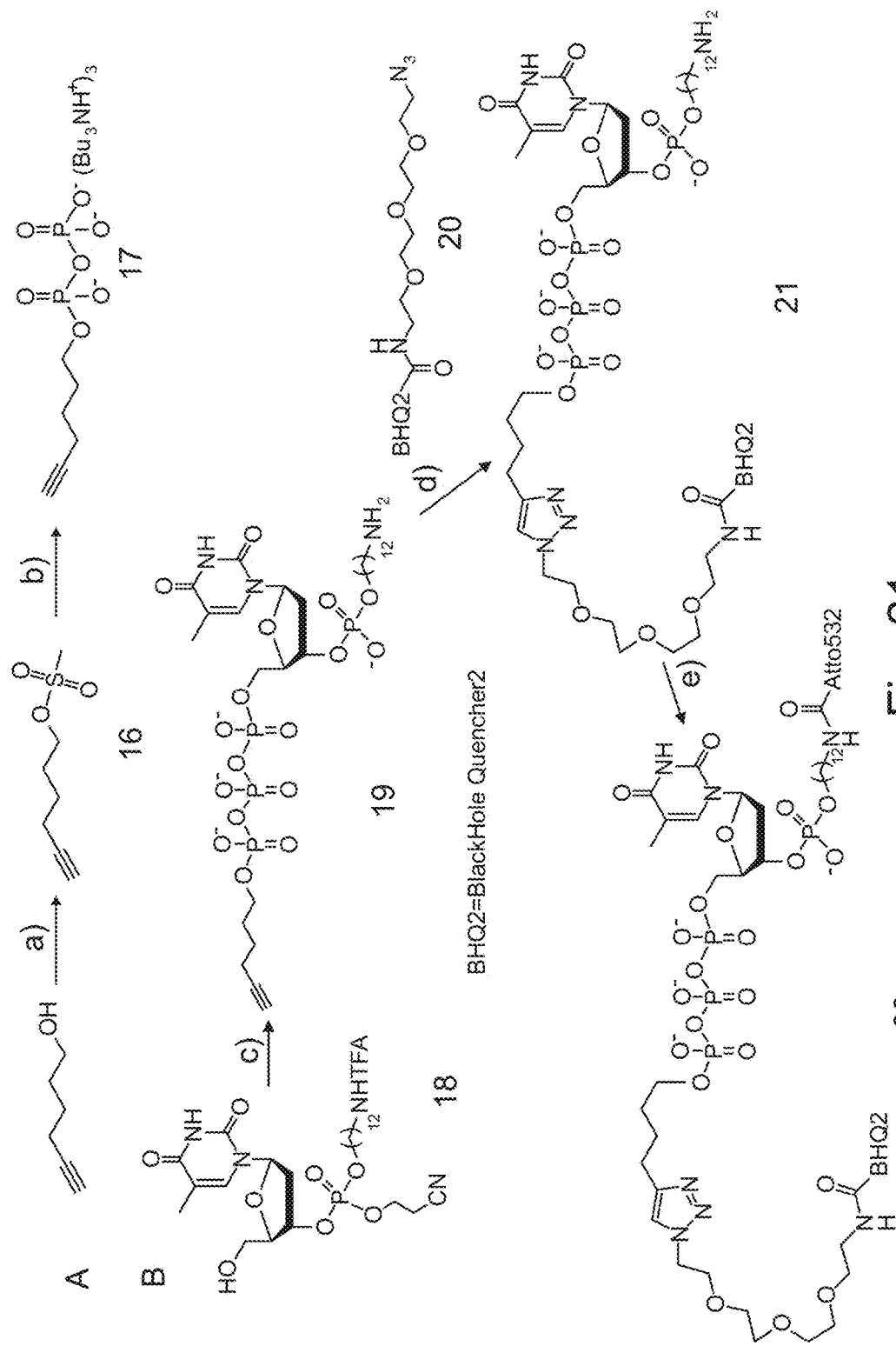

FIG. 21 shows a diagrammatic scheme for synthesis of a quencher/dye labeled nucleotide 5'-triphosphate 3'-phosphodiester. Panel A: Synthesis of 1-hex-5-ynyl pyrophosphate tris(tri-n-butylammonium) salt (17). Reagents: a) Ms-Cl, Et$_3$N, CH$_2$Cl$_2$, rt. b) 1) P$_2$O$_7$(Bu$_4$N)$_4$, MeCN; 2) Dowex WX8-200(H$^+$), Bu$_3$N. Panel B: Example of synthesis of a quencher/dye labelled nucleotide 5'-triphosphate 3'-phosphodiester. Reagents: c) 1) POCl$_3$, proton Sponge®, PO(OEt)$_3$; 2) 17, DMF, Bu$_3$N; 3) TEAB 1M, aq.; 4) NH$_3$ aq. 35%. d) 20, CuSO$_4$, TBTA, Na ascorbate, tBuOH/H$_2$O. e) Atto532-NHS ester, DIPEA, DMF.

Figure 22:
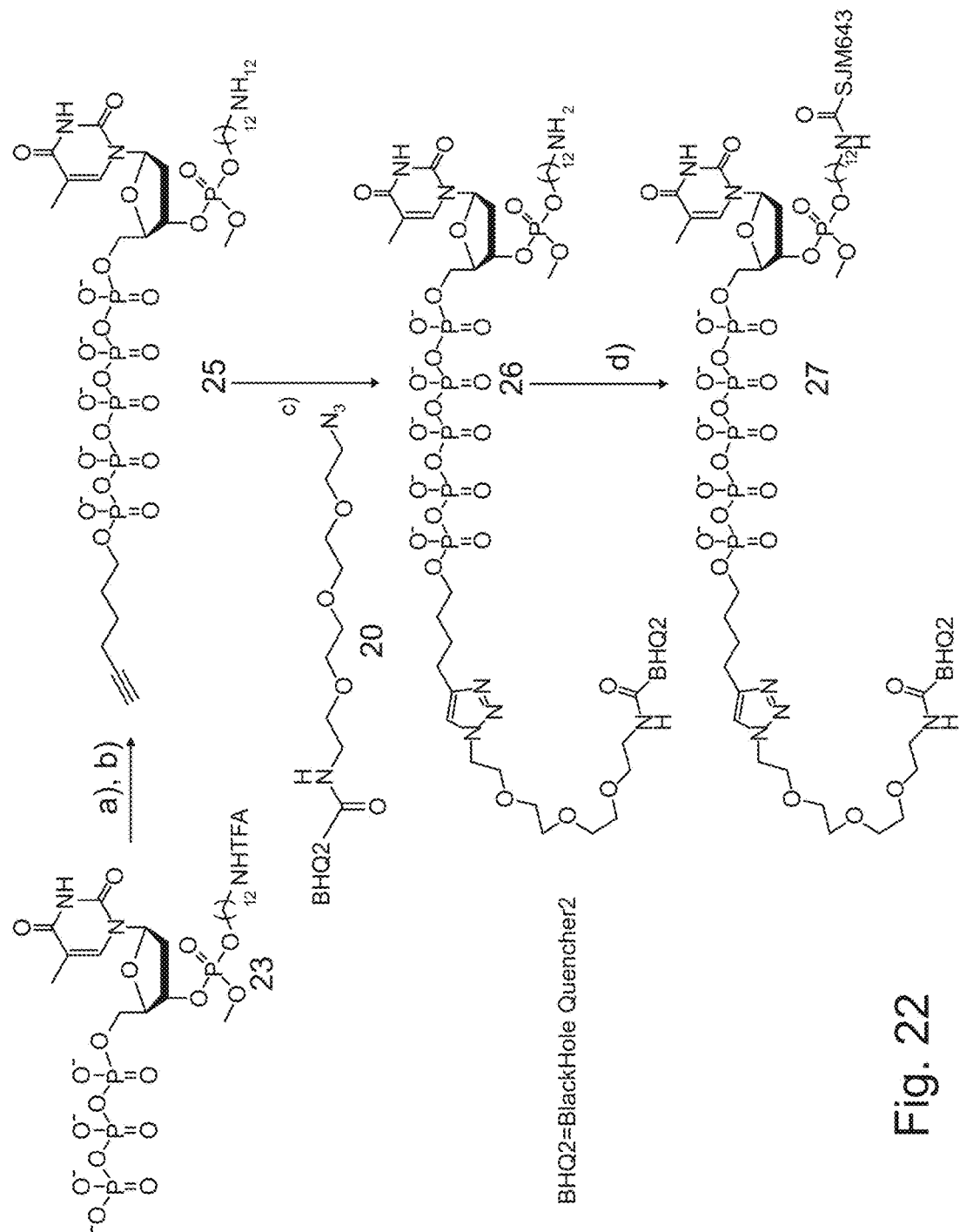

FIG. 22 shows a diagrammatic scheme for synthesis of a quencher/dye labeled nucleotide 5'-pentaphosphate 3'-phosphotriester. Reagents: a) 1) 17, CDI, DMF; 2) MeOH; 3) 23, DMF, ZnCl$_2$. b) K$_2$CO$_3$, MeOH/H$_2$O 8:2. c) 20, CuSO$_4$, TBTA, Na ascorbate, tBuOH/H$_2$O/DMF. d) SJM643-COOH, TSTU, DIPEA, DMF.

Figure 23:
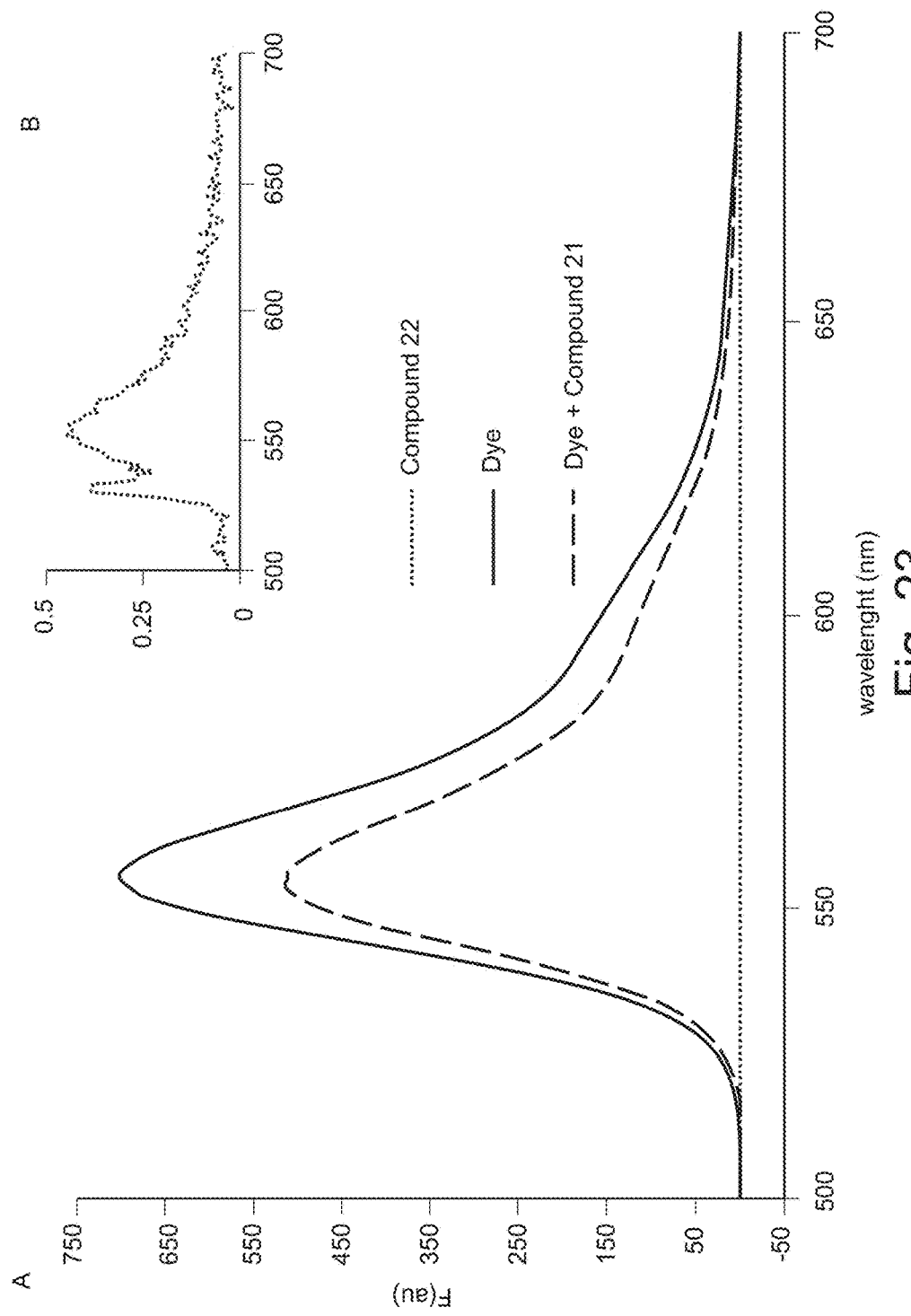

FIG. 23 shows in Panel A: Fluorescence emission (AU) of nucleotide 22 (dotted line) at approximately 4 μM, the dye Atto532 at 4 μM (solid line) and an equimolar mixture of the dye Atto532 and the compound 21 at 4 μM (dashed line). All solutions were prepared in 10 mM Tris pH 8.0. Panel B: Zoom-in of the fluorescence trace of the nucleotide 22. Excitation wavelength: 532 nm.

Figure 24:
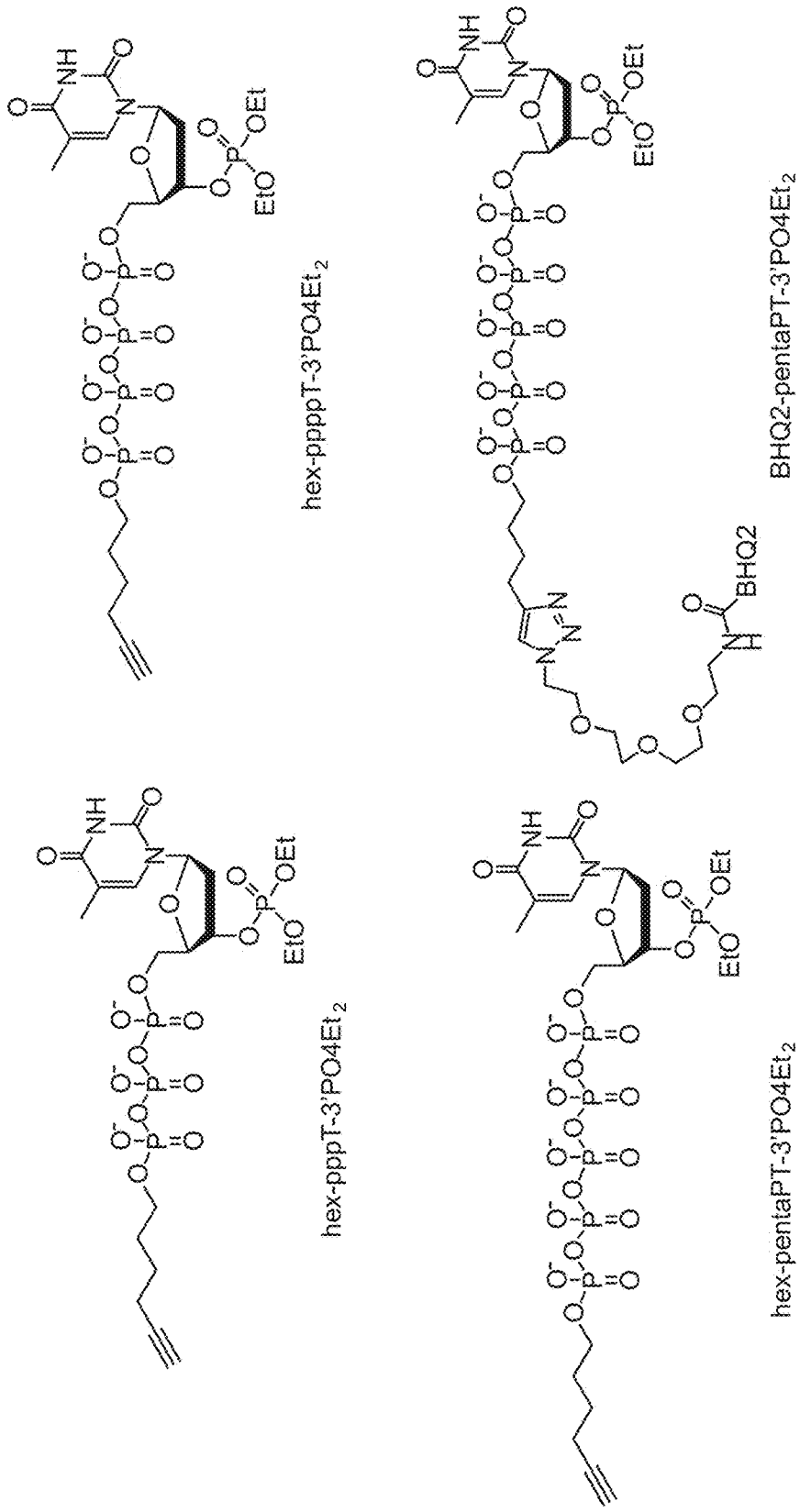

FIG. 24 shows structures of nucleotides used to test the influence of attachments of 5' phosphate on incorporation. BHQ2=BlackHole Quencher 2.

DETAILED DESCRIPTION

The present disclosure provides a method for synthesizing a nucleic acid by carrying out a primer extension reaction in the presence of a polymerase, reversibly blocked nucleotide analogs and a deblocking agent. The nucleic acid, polymerase, reversibly blocked nucleotide analogs and deblocking agent can be present in the reaction simultaneously. The polymerase is capable of catalyzing addition of a single reversibly blocked nucleotide analog to the primer to create an extended primer having a blocked 3' terminus. The deblocking agent is capable of deblocking the 3' terminus of the extended primer such that subsequent nucleotide analogs can be added to the extended primer. Because the reagents are together simultaneously, the primer can be sequentially extended to incorporate several nucleotide analogs in a single pot reaction. An advantage of a single pot reaction is that reagents need not be added to the reaction nor removed from the reaction, thereby reducing reagent waste caused by repetitive fluid transfers and increasing turnaround time for the reaction by minimizing time consuming fluidic transfer steps.

Also provided is a method of determining the sequence of a nucleic acid template by extending a primer to which the template is hybridized, the primer extension reaction being carried out in the presence of a polymerase, reversibly blocked nucleotide analogs and a deblocking agent. For example, a mixture can be provided that includes a primer nucleic acid hybridized to a template nucleic acid, a polymerase, reversibly blocked nucleotide analogs having detectable labels and a deblocking agent. This mixture can be used in a sequencing-by-synthesis (SBS) method such that a reaction cycle is repeated several times in the mixture. Each reaction cycle can include the sequential steps of (a) a polymerase catalyzed addition of a single nucleotide analog to the primer to create an extended primer having a label and a blocked 3' terminus; (b) detection of the label that was added to the extended primer, and (c) deblocking the 3' terminus of the extended primer such that the primer is available for a subsequent cycle of nucleotide addition. In several embodiments the SBS methods set forth herein provide the advantage of being carried out in a one pot reaction, thereby avoiding sequential addition of reagents which can be costly and time consuming.

This disclosure further provides reaction mixtures that include reagents for synthesizing a nucleic acid or carrying out a SBS method. An exemplary reaction mixture includes a nucleic acid, polymerase, reversibly blocked nucleotide analogs (which can optionally be labeled) and a deblocking agent. As set forth in further detail below, the amount and/or concentration of one or more reagents in a reaction mixture can be adjusted to control or influence the lifetime for various transient species that are produced and consumed in a reaction cycle. Thus, the rate of sequencing and timeframe for detection of incorporated nucleotide analogs is tunable. For example, the concentration (or amount) of polymerase, one or more nucleotide analogs or deblocking agent can be adjusted to provide a desired lifetime for an extended primer, having a label and a blocked 3' terminus, that is produced transiently in an SBS reaction. Specifically, the lifetime of the transiently detectable primer extension product can be increased by decreasing the concentration (or amount) of the deblocking agent, and/or by increasing the concentration (or amount) of the polymerase.

Also provided is a deblocking agent that is selective for a blocking moiety on a nucleic acid (compared the same blocking moiety on a monomeric nucleotide). This selectivity allows blocked, monomeric nucleotide analogs to be present in a reaction mixture where a blocking moiety is removed from an extended primer. As such, a single pot reaction can be carried out in which an excess of the blocked, monomeric nucleotide analogs is retained through several cycles of primer extension. An advantage of using a selective deblocking agent is the ability to control reaction rate and the lifetime for transient products formed during each cycle of a primer extension reaction. The use of a selective deblocking agent can allow a level of control and analysis in a single pot SBS reaction that is otherwise achieved at the expense of fluidically replacing reagents multiple times in a traditional SBS reaction.

This disclosure further provides a nucleotide analog having a blocking moiety, a label moiety and a label-modifier moiety. The label moiety can be configured to produce a detectable signal. The label-modifier moiety can be configured to interact with the label moiety to alter the detectable signal. For example, the label moiety can be a fluorophore and the label-modifier moiety can be a quencher. In particular embodiments, the presence or absence of the label-modifier can be used to distinguish whether the nucleotide is in a monomeric state or in a polymeric state, having been incorporated into a polynucleotide. For example, a nucleotide analog can include a fluorescent label attached to the 3' position of the pentose moiety and a quencher attached to the beta or gamma phosphate at the 5' position such that the fluorescent label is quenched in the monomeric nucleotide triphosphate. Addition of the nucleotide analog into a polynucleotide will result in removal of the quencher (due to hydrolysis of pyrophosphate) and the nucleotide will become fluorescent. Thus, incorporation of the nucleotide in the polynucleotide can be determined based on the appearance of the fluorescent signal.

Terms used herein will be understood to take on their ordinary meaning in the relevant art unless specified otherwise. Examples of several terms used herein and their definitions are set forth below.

As used herein, the term "mixture" means a combination of two or more different things. The different things are simultaneously together, for example, in a liquid, in a gas, in a gel, on a surface or as a combination thereof. An exemplary combination is a surface bound reaction component that is in contact with a solution phase component. A mixture can be distinguished from a chemical compound in that the two or more different things are not necessarily in fixed proportions, need not lose their individual characteristics, and can be separated by physical means. It will be understood that two or more things in a reaction can react with each other to subsequently form a chemical compound.

As used herein, the term "nucleic acid" can be used refer to at least two nucleotide analog monomers linked together. A nucleic acid can contain phosphodiester bonds, however, in some embodiments, a nucleic acid can be an analog having other types of backbones, comprising, for example, phosphoramide, phosphorothioate, phosphorodithioate, peptide nucleic acid backbones and linkages, positive backbones, or non-ionic backbones. A nucleic acid can include a pentose moiety such as ribose (present in naturally occurring RNA), deoxy-ribose (present in naturally occurring DNA) or dideoxy ribose. In some embodiments a nucleic acid can have a non-pentose moiety or carbocyclic sugar instead of a ribose or deoxyribose moiety. A nucleic acid can have one or more different base moieties including, but not limited to, adenine (A), guanine (G), thymine (T), uracil (U), cytosine (C), inosine, xanthanine, hypoxanthanine, isocytosine, isoguanine, nitropyrrole (including 3-nitropyrrole) and/or nitroindole (including 5-nitroindole). Nucleic acids may be single stranded or double stranded, as specified, or contain portions of both double stranded and single stranded sequence. The nucleic acid may be DNA (e.g. genomic DNA or cDNA), RNA or a hybrid.

As used herein, the term "nucleotide analog" is intended to include natural nucleotides, non-natural nucleotides, ribonucleotides, deoxyribonucleotides, dideoxyribonucleotides and other molecules known as nucleotides. The term can be used to refer to a monomer unit that is present in a polymer, for example to identify a subunit present in a DNA or RNA strand. The term can also be used to refer to a monomeric molecule that is not necessarily present in a polymer, for example, a molecule that is capable of being incorporated into a polynucleotide in a template dependent manner by a polymerase. The term can refer to a nucleoside unit having, for example, 0, 1, 2, 3, 4, 5 or more phosphates on the 5' carbon. A nucleotide analog can have a base moiety including, but not limited to, adenine (A), guanine (G), thymine (T), uracil (U), cytosine (C), inosine, xanthanine, hypoxanthanine, isocytosine, isoguanine, nitropyrrole (including 3-nitropyrrole) and/or nitroindole (including 5-nitroindole). Exemplary natural nucleotides include, without limitation, ATP, UTP, CTP, GTP, ADP, UDP, CDP, GDP, AMP, UMP, CMP, GMP, dATP, dTTP, dCTP, dGTP, dADP, dTDP, dCDP, dGDP, dAMP, dTMP, dCMP, and dGMP.

Non-natural nucleotides include those that are not present in a natural biological system. A non-natural nucleotide can be incapable of being further extended after being incorporated into a polynucleotide. Examples include, nucleotide analogs having a reversible or non reversible blocking moiety. A natural or non-natural nucleotide can be capable of being further extended after being incorporated into a polynucleotide. Examples include, nucleotide analogs having a 3' hydroxyl. In some embodiments, the nucleotide analog(s) will not include a reversible blocking moiety, or the nucleotide analog(s) will not include a non-reversible blocking moiety or the nucleotide analog(s) will not include any blocking moiety at all.

As used herein, the term "blocking moiety," when used in reference to a nucleotide analog, means a part of the nucleotide analog that inhibits or prevents the nucleotide analog from forming a covalent linkage to a second nucleotide analog. For example, in the case of nucleotide analogs having a pentose moiety, a blocking moiety can prevent formation of a phosphodiester bond between the 3' oxygen of the nucleotide and the 5' phosphate of the second nucleotide. The blocking moiety can be part of a nucleotide that is a monomer unit present in a nucleic acid polymer or the blocking moiety can be a part of a free nucleotide analog (e.g. a nucleotide triphosphate). The blocking moiety that is part of a nucleotide analog can be reversible, such that the blocking moiety can be modified to render the nucleotide analog capable of forming a covalent linkage to a second nucleotide analog. Particularly useful reversible blocking moieties are phosphates, phosphodiesters, phosphotriesters, phosphorothioate esters, and carbon esters. Further examples of reversible blocking moieties that can be used are set forth below and in references incorporated by reference herein as set forth below. In particular embodiments, a blocking moiety, such as a reversible blocking moiety, can be attached to the 3' position or 2' position of a pentose moiety of a nucleotide analog.

As used herein, the term "label moiety," when used in reference to a nucleotide analog, means a part of the nucleotide analog that provides a distinguishable characteristic that is not otherwise manifest in the nucleotide analog. The distinguishable characteristic can be, for example, an optical signal such as absorbance of radiation, fluorescence emission, luminescence emission, fluorescence lifetime, fluorescence polarization, or the like; binding affinity for a ligand or receptor; magnetic properties; electrical properties; charge; mass; radioactivity or the like. Exemplary label moieties include, without limitation, a fluorophore, luminophore, chromophore, radioactive isotope, mass label, charge label, spin label, receptor, ligand, or the like. The label moiety can be part of a nucleotide that is a monomer unit present in a nucleic acid polymer or the label moiety can be a part of a free nucleotide analog (e.g. a nucleotide triphosphate).

As used herein, the term "label-modifier moiety," when used in reference to a nucleotide analog having a label moiety, means a part of the nucleotide analog that changes a distinguishable characteristic of the label moiety. Typically, the change in the distinguishable characteristic is manifest in the presence of the label-modifier moiety but not in the absence of the label-modifier moiety. For example, a label-modifier moiety can be a quencher that reduces fluorescence or luminescence emission from a label. In another example, a label-modifier moiety can be a Förster resonance energy transfer (FRET) donor or acceptor that changes the intensity or wavelength of fluorescence or luminescence emission detected from the label. The label-modifier moiety can be part of a nucleotide that is a monomer unit present in a nucleic acid polymer or the label-modifier moiety can be a part of a monomeric nucleotide analog (e.g. a nucleotide triphosphate).

As used herein, the term "deblocking agent" means a catalyst, enzyme, reagent or other substance that is capable of modifying or removing a blocking moiety. In particular embodiments, a deblocking agent can have specificity for a blocking moiety that is part of a nucleotide that is a monomer unit present in a nucleic acid polymer. As such the deblocking agent may selectively remove a blocking moiety from a nucleotide analog that is present in a nucleic acid compared to a blocking moiety that is part of a monomeric nucleotide analog (e.g. a nucleotide triphosphate). Alternatively or additionally, a deblocking agent can selectively remove a blocking moiety from a nucleotide analog that is present in a double stranded nucleic acid compared to a blocking moiety that is part of a monomeric nucleotide analog (e.g. a nucleotide triphosphate) or part of a nucleotide analog that is a monomer in a single stranded nucleic acid. Accordingly, in some embodiments the deblocking agent can have little or no ability to remove a blocking moiety from a monomeric nucleotide analog (e.g. a nucleotide triphosphate) or from nucleotide analog that is a monomer in a single stranded nucleic acid. Exemplary deblocking agents include, but are not limited to, an enzyme, such as a phosphoesterase, phosphodiesterase, phosphotriesterase, esterase, alkyl transferase or methyl transferase; or a chemical reagent.

As used herein, reference to "selectively" manipulating (or "selective" manipulation of) a first thing compared to second thing is intended to mean that the manipulation has a greater effect on the first thing compared to the effect on the second thing. The manipulation need not have an effect on the second thing. The manipulation can have an effect on the first thing that is at least 1%, 5%, 10%, 25%, 50%, 75%, 90%, 95%, or 99% greater than the effect on the second thing. The manipulation can have an effect on the first thing that is at least 2 fold, 3 fold, 4 fold, 5 fold, 10 fold, 100 fold, $1 \times 10^3$ fold, $1 \times 10^4$ fold or $1 \times 10^6$ fold higher than the effect on the second thing. The manipulation can include, for example, modifying, contacting, treating, changing, cleaving (e.g. of a chemical bond), photo-chemically cleaving (e.g. of a chemical bond), forming (e.g. of a chemical bond), photo-chemically forming (e.g. of a chemical bond), covalently modifying, non-covalently modifying, destroying, photo-ablating, removing, synthesizing, polymerizing, photo-polymerizing, amplifying (e.g. of a nucleic acid), copying (e.g. of a nucleic acid), extending (e.g. of a nucleic acid), ligating (e.g. of a nucleic acid), or other manipulation set forth herein or otherwise known in the art.

As used herein, the term "solid-phase support" can include an object having a rigid composition, or collection of such objects. Particularly useful solid-phase supports are those to which at least one molecule, such as a nucleic acid or protein, can be attached. Useful materials for a solid-phase support include, for example, those that are separable from each other such as beads, particles, microspheres, or chromatographic supports; and those that form a continuous material such as a flow cell, microchip or other chip, microscope slide, planar surface, or the like. Particularly useful materials are those used for microarrays. Useful materials for a microarray or other solid-phase support include, but are not limited to, glass; modified glass; functionalized glass; plastics such as acrylics, polystyrene and copolymers of styrene and other materials, polypropylene, polyethylene, polybutylene, polyurethanes, Teflon, or the like; polysaccharides; nylon; nitrocellulose; resins; silica; silica-based materials such as silicon or modified silicon; carbon; metal; inorganic glass; optical fiber bundles, or any of a variety of other polymers. Useful solid-phase supports include those that allow optical detection, for example, by being translucent to energy of a desired detection wavelength and/or do not produce appreciable background fluorescence at a particular detection wavelength. The solid-phase support may be contained in or part of a flow chamber such as a flow cell, allowing convenient movement of liquids across the surface to enable the transfer of reagents. Exemplary flow cells that can be used are described in WO 2007/123744, which is incorporated herein by reference in its entirety.

As used herein, the term "array" means a population of different molecules that are attached to one or more solid-phase substrates such that the different molecules can be differentiated from each other according to their relative location. An array can include different molecules that are each located at a different addressable location on a solid-phase substrate. Alternatively, an array can include separate solid-phase substrates each bearing a different molecule, wherein the different probe molecules can be identified according to the locations of the solid-phase substrates on a surface to which the solid-phase substrates are attached or according to the locations of the solid-phase substrates in a liquid such as a fluid stream. The molecules of the array can be, for example, nucleic acid primers, nucleic acid probes, nucleic acid templates or nucleic acid enzymes such as polymerases.

As used herein, the term "transient," when used in reference to a species in a reaction or reaction cycle, means the species is present only temporarily during the course of the reaction or reaction cycle. A transient species can be present, for example, for a time period that is no more than about 10 minutes, 1 minute, 30 seconds, 10 seconds, 1 second, 100 milliseconds, 10 milliseconds, 1 millisecond, 100 nanoseconds, 10 nanoseconds, or 1 nanosecond. In particular embodiments, the transient species is present for a temporary time period that is sufficient to allow detection of the transient species. For example, additionally or alternatively to the exemplary maximum times periods set forth above, a transient species may be present for at least 1 minute, 30 seconds, 10 seconds, 1 second, 100 milliseconds, 10 milliseconds, 1 millisecond, 100 nanoseconds, 10 nanoseconds, 1 nanosecond or 1 picosecond.

As used herein, the term "reaction cycle," when used in reference to a reactant and product, means a sequence of two or more reactions that convert the reactant to at least one transient species and then convert the at least one transient species to the product. The reaction cycle can be repeated, for example, such that the product serves as a reactant in the same sequence of reactions. For example, a nucleic acid primer can be extended by a single nucleotide in a first reaction cycle to produce a primer extension product (having a single nucleotide added to the original primer) and then the primer extension product can be extended again in a second reaction cycle to produce a primer extension product (having two nucleotides added to the original primer). The repetition of the cycle can use slightly different reactants, for example, different nucleotide analogs can be added in sequential cycles of primer extension. However, a reaction cycle need not be repeated. A nucleic acid reaction cycle can, for example, result in the addition of a single nucleotide to a primer (e.g. in a polymerase catalyzed reaction) or in the addition of a single oligonucleotide to a primer (e.g. in a ligase catalyzed reaction).

Provided herein is a method of synthesizing a polynucleotide. The method can include the steps of (a) providing a mixture including a nucleic acid, a collection of different nucleotide analogs, a polymerase and a deblocking agent, and (b) allowing sequential addition of a plurality of the different nucleotides analogs to the nucleic acid to proceed via several reaction cycles in the mixture, wherein each reaction cycle includes the steps of (i) the polymerase adding a nucleotide analog to the nucleic acid to form a transient nucleic acid species comprising a blocking moiety, and (ii) the deblocking agent modifying the transient nucleic acid species to remove the blocking moiety.

A polynucleotide can be synthesized in a method set forth herein by extension of a partially double stranded nucleic acid. Generally, the two strands of the nucleic acid are identified as a "template strand" (or "template" or "template polynucleotide" or "template nucleic acid") and a primer strand (or "primer" or "primer polynucleotide" or "primer nucleic acid"), respectively. The primer is generally shorter than the template to which it is hybridized. As such, the double stranded portion of the nucleic acid occurs where the primer is hybridized to the template and a single stranded portion occurs for that part of the template that is not hybridized to the primer strand. According to various embodiments set forth herein, polynucleotide synthesis occurs via polymerase catalyzed addition of one or more nucleotide analogs to the 3' end of the primer using the template as a guide. The template acts as a guide in accordance with Watson-Crick base pairing (e.g. adenine and thymine base pair with each other; and cytosine and guanine base pair with each other).

The examples set forth herein with regard to primer extension are provided for illustration and are not necessarily intended to be limiting. Various nucleic acid configurations are known in the art that support polynucleotide synthesis and will therefore be understood to be applicable to the methods set forth herein. For example, a nucleic acid can form a hairpin structure such that the primer strand and the template strand are formed from a nucleic acid that can be denatured to form a single strand. Furthermore, a primer strand can be short or long, it can be previously extended by addition of nucleotide analogs, and in some cases it can be longer than the template to which it is hybridized (for example, by having a 5' overhang).

A nucleic acid used in a method set forth herein can be solution phase or solid-phase. The nucleic acid when in solution phase is generally soluble, but can also be in a suspended form that is capable of being precipitated, as is the case for some large nucleic acid species such as chromosomes or nucleic acid nanoballs (see, for example, US Pat. Publ. No. 2007/0099208 A1, which is incorporated herein by reference). A nucleic acid that is solid-phase can occur in a solid-phase support or on a solid-phase support. Exemplary solid-phase supports include those made from glass, nitrocellulose, silica, metal, plastic and other materials set forth elsewhere herein, for example, with regard to array formats. Similarly, a nucleic acid can occur in or on a semisolid support such as a gel. Exemplary gels that are useful include, but are not limited to, those having a colloidal structure, such as agarose; polymer mesh structure, such as gelatin; or cross-linked polymer structure, such as polyacrylamide. Hydrogels are particularly useful such as those set forth in US Pat. Pub. No. 2011/0059865 A1, which is incorporated herein by reference.

Attachment of a nucleic acid to a support, whether rigid or semi-rigid, can occur via covalent or non-covalent linkage(s). Exemplary linkages are set forth in U.S. Pat. Nos. 6,737,236; 7,259,258; 7,375,234 and 7,427,678; and US Pat. Pub. No. 2011/0059865 A1, each of which is incorporated herein by reference. In some embodiments, a nucleic acid or other reaction component can be attached to a gel or other semisolid support that is in turn attached or adhered to a solid-phase support. In such embodiments, the nucleic acid or other reaction component will be understood to be solid-phase.

In various embodiments, blocking moieties function to prevent a particular reaction from proceeding. For example, a nucleotide analog can have a blocking moiety that prevents reaction of the 3' oxygen of the nucleotide analog with the 5' phosphate of another nucleotide. A blocking moiety can be specific for a particular reaction. Taking again the example of a nucleotide analog, a blocking moiety can specifically prevent the 3' oxygen of a first nucleotide analog from reacting with the 5' phosphate of a second nucleotide, and yet the blocking moiety does not prevent the first nucleotide analog from being added to a primer by a polymerase (i.e. the blocking moiety does not prevent the 5' phosphate of the first nucleotide analog from reacting with the 3' oxygen of the primer). Reversible blocking moieties are particularly useful because they can be reacted with an appropriate deblocking agent to allow the reaction to proceed. Returning to the nucleotide analog exemplified above, the blocking moiety, having been incorporated into the extended primer, can be treated with an appropriate deblocking agent to render the extended primer capable of further extension. For clarity, blocking moieties are exemplified with regard to a nucleotide analog having a pentose moiety with a 3' oxygen and 5' triphosphate. It will be understood that a blocking moiety can provide a similar function of preventing extension for nucleotide analogs having other structures.

A blocking moiety can inhibit or prevent a reaction by being directly attached to a reactive moiety that would otherwise participate in the reaction. In the case of a blocking moiety that inhibits or prevents a first nucleotide analog from forming a covalent linkage to a second nucleotide analog, the blocking moiety can be attached to the moiety of the first nucleotide analog that would otherwise form the covalent linkage to the second nucleotide analog. Take for example a nucleotide analog having a pentose moiety with an oxygen atom at the 3' position and a triphosphate at the 5' position. The 3' oxygen of a first nucleotide analog is typically reactive with the 5' phosphate of a second nucleotide analog in the presence of a polymerase. However, a blocking moiety can be attached to the 3' oxygen of the first nucleotide analog to prevent the reaction with the 5' phosphate of the second nucleotide analog. The block can be reversed by removing the blocking moiety to yield an oxygen (or hydroxyl) at the 3' position. It is also possible to attach a blocking moiety to the carbon at the 3' position of the pentose moiety. Such a block can be reversed by removing or modifying the blocking moiety in a way to produce an oxygen (or hydroxyl) at the 3' position.

A blocking moiety need not be directly attached to the reactive moiety that is to be prevented from reaction. For example, a blocking moiety that inhibits or prevents a first nucleotide analog from forming a covalent linkage to a second nucleotide analog, can be attached to a moiety of the first nucleotide analog other than the moiety that would otherwise form the covalent linkage to the second nucleotide analog. Taking again the example of a nucleotide analog having a pentose moiety with an oxygen at the 3' position and a triphosphate at the 5' position, a blocking moiety can be attached at a moiety other than the 3' oxygen. A particularly useful moiety for attachment of a blocking moiety is the 2' carbon of the pentose moiety. For example, a bulky moiety at the 2' carbon can prevent reaction of the 3' oxygen. This may be due to steric hindrance or charge repulsion to name a few possibilities. A blocking moiety can also be placed at other positions of the pentose moiety (e.g. at the 5' position) or at various positions of the base moiety of the nucleotide analog. For example, blocking moieties at these positions can function to inhibit polymerase binding and/or catalytic activity A desirable property of a blocking moiety, when used in several embodiments set forth herein, is selective reversibility that allows a blocked reaction to be deblocked (i.e. allowed to proceed) in a controlled manner. Selective reversibility can be achieved by choice of an appropriate deblocking agent. For example, selective deblocking can occur via reaction of a blocking moiety with a specific chemical agent such as an oxidant, reducing agent, enzyme or catalyst. Blocking moieties that include a phosphate moiety are particularly useful. The phosphate moiety can form a covalent bond to a nucleotide analog at any of a variety of positions including, for example, the phosphate can be attached at the 2' or 3' position of a pentose moiety. The phosphate moiety can be in a phosphodiester or phosphotriester form such that at least one of the esters forms a linkage with the nucleotide analog. Other analogs can also be useful such as a phosphorothioate ester. A phosphate moiety when used as a blocking moiety can be removed or otherwise deblocked by using an enzyme-based deblocking agent that can include, for example, a phosphatase, phosphoesterase, phosphodiesterase or phosphotriesterase. Examples of enzymes that can be used to deblock a nucleotide analog having a phosphate blocking moiety include, but are not limited to, Endonuclease IV (EndoIV), AP endonuclease 1 (APE1), Ada protein, alkaline phosphatase and T4 polynucleotide kinase. The Ada protein is believed to react stoichiometrically with substrates and is often referred to in the art as a suicide enzyme or sacrificial protein. For purposes of this disclosure, the Ada protein will be understood to be an enzyme.

Particularly useful enzymes that can be used to deblock a nucleotide analog are *E. coli* endonuclease IV, Tth endonuclease IV (from *Thermus thermophiles*) and related enzymes from other organisms such as *Thermococcus*. *E. coli* endo IV provides a DNA-specific 3' phosphodiester/triester activity and the ability to tolerate a large group attached to the 3' phosphate. Endonuclease IV enzymes from other organisms having the same or similar activity are also useful. Unblocking of a nucleotide can generate a nucleotide species having free 3'OH. Tth endo IV is thermostable making it particularly useful for conditions that utilize elevated temperatures. Other enzymes or reagents having this activity are suitable for embodiments of the present disclosure. An enzyme or reagent that does not directly generate a free 3' OH, but a different group that can subsequently be modified to a free 3'OH can also be useful (e.g. Tyrosyl-DNA phosphodiesterase I (Tdp1) which generates a 3' phosphate that can be removed, for example, by Pol 217).

Blocking moieties that include a carbon ester moiety are also useful. The blocking moiety can form a covalent carbon ester bond to a nucleotide analog at any of a variety of positions including, for example, in cases where the nucleotide has a pentose moiety, at the 2' or 3' position. Exemplary carbon ester blocking moieties include, without limitation, lower (1-4 carbon) alkanoic acid and substituted lower alkanoic acid esters, such as formyl, acetyl, isopropanoyl, alpha fluoro- and alpha chloroacetyl esters and the like. A carbon ester moiety when used as a blocking moiety can be removed or otherwise deblocked by using an enzyme-based deblocking agent that can include, for example, an esterase. Ether blocking moieties, such as alkyl ethers, are also useful because like phosphate and carbon ester moieties they can be cleaved from the 3' position of the pentose of a nucleotide analog to yield a 3' oxygen that is reactive in polymerase extension and/or ligation.

A deblocking agent can include one or more reactive components. As such a deblocking step used in a method set forth herein can include one or more reactions or modifications of a blocking moiety. The reactions or modifications can occur due to chemical change(s), physical change(s) or a combination thereof. Examples of methods having a deblocking step that includes a single reaction are set forth below in regard to FIG. 1 and FIG. 2. Examples of deblocking steps that include multiple reactions or modifications are set forth below in regard to FIG. 3 and FIG. 4.

Deblocking agents that selectively react with blocking moieties in polymeric nucleotides (i.e. nucleotides present in nucleic acids) compared to monomeric nucleotides are particularly useful. This selectivity allows blocked, monomeric nucleotide analogs to be present when a blocking moiety is removed from an extended primer. As such, a single pot reaction can be carried out in which an excess of the blocked, monomeric nucleotide analogs is retained through several cycles of primer extension. Each cycle of primer extension will produce a blocked primer as a transient intermediate. Producing a transient intermediate in this way provides for control and analysis of the single pot reaction. For example, the rate of overall primer extension can be controlled by adjusting the concentration or amount of reactants that produce or consume the transient intermediate. Furthermore, the transient intermediate can be detected to allow analysis of the primer extension reaction, for example, in sequencing-by-synthesis (SBS) embodiments as set forth in further detail below. Thus, the use of a deblocking agent that selectively reacts with blocking moieties in polymeric nucleotides compared to monomeric nucleotides, can allow a level of control and analysis in a single pot SBS reaction that is otherwise achieved at the expense of fluidically replacing reagents multiple times in a traditional SBS reaction.

Exemplary deblocking agents that are selective for extended primers are enzymes that have 3' repair activity. Examples of such enzymes include Endo IV, APE1 and Ada. Some polymerases contain 3' repair activity and can function as deblocking agents in particular embodiments set forth herein. However, in some embodiments such polymerases may be avoided altogether. Depending upon the desired application of the compositions and methods set forth herein, it may be desirable to use a polymerase that has little or no substantial 3' repair activity for an extended primer under the conditions present in a particular reaction mixture. If desired a combination of polymerases with and without 3' repair activity can be used. As set forth elsewhere herein the concentration or amount of each polymerase can be adjusted to tune the rate of a reaction cycle and the lifetime of transient intermediates of the reaction cycle.

Figure 5:
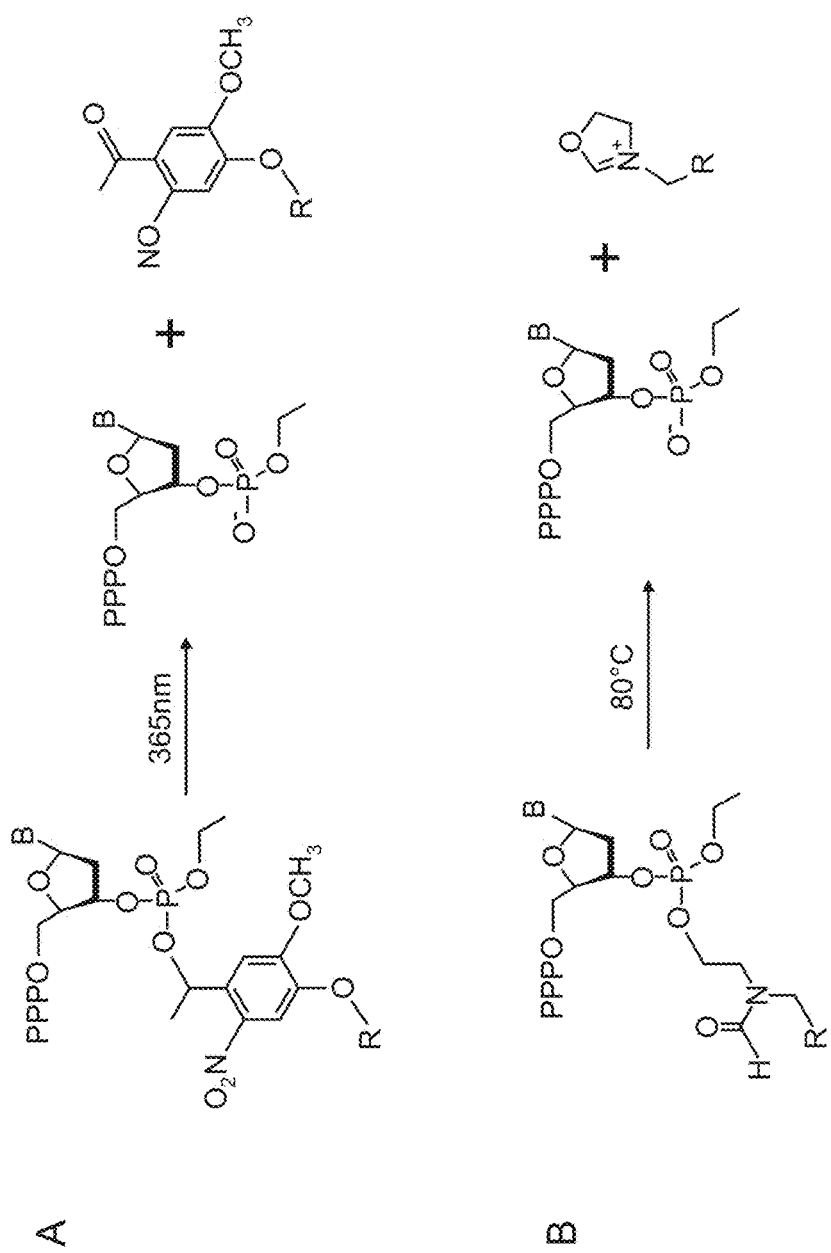
FIG. 5 shows examples of caged nucleotide analogs and reactions for uncaging them.

Selective reversibility of a blocking moiety can also include the use of an appropriate physical stimulus, such as electromagnetic radiation, temperature change, voltage etc. For example, a photo-chemically cleavable blocking moiety can be used. In some embodiments a photo-chemical linkage can occur between a nucleotide analog and blocking moiety such that irradiation with light of an appropriate wavelength will release the blocking moiety to yield a nucleotide analog that is capable of extension by a polymerase. Exemplary photo-cleavable moieties include, but are not limited to (1-(4,5-dimethoxy-2-nitrophenyl)ethyl) ester (i.e. DMNPE) and (1-(2-nitrophenyl)ethyl) ester (i.e. NPE). See *Meth. Enzymol.* 291:307-347 (1998), which is incorporated herein by reference. Another useful photo-cleavable moiety is shown in FIG. 5. Other photo-cleavable blocking moieties, and methods for their synthesis and use, are described in WO 91/06678 or US Pat. Appl. Publ. No. 20100092957 A1, each of which is incorporated herein by reference.

Other blocking moieties and deblocking agents that can be used in a method or composition set forth herein, and methods for their synthesis and use are described, for example, in U.S. Pat. No. 6,232,465; 6,664,079; 7,057,026; 7,414,116; 7,427,673; or 7,541,444; WO 91/06678 or US Pat. Appl. Publ. No. 2010/0092957 A1, each of which is incorporated herein by reference.

In some embodiments a blocking moiety is not necessary or not desirable. Thus, a nucleotide analog that is present in a reaction mixture or used in a reaction set forth herein may lack a blocking moiety when in a monomeric form and when incorporated into an extended primer. The nucleotide analog may nonetheless include a label moiety and/or label-modifier moiety.

A nucleic acid extension reaction, or other cyclic reaction, that is carried out using methods set forth herein can proceed for one or more cycles. In particular embodiments, a multicycle reaction can include at least 2 cycles, 5 cycles, 10 cycles, 50 cycles, 100 cycles, 500 cycles, 1,000 cycles, 5,000 cycles, 10,000 cycles or more. Alternatively or additionally, a reaction can have an upper limit whereby no more than 1 cycle, 2 cycles, 5 cycles, 10 cycles, 50 cycles, 100 cycles, 500 cycles, 1,000 cycles, 5,000 cycles, or 10,000 cycles occur. In some embodiments utilizing a polymerase catalyzed reaction, each cycle will result in the incorporation of a single nucleotide analog into an extended primer. In this case, the minimum or maximum number of cycles exemplified above can be understood to exemplify the minimum or maximum number of nucleotides incorporated into an extension product in a polymerase catalyzed reaction.

In other embodiments, such as those utilizing ligation-based primer extension, each cycle can result in the incorporation of a single oligonucleotide. As such, the minimum or maximum number of cycles exemplified above can be understood to exemplify the minimum or maximum number of oligonucleotides incorporated into an extension product. The oligonucleotides can have any of a variety of lengths as set forth in further detail below. The length of an extension product produced by ligation can be determined as the mathematical product of multiplying the length of the oligonucleotide by the number of cycles. Applying this type of multiplication to the exemplary oligonucleotide lengths set forth below and the minimum or maximum number of cycles exemplified above can be used to determine the minimum length or maximum length of an extension product of a ligation reaction set forth herein.

A multicycle reaction can be a single pot reaction that results from a single delivery of several different species of nucleotides such that a polymerase is able to add several nucleotides to a growing nucleic acid strand. In such a method, multiple deliveries of reaction components are not necessary to complete the number of cycles or to produce extended primers of the lengths exemplified above. Typically, four different nucleotide analogs will be present in a reaction mixture, but if desired, fewer than four can be present. Different nucleotide analogs (i.e. those having different base moieties) can have different label moieties. As such, incorporation of each type of nucleotide into an extended primer can be distinguished and the sequence of the template to which the primer is annealed can be determined.

Although several embodiments of the methods are described herein with reference to a one pot reaction, it will be understood that one or more components can be added to a reaction mixture or removed from the reaction mixture during a reaction. The addition or removal can occur after a first reaction cycle is complete and prior to completion of the reaction, or a portion thereof. Any number of addition or removal steps can be carried out. For example, addition steps, removal steps or both can occur for each cycle of a multicycle reaction. Alternatively, an addition step, removal step or both can occur periodically after several cycles have been completed.

Examples of components that can be added or removed from a reaction mixture include, without limitation, reactive components such as reactants, enzymes or catalysts. For example, reactants that are consumed during the course of a reaction can be replenished. In the case of a polymerase catalyzed primer extension reaction, nucleotide analogs can be added to the reaction mixture. Similarly, in the case of a ligation reaction, oligonucleotides can be added to the reaction mixture. Enzymes or catalysts can be replenished as well, for example, to compensate for a loss of activity due to denaturation or other occurrence. If desired, one or more components can be removed from a reaction mixture. For example, enzymes or catalysts, whether in an active or inactive state, can be removed from a reaction mixture. Other components of a reaction mixture that can be removed include, but are not limited to, unreacted nucleotide analogs, unreacted oligonucleotides, side products of a deblocking reaction (e.g. a phosphate that is cleaved from a nucleotide analog), side products of a label removal reaction, or transient products of a multistep reaction. Components can be removed from a reaction mixture for any of a variety of reasons including, but not limited to, analysis of the progress or state of the reaction, avoidance of unwanted background signal, avoidance of unwanted side reactions, avoidance of product buildup that inhibits forward progress of the reaction etc. Non-reactive components (e.g. buffers, salts, detergents etc.) can similarly be added to a reaction mixture or removed from a reaction mixture.

One or more reaction components can be removed, for example, by separation of solid-phase components from liquid-phase components. Wash steps can optionally be included in order to more completely remove unwanted liquid-phase component(s) from solid-phase component(s). A particularly useful reaction vessel for such separations is a flow cell. Exemplary flow cells, methods for their manufacture and methods for their use are described in US Pat. App. Publ. No. 2010/0111768 A1, WO 05/065814 and U.S. Ser. No. 61/438,486, each of which is incorporated herein by reference. A flow cell can be used for a single pot reaction or for a reaction in which components are added and/or removed during the course of a cyclic reaction. Whether or not solid-phase separation methods are used, reaction components can be removed by any of a variety of other techniques known in the art including, liquid-liquid extraction, solid-phase extraction, chromatography, filtration, centrifugation or the like.

A method for synthesizing a nucleic acid in accordance with the present disclosure can further include a step of detecting a nucleic acid product. In a multicycle reaction a nucleic acid product can be detected during one or more of the cycles. The nucleic acid product that is detected is typically a transient product. One such transient product is a primer extension product having a reversible blocking moiety. Detection can be facilitated by the presence of a label moiety on the transient species, for example, as a result of a label moiety that is attached to the nucleotide analog that was added in the primer extension step. Detection of a transient product, for example via a label, can occur for each cycle of a multicycle reaction. Exemplary labels and detection methods are set forth in further detail below. However, the examples are not considered to be limiting and it will be understood that other products can be detected as well including, but not limited to, a final nucleic acid product or a side product such as those produced from deblocking reactions set forth herein.

Some embodiments of the methods utilize one or more nucleotide analogs having a removable label moiety. Removable label moieties are advantageous for cyclic reactions because label moieties from previous cycles can be removed prior to the detection step for a cycle of interest, thereby removing background signal. A particularly convenient attachment for a label moiety to a nucleotide analog is at the same location where the removable blocking moiety is attached. For example, the label moiety can be attached to the nucleotide analog via the removable blocking moiety. This is convenient because the label can be removed by the same reaction or stimulus that removes the blocking moiety. This can lead to a more simplified reaction cycle than some embodiments where the label moiety and deblocking moiety are attached to a nucleotide analog at different locations. In some instances the blocking moiety and label moiety can be considered one and the same (either structurally or functionally). However, it is also possible that a first portion of a moiety that is attached to a nucleotide analog can be identified as having a label function (or structure) and a second portion of the moiety can be identified as having a blocking function (or structure).

A label moiety need not be attached to a blocking moiety. In some embodiments, a label moiety can be attached to a nucleotide analog at a location that is different from the location of the nucleotide analog where the blocking moiety is attached. For example, a blocking moiety can be attached to the 3' position of a pentose moiety of a nucleotide analog whereas a label moiety is attached to a base moiety of the nucleotide analog. The attachment for both moieties may nonetheless be reactive to the same reagents. In this instance, the same reagent(s) and/or physical stimulus can be used to remove the blocking moiety and the label moiety. In some cases the linker that attaches the label moiety to the nucleotide analog can be the same linker that attaches the blocking moiety. However, it is also possible to use linkers that are structurally different but functionally cleavable under the same conditions.

In embodiments where the label moiety and blocking moiety are attached at separate locations of a nucleotide analog, the chemistry or stimulus for cleaving either moiety can be different. Thus, the linker that attaches the label moiety to the nucleotide analog can be structurally different from the linker that attaches the blocking moiety to the nucleotide analog. The use of different linkers can provide an advantage of adding a layer of control to a reaction cycle. For example, the concentration or amount of the reagents that cleave the different linkers can be separately adjusted to influence the lifetime of a particular transient species. More specifically, the cleavage reagents can be adjusted to allow the label moiety to have a shorter lifetime than the blocking moiety to allow the label moiety more time to diffuse away from a transient nucleic acid species prior to a subsequent extension step.

Labels that are optically detectable are particularly useful. Examples include chromophores, luminophores and fluorophores. Fluorophores are particularly useful and include, for example, fluorescent nanocrystals; quantum dots, fluorescein, rhodamine, tetramethylrhodamine, eosin, erythrosin, coumarin, methyl-coumarins, pyrene, Malacite green, Cy3, Cy5, stilbene, Lucifer Yellow, Cascade Blue, Texas Red, Alexa dyes, SETA dyes, Atto dyes, phycoerythin, bodipy, and analogs thereof. Useful optical probes are described in Haugland, *Molecular Probes Handbook*, (Eugene, Oreg.) 6th Edition; The Synthegen catalog (Houston, Tex.), Lakowicz, *Principles of Fluorescence Spectroscopy*, 2nd Ed., Plenum Press New York (1999), or WO 98/59066; WO 91/06678 or US Pat. Appl. No. 2010/0092957 A1, each of which is incorporated herein by reference. Optical labels provide an advantage of rapid, relatively non-invasive detection thereby allowing real time monitoring of a cyclic reaction.

Other labels, some of which are non-optical labels, can be used in various embodiments of the methods and compositions set forth herein. Examples include, without limitation, an isotopic label such as a naturally non-abundant radioactive or heavy isotope; magnetic substance; electron-rich material such as a metal; electrochemiluminescent label such as $Ru(bpy)^{32+}$; or moiety that can be detected based on a nuclear magnetic, paramagnetic, electrical, charge to mass, or thermal characteristic. Labels can also include magnetic particles or optically encoded nanoparticles. Such labels can be detected using appropriate methods known to those skilled in the art. For example, a charged label can be detected using an electrical detector such as those used in commercially available sequencing systems from Ion Torrent (Guilford, Conn., a Life Technologies subsidiary) or detection systems described in US Pat. App. Publ. Nos. 2009/0026082 A1; 2009/0127589 A1; 2010/0137143 A1; and 2010/0282617 A1, each of which is incorporated herein by reference. It will be understood that for some embodiments a nucleotide analog need not have a label.

Another type of label that can be useful is a secondary label that is indirectly detected, for example, via interaction with a primary label, binding to a receptor or conversion to a detectable product by an enzyme catalyst or other substance. An exemplary secondary label is a ligand such as biotin or analogs thereof that can be detected via binding to a receptor such as avidin, streptavidin or analogs thereof. Other useful ligands are epitopes that can bind to receptors such as antibodies or active fragments thereof, and carbohydrates that can bind to receptors such as lectins. The receptors can be labeled, for example, with an optical label, to allow them to be detected. In particular embodiments, the ligand can be attached to a nucleotide analog in a way that reduces or prevents affinity to a receptor. Release of the ligand can then be detected based on affinity of the ligand for its respective receptor when detached from the nucleotide analog. The ligand can further be attached to a blocking moiety or may itself function as a blocking moiety, as set forth above more generally for label moieties. Thus, removal of the ligand from a nucleotide analog can function to deblock the nucleotide analog and to provide a detectable event.

Another exemplary secondary label is pyrophosphate or analogs thereof. Pyrophosphate can be detected by solid-phase chelators and/or electronic biosensors. In some embodiments, pyrophosphate can be detected by a cascade of enzymes that converts pyrophosphate to ATP and then to chemiluminescence. Exemplary enzyme cascades include those typically used in pyrosequencing and/or described in US Pat App. Publ. No. 2005/0244870 A1, which is incorporated herein by reference. In some embodiments, use of an enzyme cascade detection system that produces ATP may require use of an Adenine nucleotide analog, such as ATPγS, that is incorporated into a primer by polymerase but does not cause a background signal that competes with the pyrophosphate signal. In particular embodiments, pyrophosphate or an analog thereof can be attached to a nucleotide analog at a position other than the 5' position where a triphosphate resides. This nucleotide analog can produce two pyrophosphate-induced signals in an appropriate detection system, one due to the release of pyrophosphate from the 5' position (due to polymerase activity) and a second due to release from the other position, for example, by a deblocking agent. Production of two pyrophosphate-induced signals can provide an advantage of increased signal to noise in a detection step or increased accuracy in evaluating sequencing data. A particularly useful analog of pyrophosphate, when present on a nucleotide analog, will be charge-neutral at one or more of the oxygen moieties that are typically negatively charged in pyrophosphate. In one example the pyrophosphate analog can have no charged oxygen atoms. Charge neutrality may favor interactions with some polymerase species. The pyrophosphate analog, once released, can be converted to a form for interaction with enzymes in a detection cascade if appropriate or otherwise desired.

A label moiety that is used in a method or composition set forth herein can be an intrinsic label (i.e. an endogenous label) that is present in a naturally occurring molecule being detected, such as a proton or pyrophosphate that is released from a nucleotide analog upon incorporation into an extended primer. Pyrophosphate release can be detected using a pyrosequencing or similar technique, examples of which are commercially available from 454 Life Sciences (Branford, Conn., a Roche Company) or described in US Pat App. Publ. No. 2005/0244870 A1, which is incorporated herein by reference. Exemplary systems for detecting primer extension based on proton release include those that are commercially available from Ion Torrent (Guilford, Conn., a Life Technologies subsidiary) or described in US Pat. App. Publ. Nos. 2009/0026082 A1; 2009/0127589 A1; 2010/0137143 A1; and 2010/0282617 A1, each of which is incorporated herein by reference. Alternatively or additionally to detection of an intrinsic label, one can detect a label that is exogenous to a natural nucleotide analog. Thus, in some embodiments solely exogenous probes are detected such that endogenous probes are not detected, in other embodiments solely endogenous probes are detected such that exogenous probes are not detected and in some embodiments a combination of exogenous and endogenous probes are detected.

In some embodiments a label moiety that is detectable under the conditions being used is not necessary or not desirable. Thus, a nucleotide analog that is present in a reaction mixture or used in a reaction set forth herein may lack a particular detectable label moiety when in a monomeric form and when incorporated into an extended primer. The nucleotide analog may nonetheless include a blocking moiety. In such embodiments, detection may not be carried out at all.

In addition to a label moiety, a nucleotide analog can further include a label-modifier moiety. A label-modifier moiety can function to modify a signal produced by the label moiety. In some embodiments, a signal that is produced by the label moiety in the presence of the label-modifier moiety can be distinguished from a signal that is produced by the label moiety in the absence of the label-modifier moiety. For example, the label moiety and label-modifier moiety can be a Förster resonance energy transfer (FRET) donor-acceptor pair. As such, a change in the wavelength of apparent fluorescence emission from a nucleotide analog can be detected and will be indicative of the presence or absence of the label-modifier moiety. Exemplary fluorophores that can be used as members of FRET pairs include, but are not limited to, fluorescent nanocrystals; quantum dots; d-Rhodamine acceptor dyes including dichloro[R110], dichloro [R6G], dichloro[TAMRA], dichloro[ROX] or the like; fluorescein donor dye including fluorescein, 6-FAM, or the like; Cyanine dyes such as Cy3B; Alexa dyes, SETA dyes, Atto dyes such as Atto 647N which forms a FRET pair with Cy3B and the like.

In another embodiment, the intensity of a signal from a label moiety that occurs in the presence of the label-modifier moiety can be distinguished from the intensity of signal that is produced in the absence of the label-modifier moiety. For example, the label can be a fluorophore and the label-modifier moiety can be a quencher such that absence of the label-modifier moiety can be detected as an apparent increase of fluorescence emission from the nucleotide analog. Exemplary quenchers include, but are not limited to, DACYL(4-(4'-dimethylaminophenylazo)benzoic acid), Black Hole Quenchers (Biosearch Technologies, Novato, Calif.), Qxl quenchers (Anaspec, Freemont, Calif.), Iowa black quenchers, DABCYL, BHQ1, BHQ2, QSY7, QSY9, QSY21, QSY35, BHQO, BHQ1, BHQ2, QXL680, ATTO540Q, ATTO580Q, ATTO612Q, DYQ660, DYQ661 and IR Dye QC-1 quenchers.

A label-modifier moiety is typically attached to a position on a nucleotide analog that allows it to interact with a label in a way that it modifies signal from the label. The label-modifier moiety is also typically attached at a position on the nucleotide and via a linkage that allows it to be readily removed from the nucleotide. A particularly convenient position is a phosphate that is capable of being removed by a polymerase when the nucleotide analog is incorporated into a primer. For example, a label-modifier moiety can be attached to a beta phosphate or a gamma phosphate of a nucleotide analog. Typically, the beta phosphate or gamma phosphate is attached to the 5' position of a pentose moiety. However, it will be understood that for nucleotide analogs having alternative sugar moieties, the label-modifier moiety can be attached to a position having an equivalent function to the beta phosphate or gamma phosphate. The beta phosphate or gamma phosphate are typically found in a triphosphate moiety. However, in particular embodiments a nucleotide analog can have greater than three phosphates, for example, a tetraphosphate or pentaphosphate. In such embodiments, a label-modifier moiety can be attached to the beta phosphate, gamma phosphate, delta phosphate, epsilon phosphate and so on. Often the terminal phosphate of a multiphosphate moiety is a desirable location for attachment of a label-modifier moiety.

Figure 2:
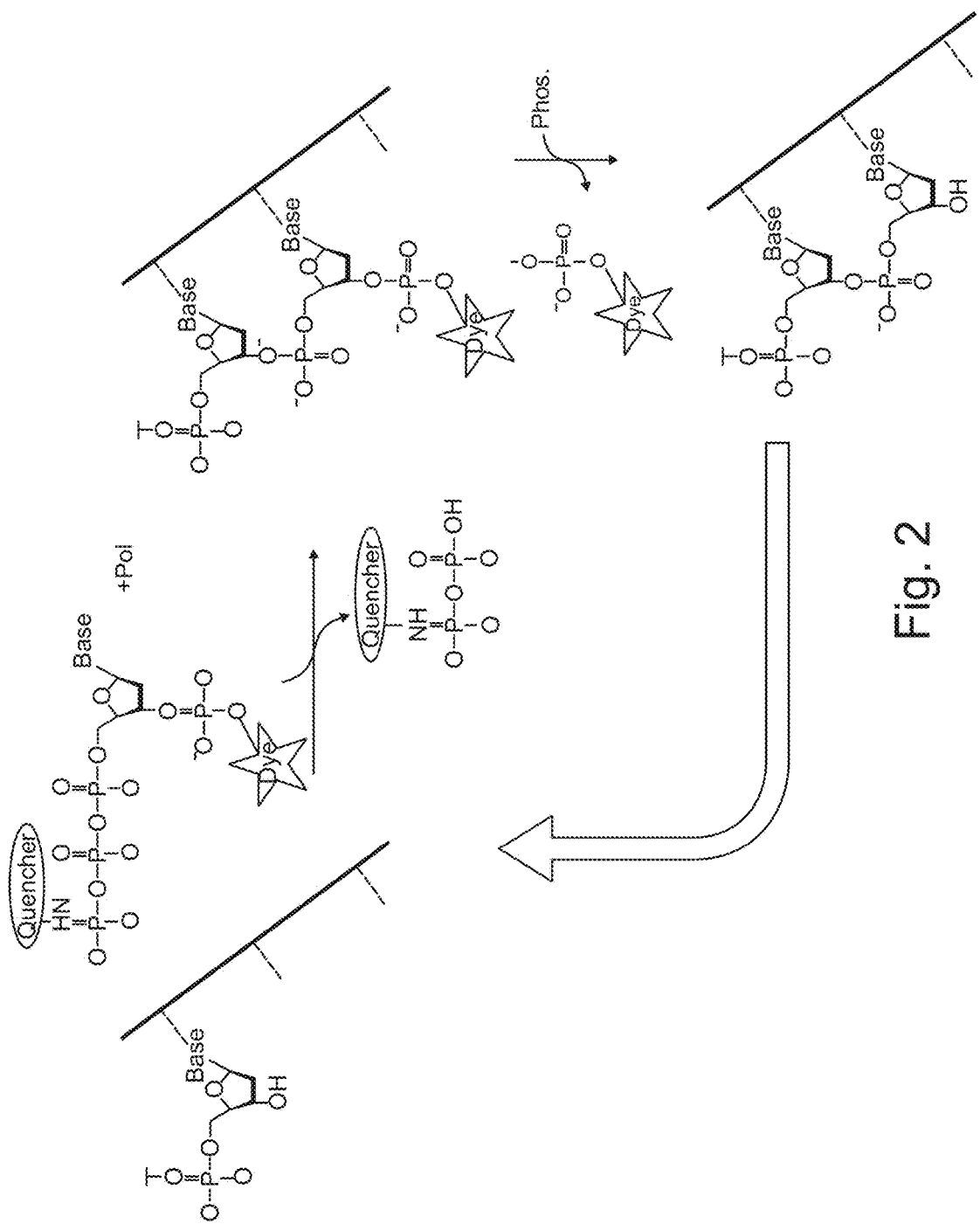
FIG. 2 shows a diagrammatic representation of a reaction cycle in which a polymerase catalyzes addition of a nucleotide analog to a primer and removal of a quenching moiety that is attached to the 5' gamma phosphate of the nucleotide, followed by a phosphodiesterase deblocking agent catalyzing removal of a labeled phosphate blocking moiety from the 3' oxygen of the nucleotide that was added to the primer.

A particularly useful nucleotide analog has a pentose moiety, wherein the 3' position of the pentose moiety is attached to a blocking moiety that in turn functions as a label moiety (e.g. due to attachment of a label moiety to the blocking moiety or due to the blocking moiety being a label moiety too), and wherein the 5' position of the pentose moiety is attached to a label-modifier moiety. FIG. 2 shows an example of such a nucleotide analog, wherein the 3' position of the pentose moiety is attached to a phosphate moiety that is further attached to a fluorophore and wherein a quencher is attached to the gamma phosphate of the triphosphate at the 5' position of the pentose. An advantage of this type of nucleotide analog is that the signal from the label is modified (e.g. quenched for the species in FIG. 2) when the nucleotide analog is in the monomeric state. However, the label modifier is removed when the nucleotide analog is incorporated into a primer by a polymerase to form an extended primer. The blocking moiety and label are retained on the nucleotide analog, at least transiently, in the extended primer. Absent the label-modifier moiety the label moiety on the extended primer produces a distinguishable signal that indicates the presence of the extended primer (or, in other words, indicates that the nucleotide analog has been added to the primer). A further advantage of this type of nucleotide analog is that further extension of the primer will not occur until the blocking moiety is removed. Thus, the extended primer can be detected prior to the extended primer being modified by a deblocking agent. Yet another advantage is that the deblocking agent removes both the blocking moiety and the label moiety to simultaneously render the extended primer capable of extension and to eliminate signal from the extended primer. Thus, throughout the cycle of primer extension and deblocking the presence and absence of signal is well correlated with the state of the primer.

In some embodiments a label-modifier moiety is not necessary or not desirable. Thus, a nucleotide analog that is present in a reaction mixture or used in a reaction set forth herein may lack a label-modifier moiety when in a monomeric form and when incorporated into an extended primer. The nucleotide analog may nonetheless include a blocking moiety and/or label moiety. In such embodiments, an extended primer that has incorporated the nucleotide analog can be distinguished from a monomeric nucleotide by focused or selective detection. For example, the nucleotide analog can have a fluorescent label and the fluorescence detection system can be configured to excite a restricted volume (or area) where the primer is located. Alternatively or additionally, the fluorescence detection system can be configured to detect emission from a restricted volume (or area) where the primer is located. Exemplary fluorescent detection systems for restricting the excitation and/or emission volume include, but are not limited to, systems that focus light, for example using confocal techniques, and systems that physically confine nucleic acids to a detection zone such as detectors that utilize zero mode waveguides.

Any of a variety of polymerases can be used in a method or composition set forth herein including, for example, protein-based enzymes isolated from biological systems and functional variants thereof. Reference to a particular polymerase, such as those exemplified below, will be understood to include functional variants thereof unless indicated otherwise. A particularly useful function of a polymerase is to catalyze the polymerization of a nucleic acid strand using an existing nucleic acid as a template. Other functions that are useful are described elsewhere herein. Examples of useful polymerases include DNA polymerases and RNA polymerases. Particularly useful polymerases include Pol217 and Pol427 as set forth in the Examples section below and other polymerase described in US 2006/0240439 A1, which is incorporated herein by reference.

A polymerase having an intrinsic 3' to 5' proofreading exonuclease activity can be useful for some embodiments. Polymerases that substantially lack 3' to 5' proofreading exonuclease activity are also useful in some embodiments, for example, in most sequencing embodiments. Absence of exonuclease activity can be a wild type characteristic or a characteristic imparted by a variant or engineered polymerase structure. For example, exo minus Klenow fragment is a mutated version of Klenow fragment that lacks 3' to 5' proofreading exonuclease activity.

Polymerases can be characterized according to their rate of dissociation from nucleic acids. In particular embodiments it is desirable to use a polymerase that has a relatively high dissociation rate. This can be useful for example, in embodiments where dissociation of the polymerase allows a deblocking step to proceed. For example, an enzyme when used as a deblocking agent may be sterically blocked by a polymerase such that the enzyme is prevented from removing a blocking moiety from an extended primer. In such a case, the lifetime of the extended primer having the blocking moiety can be influenced by the dissociation rate of the polymerase. The dissociation rate is an activity of a polymerase that can be adjusted to tune reaction rates in methods set forth herein.

Depending on the embodiment that is to be used, a polymerase can be either thermophilic or heat inactivatable. Thermophilic polymerases are typically useful for high temperature conditions or in thermocycling conditions such as those employed for polymerase chain reaction (PCR) techniques. Examples of thermophilic polymerases include, but are not limited to 9° N DNA Polymerase, Taq DNA polymerase, Phusion® DNA polymerase, Pfu DNA polymerase, RB69 DNA polymerase, KOD DNA polymerase, and VentR® DNA polymerase. Most polymerases isolated from non-thermophilic organisms are heat inactivatable. Examples are DNA polymerases from phage. It will be understood that polymerases from any of a variety of sources can be modified to increase or decrease their tolerance to high temperature conditions.

Polymerases can be characterized according to their fidelity when used with a particular nucleotide analog or collection of nucleotide analogs. Fidelity generally refers to the accuracy with which a polymerase incorporates correct nucleotides into a primer when making a copy of a nucleic acid template. DNA polymerase fidelity can be measured as the ratio of correct to incorrect nucleotide analog incorporations when the nucleotide analogs are present at equal concentrations to compete for primer extension at the same site in the polymerase-primer-template DNA binary complex. As proposed by Fersht, DNA polymerase fidelity can be calculated as the ratio of $(k_{cat}/K_m)$ for the correct nucleotide analog and $(k_{cat}/K_m)$ for the incorrect nucleotide analog; where $k_{cat}$ and $K_m$ are the familiar Michaelis-Menten parameters in steady state enzyme kinetics (Fersht, A. R. (1985) *Enzyme Structure and Mechanism*, 2nd ed., p 350, W. H. Freeman & Co., New York., incorporated herein by reference). In particular embodiments, a polymerase can have a fidelity value of at least 100, 1000, 10,000, 100,000, or 1 million, with or without a proofreading activity.

Polymerases that are particularly useful for the methods and compositions herein are set forth below in the context of various examples. It will be understood that the polymerases can be used more generally and need not be limited to the examples provided. Polymerases can be modified using methods well known in the art pertaining to protein engineering. For example, molecular modeling can be carried out based on crystal structures to identify the locations of the polymerases where mutations can be made to modify a target activity. Residue(s) identified as targets for replacement can be replaced with a residue (or residues) selected using energy minimization modeling, homology modeling, and/or conservative amino acid substitutions to determine best case selections derived from known best substitution tables. Such strategies are well known in the art as described, for example, in Bordo, et al. *J Mol Biol* 217: 721-729 (1991), which is incorporated herein by reference. These strategies can be used to generate a library of mutants with desired substitutions. Generation of libraries is well described in the art, for example, in Hayes, et al. *Proc Natl Acad Sci, USA* 99: 15926-15931 (2002), which is incorporated herein by reference.

Polymerase from native sources or variants thereof can be screened using an assay that detects incorporation of a nucleotide analog having a particular structure. In one example, polymerases can be screened for the ability to incorporate a nucleotide analog having a 3' attached phosphate blocking moiety as follows. Test reaction mixtures can be added to the wells of a multiwell plate, where each well has primed DNA templates attached to the bottoms of the wells. The test reaction mixtures can contain a polymerase variant and a nucleotide analog, the nucleotide analog having (1) a base moiety that complements the appropriate position of the template for accurate primer extension to occur and (2) a biotinylated phosphate moiety attached to the 3' position of the deoxyribose. Following sufficient incubation time for extension to occur (e.g. for a control reaction having a polymerase of known reactivity with the nucleotide analog), the reaction mixture can be removed, the wells of the plate washed to remove residual nucleotide analogs, and a development reagent added to the wells. The development reagent can include a labeled streptavidin molecule that is capable of binding to DNA molecules attached to well bottoms that have incorporated the blocked nucleotide analog. The label on the streptavidin molecule can be any of a variety known in the art including, but not limited to a fluorescent label or horse radish peroxidase (HRP). The plate can be washed again to remove unbound labeled streptavidin molecules. The label can then be detected using a multiwell plate reader that detects, for example, fluorescence from a fluorescent label or absorption from a product of an HRP reaction (carried out using commercially available or otherwise known protocols). The presence of signal from the labeled streptavidin will be indicative of a polymerase having the ability to incorporate a nucleotide analog having a 3' attached phosphate blocking moiety. The same assay can be used to determine kinetics or other quantitative parameters by varying the reaction time and or concentration of liquid-phase reagents. Similar screen can be carried out for nucleotide analogs having other blocking moieties by minor modification of the reagents exemplified above.

Polymerases having the ability to incorporate a nucleotide analog of a particular structure can also be identified using a directed evolution approach. For example, the following microdroplet emulsion screen can be used. A polymerase gene library can be made containing a T7 promoter, ribosome binding site and T7 terminator (or stop codon). The polymerase genes in the library can then be manipulated to contain a 5' overhang at each end which is to be the incorporation site for one or more target nucleotide analogs in a subsequent screening step. For example, the overhang can be produced with restriction enzymes or T4 DNA polymerase exonuclease activity. An emulsion can be formed under conditions to form individual droplets having a single mutant polymerase gene together with a known deblocking agent, the target nucleotide analog(s) and components of a cell-free transcription/translation system (e.g. the PURexpress® system available from New England Biolabs, Ipswich, Mass.). Expression of an encoding polymerase able to incorporate the target nucleotide(s) would result in the overhangs being filled in on the encoding polymerase gene. Genes having filled in overhangs can then be identified based on any of a variety of known techniques including, for example, binding to primers specific for the presence of filled in overhangs. The primers can be PCR primers and droplets having filled in genes can be identified via amplification using those primers in a PCR reaction (i.e. only polymerases with activity towards the target nucleotide(s) would be amplified).

Although the above screen is exemplified in the context of in vitro protein synthesis system (PURexpress®), a library of polymerases (or other proteins to be screened can be obtained using other known methods. For example a library of polymerase mutant genes can be made within an encoding vector that is transformed into *E. coli* so that each *E. coli* cell contains one representative of the library or less. A water in oil emulsion can then be made such that each droplet contains one or less *E. coli* cell. The emulsion droplet can also include other components of the reaction under test such as a blocked nucleotide (e.g. a phosphodiester blocked nucleotide), a short patch primer that can bind to the polymerase encoding plasmid weakly and a deblocking enzyme (e.g. an endonuclease IV protein). The *E. coli* can be incubated for a sufficient time to express the vector encoding the mutant polymerase within each emulsion droplet. The emulsion droplet can then be treated to lyse the *E. coli* cells and thus release the cell contents into the emulsion droplet. In some embodiments, the *E. coli* cell could be heated to 95° C. to inactive the *E. coli* enzymes while the thermostable mutant polymerase species under test would remain active. The heat treatment conditions and/or deblocking enzyme can be selected such that the deblocking enzyme survives the heat treatment step. For example Tth endo IV is thermostable and thus particularly useful in this type of screening format. The weakly binding primer can then bind to the released encoding plasmid and the expressed mutant polymerase would attempt to incorporate the blocked nucleotide within the emulsion droplet. If incorporation were successful then the deblocking enzyme would unblock the DNA and enable further blocked nucleotide to be incorporated (e.g. second, third, fourth etc. nucleotides). After sufficient time for multiple nucleotide incorporations the emulsion can be burst. Plasmid with weakly bound primer can be selected. For example, selection can use a tag on the initial primer and use temperature to eliminate plasmids bound to unextended shorter primers. When incorporation has occurred the tagged primer can bind the plasmid more tightly to allow selection of plasmids encoding active polymerases from plasmids encoding inactive polymerases. Alternatively a tag on the nucleotide analogs can be used to select plasmids with tagged primer bound. Selecting for the primer bound to the encoding plasmid by either method maintains a physical link between catalytic activity and encoding DNA. Several rounds of selection can be carried out to optimize activity as desired.

A directed evolution technique, such as the microdroplet emulsion systems set forth above, can be used to screen for polymerase variants having specificity for any of a variety of nucleotide analogs. For example, Pol217 variants can be screened for the ability to incorporate nucleotide analogs having 3' phosphodiester blocking groups into nucleic acids. Such directed evolution techniques can be used to screen variants of any of the polymerases set forth herein for activity toward any of the nucleotide analogs set forth herein.

Genetically encoded deblocking agents can also be selected using a directed evolution approach. For example a microdroplet system similar to the one exemplified above for polymerase selection can be used except a library of deblocking agent genes can be used in place of the polymerase gene library and a known polymerase can be added to the microdroplets instead of the known deblocking agent. In a particular example, the gene library can be a library of Endonuclease IV variants. The EndoIV variants can be screened for the ability to remove any of a variety of blocking groups from nucleic acids including but not limited to, phosphotriester blocking groups. In another example, a mixed gene library can be used containing, in one embodiment, both Endonuclease IV genes and Ada protein genes.

Directed evolution techniques are particularly useful for selecting deblocking agents that are specific for blocking moieties having a phosphate moiety. In such examples, the overhang on the deblocking agent gene can be at least two nucleotides long, and the incorporation position for the target nucleotide analog can occur at a location on the overhang such that deblocking is required to occur in order to achieve fill in of the overhang. Thus, only if the expressed Endonuclease IV (and/or optionally Ada protein) was active towards removing or modifying the phosphate moiety would the gene be amplified. In embodiments where a deblocking agent has multiple components (e.g. Endonuclease IV and Ada protein), variants of a single component can be screened in the presence of known species for the other component(s). For example, the screen can use a library of variants for the test component and an emulsion formed under conditions to form individual droplets having a single gene for the test component together with a known species of the other component(s).

It will be understood that the microdroplet emulsion screen, and variants of the screen, can be used to evaluate variants for any of a variety of components used in a method or reaction mix set forth herein. For example, a library of nucleotide analog variants can be screened instead of a variant gene library. The nucleotide analogs can vary in terms of the chemical structure of the blocking group, label moiety, label modifier moiety, and/or other moiety set forth herein. It will also be understood that the microdroplet emulsion screen, although exemplified in several cases above for selection among variants of a single type of component, can have multiple dimensions whereby two or more of the components are varied. For example, a screen can include a library of mutant polymerase genes and a library of nucleotide analogs having variant blocking moieties.

The function of the microdroplets in the above-described screen is to provide reaction vessels that separate individual test species from each and house sufficient reaction components to carry out the chemical steps of the screen. Microdroplets can be made from an emulsion using techniques known in the art such as those described in Dressman et al. *Proc. Natl. Acad. Sci. USA* 100, 8817-8822 (2003); U.S. Pat. App. Publ. Nos. 2005/0042648 A1; 2005/0079510 A1 and 2005/0130173 A1, and WO 05/010145, each of which is incorporated herein by reference. Directed evolution techniques, such as the screens set forth above, need not be carried out in microdroplets. Any of a variety of vessels can be used instead such as wells of a microtiter plate, hollow beads, tubes, solid substrates having individual compartments and the like. Individual expression colonies having proteins bound to individual locations on a surface (e.g. nitrocellulose) can also be used.

Several embodiments of the methods and compositions set forth herein are useful for determining the nucleotide sequence of one or more nucleic acids. Embodiments in which a multicycle reaction occurs and in which nucleotide incorporation in each cycle is detected are particularly useful for sequencing-by-synthesis. For example, a label moiety that is present on an extended primer during each cycle can be detected. The detection event can be correlated with the species of nucleotide analog that was added to the primer, for example, based on a unique signal that distinguishes that species of nucleotide from other species of nucleotides that are in a reaction mixture where the primer extension reaction occurs. As such a multicycle reaction will produce a series of signals that can be translated to a sequence of added nucleotides. The sequence of added nucleotides will be the sequence that is complementary to the template to which the extended primer is hybridized. The sequence of the template strand can be inferred from the sequence of nucleotides incorporated into the strand that is being extended. As such, determination of the sequence of one strand will be understood to include determination of the sequence of its complementary strand.

The amount and/or concentration of one or more reagents in a reaction mixture can be adjusted to control or influence the lifetime for a transient species in a method set forth herein. The transient species may be detected, for example in cases where the transient species is an extended primer having a blocking moiety and/or label moiety. For example, the concentration (or amount) of polymerases, nucleotide analogs or deblocking agents can be adjusted to provide a desired lifetime for a detectable extended primer species that is produced transiently in a sequencing-by-synthesis method. In a particular embodiment, the lifetime of the extended primer species can be increased by decreasing the concentration (or amount) of the deblocking agent, by decreasing the concentration (or amount) of nucleotide analogs, by increasing the concentration (or amount) of the polymerase, or by a combination thereof. In this way, the rate of data acquisition can be tuned to suit a particular sequencing method.

Other factors that can be adjusted to tune a reaction include the activity of a polymerase or deblocking agent, type of blocking moiety or label, temperature, or presence of cofactors, salts, protons (i.e. pH), detergents and the like. Exemplary activities of a polymerase that can be adjusted include, without limitation, the binding affinity for particular nucleotide analogs, the catalytic rate of primer extension using particular nucleotide analogs or the rate of dissociation from nucleic acids that have incorporated particular nucleotide analogs. Polymerases can be engineered to have a desired activity or selected from a variety of native sources based on the desired activity. In embodiments wherein the deblocking agent includes an enzyme, similar engineering or selection can be employed to identify species having a desired activity such as binding affinity for particular nucleotide analogs in the monomeric state (in many cases a low or undetectable binding affinity is desired), catalytic rate of deblocking particular nucleotide analogs in the monomeric state (in many cases a low or undetectable catalytic rate is desired), binding affinity for nucleic acids having particular nucleotide analogs and catalytic rate of deblocking nucleic acids having particular nucleotide analogs.

In particular embodiments, a reaction can be tuned such that a transient nucleic acid species having a blocking moiety, and optionally a label moiety, is present for at least 1 millisecond (msec) before a deblocking agent modifies the transient nucleic acid species to remove the blocking moiety. Depending upon the application of the methods the reaction can be tuned such that the transient nucleic acid species is present for at least 2 msec, 5 msec, 10 msec, 100 msec, 1 sec, 5 sec, 10 sec or longer. Alternatively or additionally, the reaction can be tuned such that the transient nucleic acid species is present for no more than 5 min, 1 min, 30 sec, or 1 sec or less before the deblocking agent modifies the transient nucleic acid species to remove the blocking moiety.

In several instances, various compositions and methods are described in this disclosure with reference to a single species of one or more reaction components. This is done for clarity of illustration and is not intended to be limiting (although single species can be used in some embodiments). Rather, the compositions and methods can include several species that have structures and functions exemplified for single species. For example, the methods set forth herein are useful for multiplex detection whereby the steps are carried out simultaneously for several different nucleic acids. Thus a method of synthesizing a polynucleotide can include the steps of (a) providing a mixture including a plurality of different nucleic acids (i.e. having different nucleotide sequences), a collection of different nucleotide analogs, a polymerase and a deblocking agent, and (b) allowing sequential addition of a plurality of the different nucleotides analogs to each of the nucleic acids to proceed via several reaction cycles in the mixture, wherein each reaction cycle includes the steps of (i) the polymerase adding a nucleotide analog to each of the nucleic acids to form a plurality of transient nucleic acid species each comprising a blocking moiety, and (ii) the deblocking agent modifying the transient nucleic acid species to remove the blocking moiety from each of the transient nucleic acid species.

A multiplex reaction can utilize a solid-phase support. A solid-phase support can be useful for separating individual reactions such that each can be interrogated separately or individually. For example, several different nucleic acids in a mixture can be attached to the solid-phase support. The nucleic acids can be attached to the solid-phase support in an array format. The solid support upon which (or within which) the nucleic acids are attached can be made from the materials set forth herein previously or otherwise known in the art. Detection can be carried out at ensemble or single molecule levels on an array. Ensemble level detection is detection that occurs in a way that a population of molecules is detected at each individual feature such that individual molecules at the feature are not distinguished from each other. Thus, ensemble detection provides an average signal from the molecules at the feature. For example, the feature can contain at least 10, 100 or 1000 nucleic acid molecules, all having the same nucleotide sequence. Alternatively, detection at a single molecule level includes detection that occurs in a way that individual nucleic acid molecules are individually resolved on the solid-phase support. Thus, single molecule detection provides a signal from an individual molecule that is distinguished from one or more signals that may arise from a population of molecules within which the individual molecule is present.

Various protocols can be used to generate an array of spatially immobilized nucleic acid features. For example, the features can be generated by emulsion PCR, or bridge PCR (Mitra & Church *Nucleic Acids Res.* 27, e34 (1999); Dressman et al. *Proc. Natl. Acad. Sci. USA* 100, 8817-8822 (2003); Adessi, C. et al. *Nucleic Acids Res.* 28, e87 (2000); Fedurco et al. *Nucleic Acids Res.* 34, e22 (2006), each of which is incorporated herein by reference).

In embodiments using emulsion PCR, an in vitro-constructed adaptor flanked shotgun library can be PCR amplified in a water-in-oil emulsion. The PCR is multi-template PCR, because only a single primer pair is used. One of the PCR primers is tethered to the surface (5'-attached) of micron-scale beads that are also included in the reaction. A low template concentration results in most bead-containing compartments having either zero or one template molecule present. In productive emulsion compartments (where both a bead and template molecule is present), PCR amplicons can be captured at the surface of the bead. After breaking the emulsion, beads bearing amplification products can be selectively enriched. Each clonally amplified bead will bear on its surface PCR products corresponding to amplification of a single molecule from the template library. Various embodiments of emulsion PCR methods that are useful are set forth in U.S. Pat. App. Publ. Nos. 2005/0042648 A1; 2005/0079510 A1 and 2005/0130173 A1, and WO 05/010145, each of which is incorporated herein by reference.

In embodiments using bridge PCR, also known as cluster formation, an in vitro-constructed adaptor-flanked shotgun library can be PCR amplified using primers coated on the surface of a substrate. The primers are attached at their 5' ends by a flexible linker. Amplification products originating from any given member of the template library remain locally tethered near the point of origin. At the conclusion of the PCR, each clonal cluster contains several copies of a single member of the template library. Various embodiments of bridge PCR methods that are useful are set forth in U.S. Pat. App. Publ. No. 2007/0128624 A1, WO 07/010,251, U.S. Pat. Nos. 6,090,592 and 5,641,658, each of which is incorporated herein by reference.

The methods set forth herein can make or use arrays having features at any of a variety of densities including, for example, at least about 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, or higher.

A method of sequencing a polynucleotide is provided. The method can include the steps of (a) providing a mixture comprising (i) a nucleic acid having a primer hybridized to a template, (ii) a collection of different nucleotide analogs, wherein each of the different nucleotide analogs has a different base moiety, a blocking moiety having a different label moiety, and a label-modifier moiety, each of the different label moieties being correlated with one of the different base moieties, (iii) a polymerase, and (iv) a deblocking agent; (b) carrying out a reaction cycle in the mixture wherein (i) the polymerase adds one of the different nucleotide analogs to the primer and removes the label-modifier from the one of the different nucleotide analogs, thereby forming an extended primer having the blocking moiety and the different label moiety from the one of the different nucleotide analogs, and (ii) the deblocking agent removes the blocking moiety and the different label moiety from the extended primer; (c) performing several repetitions of the reaction cycle in the mixture; (d) detecting the label moiety that is on the extended primer during the repetitions of the reaction cycle.

Figure 1:
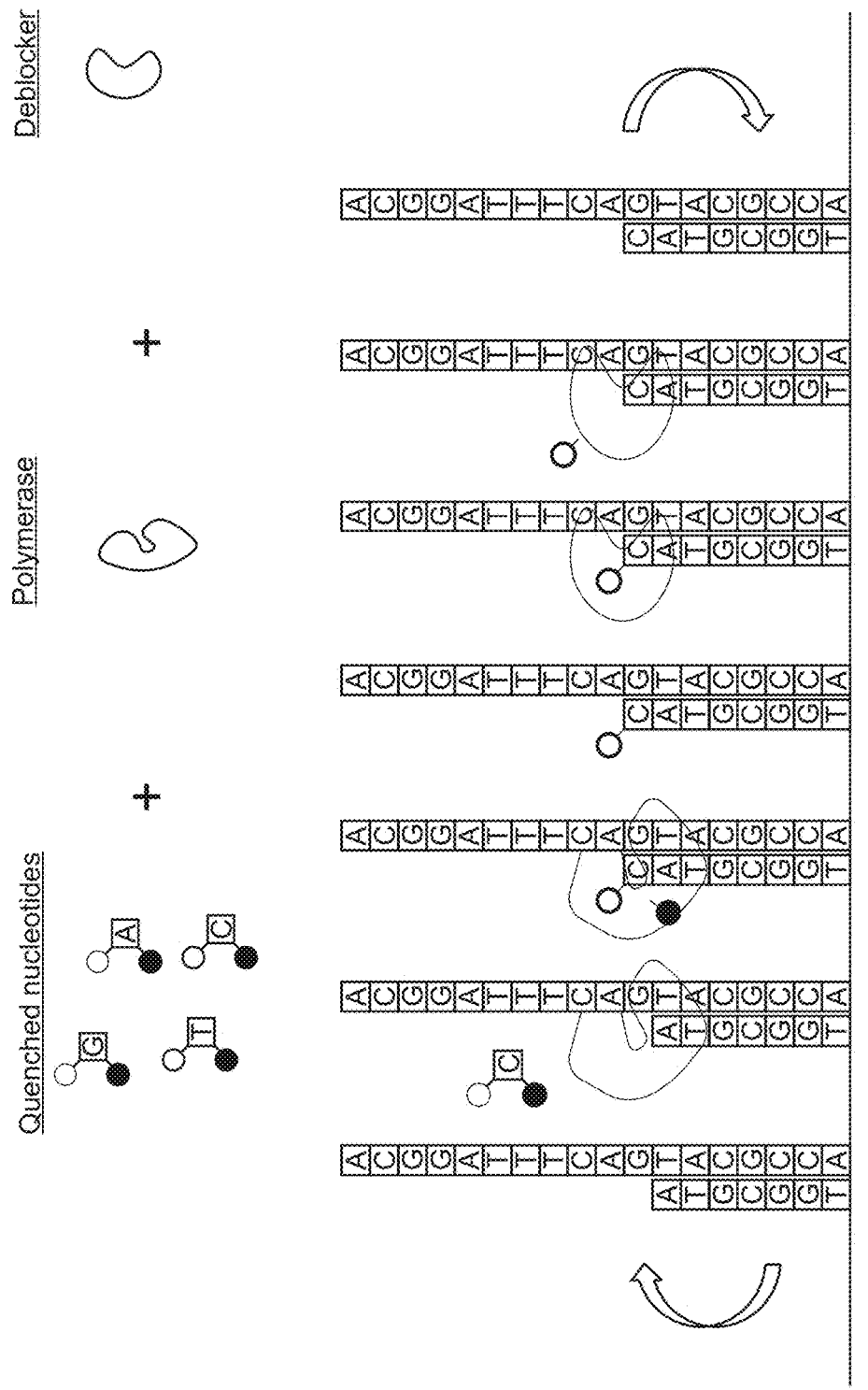
FIG. 1 shows a diagrammatic representation of a reaction cycle in which a polymerase catalyzes addition of a nucleotide analog to a primer and removal of a quenching moiety, followed by a deblocking agent catalyzing removal of a labeled blocking moiety from the nucleotide that was added to the primer.

A diagrammatic representation of a reaction cycle that can occur in a sequencing method is shown in FIG. 1. In that embodiment, the reaction mixture includes four different nucleotide analogs (dGTP, dATP, dTTP and dCTP analogs)

each having a unique fluorescent label, a quencher and a blocking moiety. In the monomeric form the fluorescent labels are quenched such that fluorescent signal is not detected. The reaction mixture also includes a polymerase and a deblocking agent. The mixture further includes a nucleic acid having a primer strand annealed to a template strand. In the figure the nucleic acid is shown in 7 different states representing various steps in the exemplary reaction cycle. In the first step, the polymerase binds to the nucleic acid. Then the polymerase adds a dCTP analog to the primer and removes the quencher, thereby forming an extended primer having the blocking moiety and the fluorescent label. As shown, the dCTP nucleotide analog is added to the primer at the position that complements a G base in the template strand. Removal of the quencher renders the fluorescent label capable of producing fluorescence emission when excited by an appropriate wavelength of light. In the next exemplary step, the polymerase dissociates from the nucleic acid, the nucleic acid still including the extended primer having the blocking moiety and the fluorescent label. Then the deblocking agent binds to the extended primer to form a complex. In the next step shown, the bound deblocking agent removes the label moiety and blocking moiety from the extended primer. The deblocking agent then dissociates to render the nucleic acid available for a repeat of the cycle. It will be understood that the steps shown in the figure are provided for ease of explanation and are not intended to be limiting with regard to the mechanism of the reaction described or with regard to other embodiments of the invention.

FIG. 2 shows an extension and deblocking step carried out for an exemplary nucleotide analog. The nucleotide analog contains a deoxyribose moiety. A triphosphate moiety is attached at the 5' position of the deoxyribose moiety and a quencher (shown as an oval) is attached to the gamma phosphate of the triphosphate moiety. A phosphate moiety is shown attached to the 3' position of the deoxyribose moiety and a fluorescent label is attached to the phosphate moiety. The fluorescent label is shown as a star that has a thin outline to indicate the quenched state for the monomeric form of the nucleotide analog. As shown in FIG. 2, a polymerase catalyzes addition of the nucleotide analog to a primer and removal of the quencher via pyrophosphate release. Removal of the quencher allows the label moiety to become fluorescent as indicated by the bold outline for the star in the figure. Thus, the polymerase produces a transient primer extension product having a phosphate blocking moiety and fluorescent label at the 3' end. Subsequently a phosphatase reacts with the transient product to remove the blocking moiety and label moiety. The extended primer is then ready for another cycle of nucleotide addition and deblocking.

In a particular embodiment, a primer extension reaction can include the steps of (a) providing a mixture including a nucleic acid, a collection of different nucleotide analogs, a polymerase and a deblocking agent, wherein the nucleotide analogs have a pentose moiety and a phosphodiester blocking moiety is attached at the 3' position of the pentose moiety; and (b) allowing sequential addition of a plurality of the different nucleotides analogs to the nucleic acid to proceed via several reaction cycles in the mixture, wherein each reaction cycle includes the steps of (i) the polymerase adding a nucleotide analog to the nucleic acid to form a transient nucleic acid species comprising a phosphodiester blocking moiety, and (ii) the deblocking agent modifying the transient nucleic acid species to remove the phosphodiester blocking moiety. The deblocking agent can be, for example, EndoIV or other enzyme that is capable of specifically removing the phosphodiester moiety from the 3' end of a nucleic acid. The polymerase can be an engineered variant of Pol217 or other polymerase that is capable of incorporating nucleotide analogs having a phosphodiester blocking moiety. The nucleotide analogs can optionally have a label moiety and/or a label modifier moiety. The label moiety and/or a label modifier moiety can be attached to the nucleotide analogs at any of a variety of positions such as those exemplified elsewhere herein. Furthermore the label moiety and/or a label modifier moiety can have any of a variety of structures or characteristics, including, but not limited to those set forth elsewhere herein. Accordingly, this primer extension reaction can be used in a method of sequencing a template strand in the nucleic acid that is extended.

Alternatively, a primer extension reaction can include the steps of (a) providing a mixture including a nucleic acid, a collection of different nucleotide analogs, a polymerase and a deblocking agent, wherein the nucleotide analogs have a pentose moiety and a phosphotriester blocking moiety is attached at the 3' position of the pentose moiety; and (b) allowing sequential addition of a plurality of the different nucleotides analogs to the nucleic acid to proceed via several reaction cycles in the mixture, wherein each reaction cycle includes the steps of (i) the polymerase adding a nucleotide analog to the nucleic acid to form a transient nucleic acid species comprising a phosphotriester blocking moiety, and (ii) the deblocking agent modifying the transient nucleic acid species to remove the phosphotriester blocking moiety. The deblocking agent can be, for example, an engineered variant of EndoIV or other enzyme that is capable of specifically removing the phosphotriester moiety from the 3' end of a nucleic acid. The polymerase can be, for example, Pol217 or other polymerase that is capable of incorporating nucleotide analogs having a phosphotriester blocking moiety. The nucleotide analogs can optionally have a label moiety and/or a label modifier moiety. The label moiety and/or a label modifier moiety can be attached to the nucleotide analogs at any of a variety of positions such as those exemplified elsewhere herein. Furthermore the label moiety and/or a label modifier moiety can have any of a variety of structures or characteristics, including, but not limited to those set forth elsewhere herein. Accordingly, this primer extension reaction can be used in a method of sequencing a template strand in the nucleic acid that is extended.

This disclosure further provides a method of synthesizing a polynucleotide that includes the steps of (a) providing a mixture including a nucleic acid, a collection of different nucleotide analogs, a polymerase, a phosphotriesterase and a phosphodiesterase, wherein the different nucleotide analogs each have a phosphotriester blocking moiety, and (b) sequentially adding a plurality of the different nucleotides analogs to the nucleic acid by several reaction cycles in the mixture, wherein each reaction cycle includes: (i) the polymerase adding a nucleotide analog to the nucleic acid to form a transient nucleic acid species having a phosphotriester blocking moiety, (ii) the phosphotriesterase converting the phosphotriester blocking moiety to a phosphodiester blocking moiety, and (iii) the phosphodiesterase removing the blocking moiety from the nucleic acid.

Figure 3:
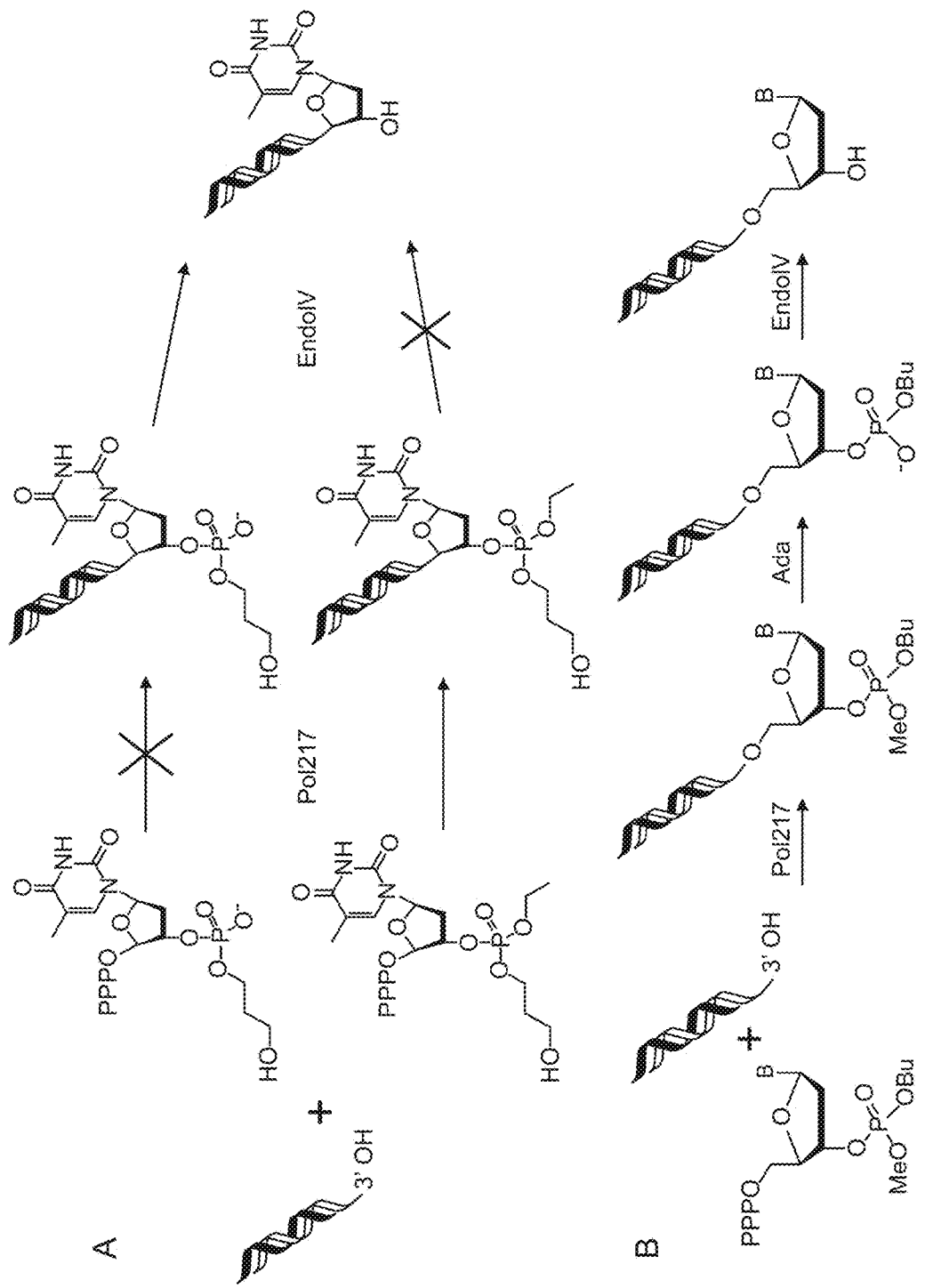
FIG. 3 shows a diagrammatic representation of selective reactions carried out by Pol217 and Endonuclease IV (Panel A, where an "X" through an arrow indicates inefficient or null reaction) and a reaction cycle in which Pol217 catalyzes extension of a primer to incorporate a nucleotide analog having a phosphotriester blocking moiety, Ada catalyzes conversion of the phosphotriester blocking moiety on the extended primer to a phosphodiester, and Endonuclease IV catalyzes the removal of the phosphodiester blocking moiety from the extended primer (Panel B).

An exemplary method that uses phosphotriester and phosphodiester blocking moieties is shown in FIG. 3. Panel A of the figure shows that the Pol217 polymerase extended a primer to incorporate a nucleotide analog having a phosphotriester blocking moiety at the 3' position of the nucleotide analog. However, as indicated by the arrow with the X through it, Pol217 does not efficiently incorporate a nucleotide analog having a phosphodiester blocking moiety at the 3' position in the exemplary method. Panel A of the figure also shows that Endonuclease IV removes a phosphotriester blocking moiety from the 3' position of a nucleic acid. However, as indicated by the arrow with the X through it, Endonuclease IV does not efficiently remove a phosphodiester blocking moiety from the 3' position of the nucleic acid in the exemplary method.

As shown in Panel B of FIG. 3, a reaction cycle can be built around selective activities of the Pol217 polymerase and Endonuclease IV. Specifically, the reaction cycle can have a step wherein Pol217 extends a primer to incorporate a nucleotide analog having a phosphotriester blocking moiety at the 3' position. The phosphotriester blocking moiety at the 3' position of the extended primer can be converted to a phosphodiester, for example, via the activity of the Ada protein. Then the phosphodiester blocking moiety at the 3' position of the extended primer can be removed by Endonuclease IV, thereby rendering the extended primer capable of being used in a subsequent reaction cycle. This is one example of a reaction cycle that uses a deblocking agent that is composed of several components. Deblocking agents that have several components can be used generally as exemplified elsewhere herein with regard to deblocking agents having a single component. An advantage of a multicomponent deblocking agent is that each of the individual components can provide a target for tuning of a multistep reaction. For example, in the case of the embodiment shown in FIG. 3, the concentration (or amount) of the Ada protein, Endonuclease IV or both can be decreased to increase the lifetime for a transient nucleic acid species having a blocking moiety and, optionally, a label moiety.

It will be understood that the activity of the Ada protein illustrated in FIG. 3, is identified as a phosphotriesterase activity. However, the activity may also be characterized as an alkyltransferase or even a methyltransferase activity. Any agent that is capable of converting the phosphotriester blocking moiety at the 3' position of the extended primer to a phosphodiester can be used and for the purposes of this disclosure will be considered to be a phosphotriesterase (independent of the mechanism underlying the conversion). Furthermore, any agent that is capable of removing the phosphodiester blocking moiety from the 3' position of the extended primer can be used independent of the mechanism employed. Also, the Pol217 polymerase is exemplary and can be replaced using another polymerase having a similar selectivity.

Although FIG. 3 demonstrates the use of phosphotriester and phosphodiester blocking moieties in nucleotide moieties that do not have an exogenous label moiety, it will be understood that a detection step can be used. For example, the nucleotide analog exemplified in the figure can include an exogenous label moiety that is detected or an endogenous label can be detected. Furthermore, the nucleotide analog can have a label-modifier moiety.

Accordingly a method of sequencing a polynucleotide is provided which can include the steps of (a) providing a mixture including (i) a nucleic acid having a primer hybridized to a template, (ii) a collection of different nucleotide analogs, wherein each of the different nucleotide analogs has a different base moiety, and a phosphotriester blocking moiety having a different label moiety, each of the different label moieties being correlated with one of the different base moieties, (iii) a polymerase, (iv) a phosphotriesterase, and (v) a phosphodiesterase; (b) carrying out a reaction cycle in the mixture wherein (i) the polymerase adds one of the different nucleotide analogs to the primer, thereby forming an extended primer having the phosphotriester blocking moiety and the different label moiety from the one of the different nucleotide analogs, (ii) the phosphotriesterase converts the phosphotriester blocking moiety to a phosphodiester blocking moiety, and (iii) the phosphodiesterase removes the phosphodiester blocking moiety and the different label moiety from the extended primer; (c) performing several repetitions of the reaction cycle in the mixture; and (d) detecting the label moiety that is on the extended primer during the repetitions of the reaction cycle. Optionally, the nucleotide analog can also include a label-modifier moiety and the polymerase can remove the label-modifier from one of the different nucleotide analogs that it adds to the primer.

Figure 4:
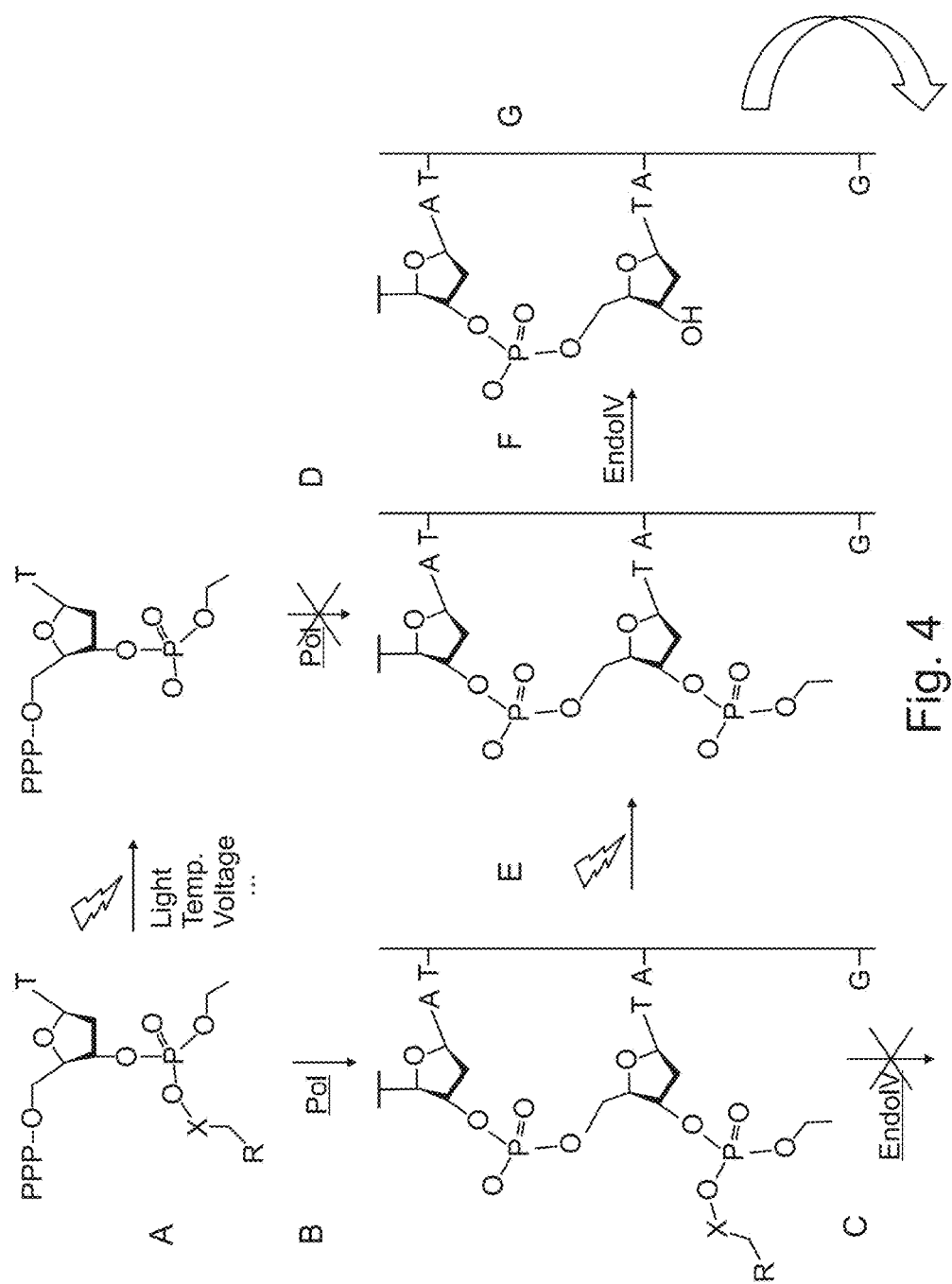
FIG. 4 shows a diagrammatic representation of a reaction cycle in which polymerase catalyzes extension of a primer to incorporate a caged nucleotide analog having a phosphotriester blocking moiety with a labile phosphoester bond, a physical stimulus removes the labile phosphoester bond to convert the blocking moiety to a phosphodiester form and Endonuclease IV catalyzes the removal of the phosphodiester blocking moiety from the nucleotide analog when incorporated into the extended primer. Reactions that do not occur efficiently are indicated by an "X" through an arrow.

FIG. 4 shows another reaction cycle that can be built around selective activities of the Pol217 polymerase and Endonuclease IV. As shown the reaction mixture can include a nucleotide analog having a caged phosphotriester blocking moiety in which one of the ester bonds is cleavable by a physical stimulus (e.g. light, temperature change or voltage). Pol217 can add the nucleotide analog to a primer to form a transient extended primer having the caged phosphotriester blocking moiety. Because Endonuclease IV is incapable of removing the caged phosphotriester blocking moiety from the extended primer, the transient species will remain until the phosphotriester is uncaged using the physical stimulus to convert it to a phosphodiester. The phosphodiester blocking moiety can then be removed from the extended primer by Endonuclease IV to return the primer to a form that is ready for another cycle. As shown in FIG. 4, in the event that a monomeric nucleotide analog in the reaction mixture receives the physical stimulus, the caged phosphotriester blocking moiety may be converted to the uncaged phosphodiester form. However, because monomeric nucleotide analogs having phosphodiester blocking moieties are not incorporated into the primer by Pol217, the conversion will not cause unwanted incorporation of uncaged nucleotide analogs into the primer.

More generally, the example shown in FIG. 4 and described above demonstrates the use of a caged nucleotide analog and the use of a physical stimulus to uncage the nucleotide analog. This approach can be particularly useful for embodiments where relatively rapid conversion steps are desired or where synchronized initiation of a reaction is desired. For example, uncaging with a physical stimulus can be used in conjunction with fluorescence lifetime imaging (FLIM) detection to reduce or eliminate the occurrence of incorporation and/or deblocking events that are too fast to detect.

It will be understood that conversion of caged monomeric nucleotides to an uncaged form although not necessarily detrimental for the reasons set forth above, may nevertheless be undesirable. For example, conversion of caged monomeric nucleotide analogs may result in depletion of the pool of nucleotide analogs available for subsequent cycles of primer extension. This can be mitigated by periodically delivering caged monomeric nucleotides to the reaction mixture. Additionally or alternatively, the uncaging physical stimulus can be delivered to an extended primer species in a focused or selective manner such that a pool of caged monomeric nucleotides elsewhere in the reaction mixture is not impacted. Methods such as confocal delivery of light and/or physical confinement of extended primer species can be used, for example, as set forth above in regard to focused and selective detection methods.

As illustrated by the example of FIG. 4, the phosphotriester moiety can have a linker (identified as "x" in the figure)

that is cleavable by the physical stimulus. A label moiety, indicated as "R" in the figure, can optionally be attached to linker "x." Further examples of caged nucleotide analogs are shown in FIG. 5. Panel A of FIG. 5 shows an example of a nucleotide analog having a phosphotriester blocking moiety with a photo-labile ester bond. Panel B of the Figure shows an example of a nucleotide analog having a phosphotriester blocking moiety with a thermo-labile ester bond. In both examples, the "R" moiety indicates that a label moiety can be attached to the labile linker. The "Q" moiety indicates that a label-modifier moiety can be attached to the triphosphate at the 5' position of the pentose moiety. It will be understood that the positions shown for the "R" and "Q" moieties are exemplary. These moieties can be located at other positions in a caged nucleotide analog having photo- or thermo-labile linkages.

The use of physical stimuli to uncage reaction components is particularly useful for embodiments that use single molecule detection methods. Single molecule reactions are stochastic by nature. Gating with physical stimuli can provide for temporal control of detection to coincide with initiation of the single molecule reaction thereby providing more accurate detection. Gating techniques are also useful for ensemble-level detection. For example, whether used for a single-molecule or ensemble level embodiments, gating can provide spatial control of a reaction. More specifically, a sample can contain a relatively large number of nucleic acids and focused light can be delivered to a portion of the sample to activate a sub-population of the nucleic acids.

Generally a reaction mixture will contain a collection of at least four different nucleotide analogs, wherein each of the different nucleotide analogs has a different base moiety and each also has a blocking moiety. The nucleotides in the mixture can optionally have a different label moiety, each of the different label moieties being correlated with one of the different base moieties. Alternatively or additionally, the nucleotides in the mixture can optionally have a label-modifier moiety. In some embodiments, a reaction mixture can include no more than four, three, two or one of the different nucleotide analog types. Accordingly, a method that uses fewer than four types of nucleotide analogs may be used to produce a low resolution sequence in which fewer than all four of the nucleotide types in a nucleic acid are determined. A low resolution sequence can provide a useful scaffold for sequence alignment as set forth in U.S. Patent Publ. Nos. 2010/0173303 A1 and 2010/0279882 A1, each of which is incorporated herein by reference. If desired, a sequencing method that uses fewer than all four of the nucleotide types can be repeated for the same target nucleic acid(s) (e.g. repeated on the same array) using a different set of nucleotide types (i.e. different bases can be represented in the two different sets of nucleotide analogs). Multiple low resolution sequences can be obtained in this way and combined to arrive at a high resolution sequence for the nucleic acid(s).

Various embodiments of the methods and compositions of the present invention have been exemplified with respect to primer extension using polymerases and monomeric nucleotide analogs. However, primer extension can also result in addition of an oligonucleotide to a primer, for example via the activity of a ligase enzyme. The oligonucleotide can include a blocking moiety, label moiety and label-modifier moiety such as those exemplified herein with respect to monomeric nucleotide analogs. Those skilled in the art will recognize that certain aspects may differ for embodiments utilizing oligonucleotides. For example, an oligonucleotide can be ligated to either the 5' or 3' end of a primer. As such a blocking moiety can be present on the 5' end of an oligonucleotide or on the 3' end of the oligonucleotide.

Sequencing-by-ligation can be performed using the primer extension methods of the present disclosure. In such embodiments, a reaction mixture can include a mixed pool of probe oligonucleotides (e.g. each about eight or nine bases long). The pool of probe oligonucleotides can contain 4 subsets each corresponding to one of four nucleotides that are present at a target position in the oligonucleotides. Each subset can have a specific label moiety that is correlated with the identity of the nucleotide at the target position. The nucleotides at the other positions of the oligonucleotide are generally degenerate. The oligonucleotides in each subset can also have a blocking moiety and a label-modifier moiety. In a sequencing-by-ligation reaction cycle, an appropriately complementary oligonucleotide can hybridize to a template nucleic acid next to a primer, and DNA ligase can join the oligonucleotide to the primer. This will form a transient primer extension product (i.e. ligation product) having a blocking moiety at the opposite end from the end that ligates to the primer, and a label moiety. The label moiety can be detected under conditions that distinguish the extended primer from oligonucleotides that have not been ligated to the primer. For example, the species can be distinguished based on the absence of the label-modifier moiety in the extended primer or by a focused detection method. Based on the signal produced by the oligonucleotide, the identity of the nucleotide at the target position can be determined. The deblocking agent can then be removed by the action of the deblocking agent to return the primer to a form that is reactive in a subsequent sequencing-by-ligation cycle. This is a brief example of a sequencing-by-ligation embodiment. Exemplary sequencing-by-ligation systems and methods that can be modified to incorporate the methods and compositions described herein are described in U.S. Pat. Nos. 6,969,488, 6,172,218, and 6,306,597, the disclosures of which are incorporated herein by reference.

A sequencing reaction or other reaction that produces a detectable species can be observed using an appropriate detection device. For example, optical detection can be carried out on a device having a camera. The camera can be based upon any suitable technology, such as those including a charge coupled device (CCD) or a complementary metal-oxide-semiconductor (CMOS). In particular embodiments a CMOS imager having a single-photon avalanche diode (CMOS-SPAD) can be used, for example, to distinguish fluorophores using fluorescence lifetime imaging (FLIM). Exemplary CMOS based systems that can be used for FLIM are described in US Pat. App. Publ. No. 2008/0037008 A1; Giraud et al., *Biomedical Optics Express* 1: 1302-1308 (2010); or Stoppa et al., IEEE European Solid-State Device Conference (ESSCIRC), Athens, Greece, IEEE, pp. 204-207 (2009), each of which is incorporated herein by reference. Other useful detection devices that can be used include, for example, those described in U.S. Pat. No. 7,329,860 and US Pat. App. Publ. No. 2010/0111768 A1, each of which is incorporated herein by reference. In addition, it will be appreciated that other signal detecting devices as known in the art can be used to detect signals produced in a method set forth herein.

The present disclosure provides reaction mixtures that include various combinations of the components that are set forth herein. In several cases reaction components and several combinations of the components are described in the context of exemplary methods. It will be understood that the reaction mixtures and the components thereof need not be limited to use in the methods exemplified herein. Other uses are contemplated as well.

In a particular embodiment, this disclosure provides a reaction mixture that includes (a) a nucleic acid having a primer hybridized to a template, (b) a nucleotide analog, wherein the nucleotide analog has a blocking moiety; (c) a polymerase that is capable of forming an extended primer by adding the nucleotide analog to the primer, and (d) a deblocking agent that is capable of removing the blocking moiety from the extended primer. Optionally, the nucleotide analog can further include a label moiety. The label moiety can be attached to the blocking moiety in some cases. Whether or not the label moiety is attached to the blocking moiety, the nucleotide analog can further include a label-modifier moiety. The polymerase can optionally be capable of removing the label-modifier from the nucleotide analog that is added to the primer.

In an exemplary embodiment, a reaction mixture can include (a) a nucleic acid having a primer hybridized to a template, (b) a collection of at least four different nucleotide analogs, wherein each of the different nucleotide analogs has a different base moiety and a blocking moiety, (c) a polymerase that is capable of forming an extended primer by adding at least one of the different nucleotide analogs to the primer, and (d) a deblocking agent that is capable of removing the blocking moiety from the extended primer. Optionally, each of the nucleotide analogs can further include a different label moiety, each of the different label moieties being correlated with one of the different base moieties. One or more of the label moieties can be attached to the blocking moiety of the respective nucleotide analog. One or more of the nucleotide analogs can further include a label-modifier moiety, and this can be the case whether or not the label moiety is attached to the blocking moiety of the respective nucleotide analog(s). The polymerase can optionally be capable of removing the label-modifier(s) from the nucleotide analog(s) that are added to the primer.

Accordingly, a reaction mixture can include (a) a nucleic acid having a primer hybridized to a template, (b) a collection of at least four different nucleotide analogs, wherein each of the different nucleotide analogs has a different base moiety, a blocking moiety having a different label moiety, and a label-modifier moiety, each of the different label moieties being correlated with one of the different base moieties, (c) a polymerase that is capable of forming an extended primer by adding at least one of the different nucleotide analogs to the primer and removing the label-modifier from the at least one of the different nucleotides that is added to the primer, and (d) a deblocking agent that is capable of removing the blocking moiety from the extended primer.

The reaction mixtures set forth in the preceding paragraphs include several components for which exemplary species are set forth elsewhere herein. It will be understood that those species can be included in the reaction mixtures in various combinations. For example, a blocking moiety can be a phosphotriester moiety and the deblocking agent can include a phosphotriesterase and a phosphodiesterase. Accordingly, a reaction mixture can includes (a) a nucleic acid having a primer hybridized to a template, (b) a nucleotide analog, wherein the nucleotide analog has a phosphotriester blocking moiety; (c) a polymerase that is capable of forming an extended primer by adding the nucleotide analog to the primer, and (d) a deblocking agent that is capable of removing the blocking moiety from the extended primer, wherein the deblocking agent includes a phosphotriesterase and a phosphodiesterase. Optionally, the nucleotide analog can further include a label moiety. The label moiety can be attached to the phosphotriester blocking moiety in some cases. Whether or not the label moiety is attached to the phosphotriester blocking moiety, the nucleotide analog can further include a label-modifier moiety. The polymerase can optionally be capable of removing the label-modifier from the nucleotide analog that is added to the primer.

In a further example where a phosphotriester blocking moiety is used, a reaction mixture can include (a) a nucleic acid having a primer hybridized to a template, (b) a collection of at least four different nucleotide analogs, wherein each of the different nucleotide analogs has a different base moiety and a phosphotriester blocking moiety, (c) a polymerase that is capable of forming an extended primer by adding at least one of the different nucleotide analogs to the primer, and (d) a deblocking agent that is capable of removing the phosphotriester blocking moiety from the extended primer, wherein the deblocking agent includes a phosphotriesterase and a phosphodiesterase. Optionally, each of the nucleotide analogs can further include a different label moiety, each of the different label moieties being correlated with one of the different base moieties. One or more of the label moieties can be attached to the phosphotriester blocking moiety of the respective nucleotide analog. One or more of the nucleotide analogs can further include a label-modifier moiety, and this can be the case whether or not the label moiety is attached to the phosphotriester blocking moiety of the respective nucleotide analog(s). The polymerase can optionally be capable of removing the label-modifier(s) from the nucleotide analog(s) that are added to the primer.

In particular embodiments, a blocking moiety can be a phosphodiester moiety and the deblocking agent can include a phosphodiesterase. Accordingly, a reaction mixture can includes (a) a nucleic acid having a primer hybridized to a template, (b) a nucleotide analog, wherein the nucleotide analog has a phosphodiester blocking moiety; (c) a polymerase that is capable of forming an extended primer by adding the nucleotide analog to the primer, and (d) a deblocking agent that is capable of removing the blocking moiety from the extended primer, wherein the deblocking agent includes a phosphodiesterase. Optionally, the nucleotide analog can further include a label moiety. The label moiety can be attached to the phosphodiester blocking moiety in some cases. Whether or not the label moiety is attached to the phosphodiester blocking moiety, the nucleotide analog can further include a label-modifier moiety. The polymerase can optionally be capable of removing the label-modifier from the nucleotide analog that is added to the primer.

In a further example where a phosphodiester blocking moiety is used, a reaction mixture can include (a) a nucleic acid having a primer hybridized to a template, (b) a collection of at least four different nucleotide analogs, wherein each of the different nucleotide analogs has a different base moiety and a phosphodiester blocking moiety, (c) a polymerase that is capable of forming an extended primer by adding at least one of the different nucleotide analogs to the primer, and (d) a deblocking agent that is capable of removing the phosphodiester blocking moiety from the extended primer, wherein the deblocking agent includes a phosphodiesterase. Optionally, each of the nucleotide analogs can further include a different label moiety, each of the different label moieties being correlated with one of the different base moieties. One or more of the label moieties can be attached to the phosphodiester blocking moiety of the respective nucleotide analog. One or more of the nucleotide analogs can further include a label-modifier moiety, and this can be the case whether or not the label moiety is attached to the phosphodiester blocking moiety of the respective nucleotide analog(s). The polymerase can optionally be capable of removing the label-modifier(s) from the nucleotide analog(s) that are added to the primer.

One or more of the components present in a reaction mixture set forth in the preceding paragraphs can be bound to a solid-phase substrate. For example, one or more of the nucleic acids can be present in one or more features of an array. In another example, the polymerase(s) and/or deblocking agents can be attached to a solid-phase substrate. The solid-phase substrate can be an array and as such a plurality of polymerases and/or deblocking agents can be present in one or more features of an array.

Various combinations of the components set forth above in regard to exemplary reaction mixtures and reaction methods can be provided in a kit form. Such a kit can include individual components that are separated from each other, for example, being carried in separate vessels or packages. A kit can include one or more sub-combinations of the components set forth herein, the one or more sub-combinations being separated from other components of the kit. The sub-combinations can be combinable to create a reaction mixture set forth herein (or combined to perform a reaction set forth herein). In particular embodiments, a sub-combination of components that is present in an individual vessel or package is insufficient to perform a reaction set forth herein. However, the kit as a whole can include a collection of vessels or packages the contents of which can be combined to perform a reaction set forth herein.

A kit can include a suitable packaging material to house the contents of the kit. The packaging material can be constructed by well known methods, preferably to provide a sterile, contaminant-free environment. The packaging materials employed herein can include, for example, those customarily utilized in commercial kits sold for use with nucleic acid sequencing systems. Exemplary packaging materials include, without limitation, glass, plastic, paper, foil, and the like, capable of holding within fixed limits a component set forth herein.

The packaging material can include a label which indicates a particular use for the components. The use for the kit that is indicated by the label can be one or more of the methods set forth herein as appropriate for the particular combination of components present in the kit. For example, a label can indicate that the kit is useful for a method of synthesizing a polynucleotide or for a method of determining the sequence of a nucleic acid.

Instructions for use of the packaged reagents or components can also be included in a kit. The instructions will typically include a tangible expression describing reaction parameters, such as the relative amounts of kit components and sample to be admixed, maintenance time periods for reagent/sample admixtures, temperature, buffer conditions, and the like.

It will be understood that not all components necessary for a particular reaction need be present in a particular kit. Rather one or more additional components can be provided from other sources. The instructions provided with a kit can identify the additional component(s) that are to be provided and where they can be obtained.

Example I

Substrate Specificity of Pol217 Polymerase and Endonuclease IV

This example demonstrates selective incorporation of a phosphodiester blocked nucleotide analog by Pol 217 polymerase. This example also demonstrates selective removal of a phosphodiester blocking moiety from a nucleic acid by Endonuclease IV.

Figure 6:
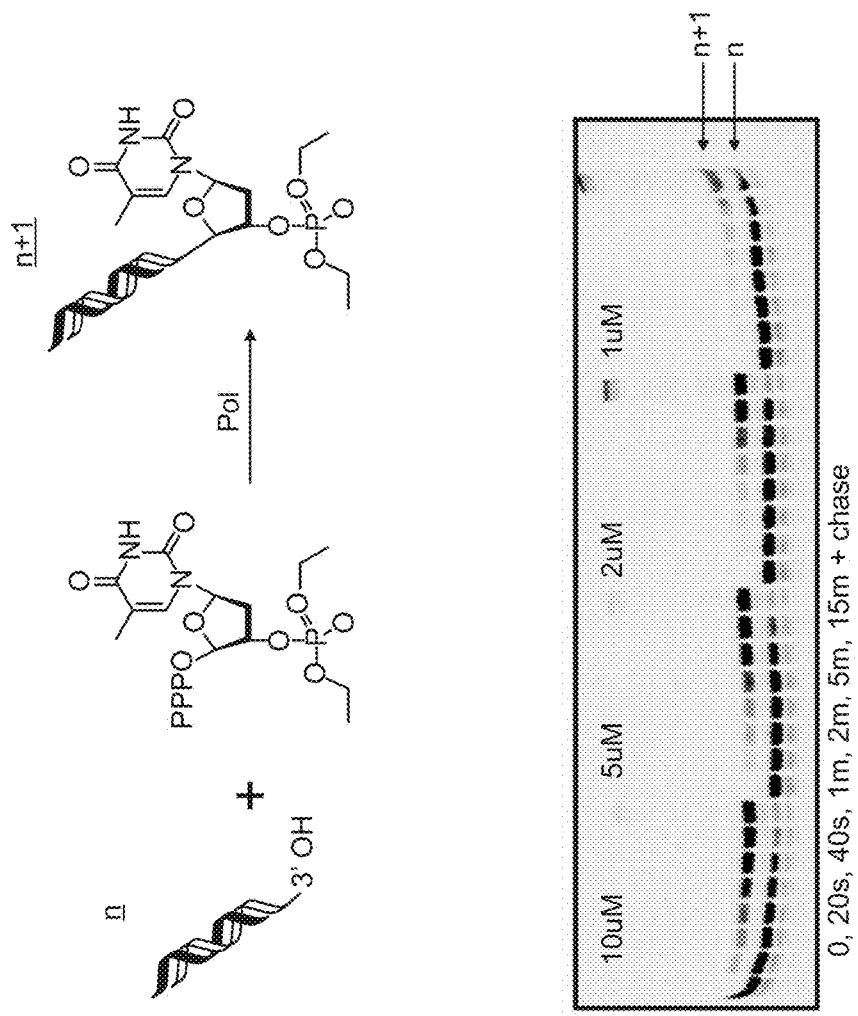
FIG. 6 shows data demonstrating activity of Pol217 for extending a primer to incorporate a nucleotide analog having a phosphotriester blocking moiety.

FIG. 6 includes a diagrammatic representation of the following reaction for Pol 217 catalyzed incorporation of pppT3'PO$_4$(Et)$_2$ into DNA. Pol 217 (15 µg/ml) was incubated at 30° C. in Pol buffer (50 mM TRIS pH 7.5, 0.05% Tween 20, 6 mM MgSO$_4$, 1 mM EDTA, 50 mM NaCl) with 20 nM DNA (P21 primer annealed to Diff template AG). A time zero aliquot was taken for each concentration and then pppT3'PO$_4$(EO$_2$ was added at 10, 5, 2 or 1 µM final concentration to start the reaction. Tubes are incubated at 30° C. and aliquots were taken at 0.33, 0.66, 1, 2, 5, and 15 mins from the 4 reaction tubes for quenching and 15% urea acrylamide gel analysis. 1 mM dNTPs were added to the remaining 4 reaction tubes and after a further 10 mins an aliquot was taken for gel analysis (chase).

A photograph of the gel resulting from the above polymerase extension reaction is shown in FIG. 6. Eight samples represent a time course for each reaction from 0, 0.33, 0.66, 1, 2, 5, 15 min and a final chase moving left to right. The results show the primer (lower band-n) changing into an n+1 band over the time course, with an increase in the amount of n+1 over time. The n+1 band demonstrates the addition of the pppT3'PO$_4$(Et)$_2$ nucleotide to the primer DNA (i.e. extension by one base). Following the addition of natural dNTPs the polymerase was unable to extend the primer to the end of the template demonstrating that addition of the pppT3'PO$_4$(Et)$_2$ creates a 3' blocked primer. The incorporation is more rapid at higher concentrations (10 µM) than at lower ones (1 µM) and shows time dependence indicative of genuine enzyme incorporation.

Bst, Vent exo- and Klenow polymerases were tested with pppT3'PO$_4$(Et)$_2$ or similar nucleotides and did not show any incorporation bands, except in the chase lane where the primer was copied to the end of the template illustrating that the polymerases were active, but not towards pppT3'PO$_4$(Et)$_2$ or the other similar nucleotides under the conditions tested.

Pol 217 was tested in Pol buffer at 55° C. (a higher temperature to increase chances of incorporation) with a range of phosphodiester blocked nucleotides at 10 µM including pppT3'PO$_4$PrOH (substantial incorporation was not observed), pppT3'PO$_4$Et (low level incorporation was observed), pppT 3'PO$_4$ (incorporation was observed but the band on the gel chased away indicating that the blocking group was not stable under the conditions tested) and pppT3'PO$_4$Cl$_2$ biotin (low level incorporation was observed when high concentrations of the nucleotide analog were used).

Figure 7:
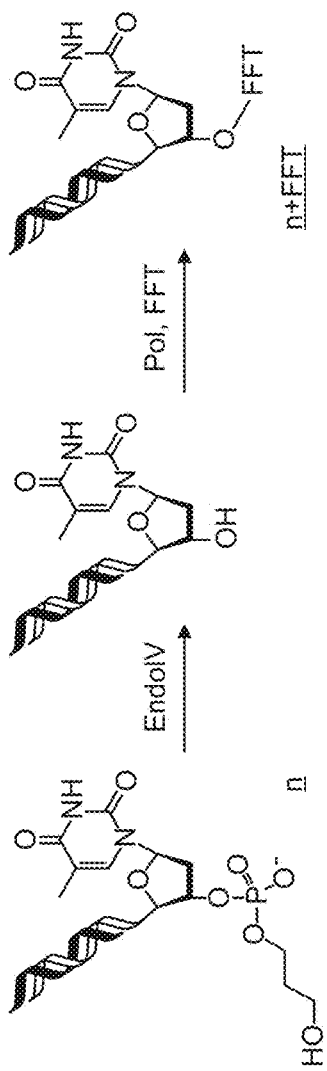
FIG. 7 shows data demonstrating activity of Endonuclease IV for removing a phosphodiester blocking moiety from a nucleic acid.
Figure 7:
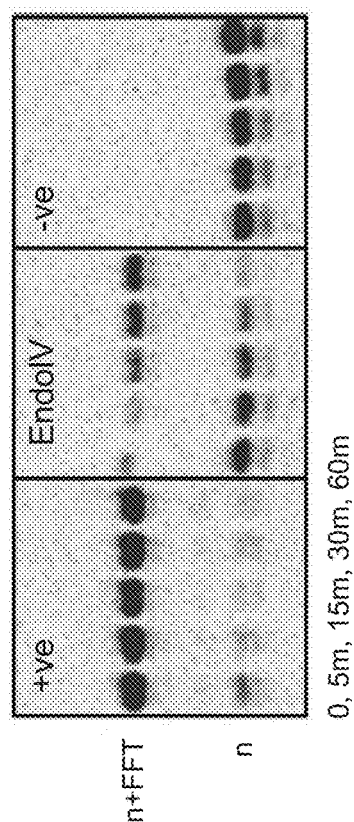

FIG. 7 includes a diagrammatic representation of the following reaction for selective removal of a 3' PO$_4$PrOH blocking moiety from a nucleic acid by E. coli Endonuclease IV. Primer DNA with either a 3' PO$_4$PrOH block (-ve and EndoIV) or a free 3'OH (+ve) was radiolabelled and bound to an A template strand. DNA was added to start the incubation at 55° C. in NEB buffer 3 (100 mM NaCl, 50 mM TRIS, 10 mM MgCl$_2$, 1 mM DTT pH 7.9) with Pol 217 (15 µg/ml), 10 µM FFT (reversibly blocked thymine triphosphate nucleotide, Illumina, Inc. San Diego, Calif.) and +/−EndoIV (0.1 U). Aliquots were removed at 0, 5, 15, 30 and 60 min for quenching and gel analysis (left to right respectively). "+ve" is the time course for unblocked DNA plus EndoIV, "EndoIV" is blocked DNA plus E. coli EndoIV and "−ve" is blocked DNA without E. coli EndoIV.

A photograph of the gel produced by the above deblocking reaction is shown in FIG. 7. The lower band is the unextended primer. The upper band is the primer after the addition of FFT to make an n+FFT extension species. It can be seen that on unblocked DNA (+ve) the addition of FFT to the DNA is almost instantaneous (even present in the time "0" sample ~5 seconds in reality). This shows that the polymerase works in the presence of EndoIV. For the −ve samples with 3' blocked DNA there was no incorporation of FFT as no visible unblocking of the primer resulted in the absence of EndoIV. This confirms the 3' block is stable in the conditions of the assay. With 3' blocked DNA and EndoIV (EndoIV) there was a gradual removal of the 3' block from the DNA as evidenced by a change to n+FFT (itself a very rapid step). Thus, as soon as the EndoIV works to unblock the DNA, the polymerase can add FFT to the free 3' end. This also demonstrates that both enzymes can share binding of the DNA and neither permanently competes out the other from binding the DNA.

APE1 and Tth Endonuclease (both from New England Biolabs, Ipswich, Mass.) were tested in similar assays. Neither of these demonstrated removal of the 3' $PO_4PrOH$ blocking moiety from a nucleic acid in a time and concentration dependent way under the conditions tested. In contrast, E. coli EndoIV followed time and concentration dependence for removal of the 3' $PO_4PrOH$ blocking moiety and for removal of several other 3' blocking moieties.

Similar reactions to those described above in the context of FIG. 7 were conducted, but the blocked extension products were generated using Pol 217 to incorporate various phosphotriester nucleotides onto the primer DNA. Incubation of the blocked primer DNA with large quantities of E. coli EndoIV at 37° C. or 55° C. failed to allow subsequent incorporation onto the primer DNA after extended incubation times under the conditions tested. Phosphotriester blocking moieties tested included pppT3'$PO_4$(Et)$_2$, pppT3'$PO_4$(Et)(Pr-Cap), pppT3'$PO_4$(Et)(PrOH), pppT3'$PO_4$MeBu and pppT3'$PO_4$(Et)(SSOH).

Figure 8:
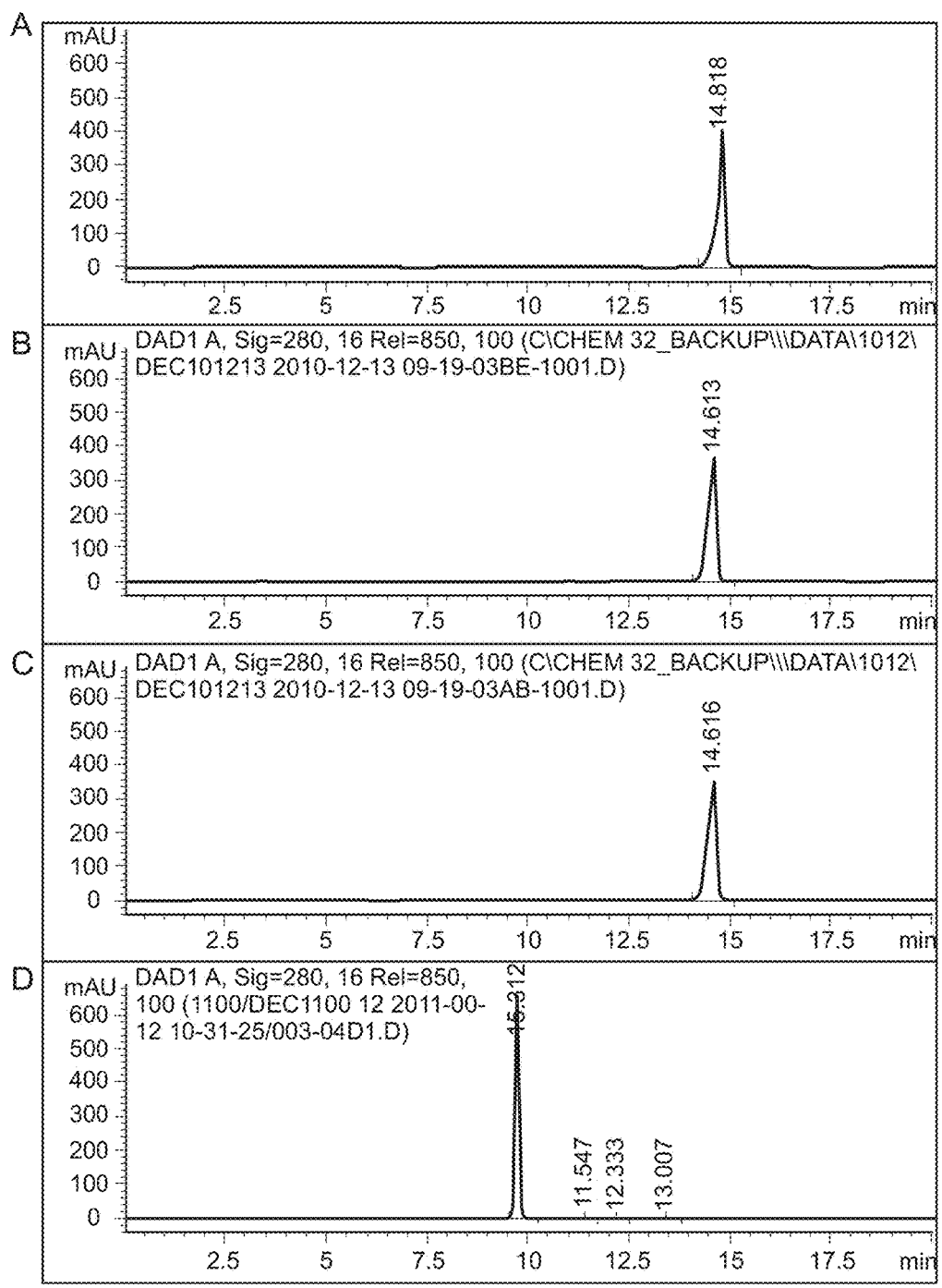
FIG. 8 shows HPLC chromatograms for a monomeric thymine nucleotide analog having a phosphodiester blocking moiety (A); for the monomeric nucleotide analog after incubation with EndoIV for 1.5 hours (B); for the monomeric nucleotide analog after incubation with EndoIV for 3 days (C) and for deoxythymine monophosphate (D).

FIG. 8 shows that EndoIV did not remove a 3' phosphodiester blocking moiety from a free nucleotide (i.e. a monomeric nucleotide analog). A solution of 0.1 mM 5' monophosphate T-3'$PO_4$Et (i.e. pT-3'$PO_4$Et) and 500 units/mL Endonuclease IV, 100 mM NaCl, 50 mM TrisCl, 10 mM $MgCl_2$, 1 mM DTT, pH=7.9 was incubated at 37° C. Aliquots were taken at set time points and analyzed by HPLC chromatography. The Figure shows the HPLC chromatograms of the mixture at time points: A) 0, B) 1.5 hours, and C) 3 days. Chromatogram D) shows the chromatogram of TMP indicating the expected retention time for deblocked pT-3'$PO_4$Et. No deblocked pT-3'$PO_4$Et was observed even after 3 days, indicating that EndoIV did not remove the 3' phosphate blocking moiety from the mononucleotide species. Comparison of the results for FIG. 7 and FIG. 8 indicate that EndoIV had specificity for a phosphodiester blocking moiety present at the 3' end of a nucleic acid compared to the same blocking moiety on the 3' position of a mononucleotide analog.

The results above demonstrate the surprising finding that the Pol217 polymerase can have selective primer extension reactivity for nucleotide analogs having a phosphotriester blocking moiety at the 3' position of the nucleotide analog (compared to those having a phosphodiester blocking moiety). These results further demonstrate the surprising finding that Endonuclease IV can have selective phosphodiesterase activity for the 3' end of a nucleic acid (compared to phosphotriesterase activity).

Example II

A Reaction Cycle for Sequentially Incorporating Multiple Blocked Nucleotide Analogs into a Primer This example demonstrates a reaction cycle that included the steps of incorporating a phosphotriester blocked nucleotide analog into a primer by the Pol217 polymerase, converting the phosphotriester blocking moiety on the primer to a phosphodiester blocking moiety by the Ada protein, and removing the phosphodiester blocking moiety from the primer by the Endonuclease IV enzyme.

Figure 9:
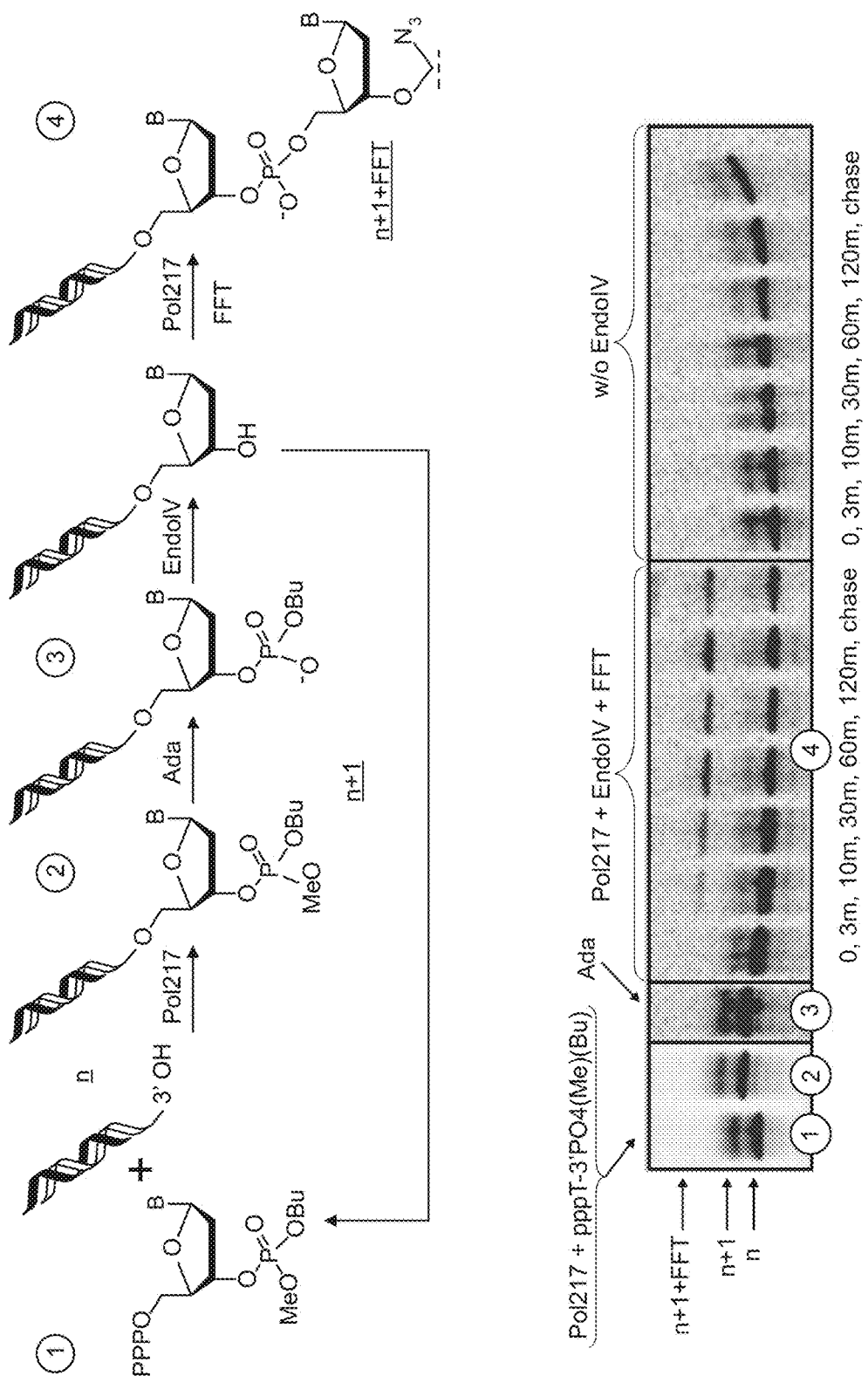
FIG. 9 shows data demonstrating activity of Pol217 for extending a primer to incorporate a nucleotide analog having a phosphotriester blocking moiety, activity of Ada protein for catalyzing conversion of the phosphotriester blocking moiety on the extended primer to a phosphodiester and activity of Endonuclease IV for removing the phosphodiester blocking moiety from the extended primer.

FIG. 9 includes a diagrammatic representation of the following reaction. A $^{33}P$ biotinylated 10 A template hairpin (62mer) was bound to magnetic streptavidin beads (4 pmoles) (1) and incubated with Pol217 (15 µg/ml) in Pol buffer and 10 µM pppT3'$PO_4$MeBu for 10 mins at 55° C. (2). The DNA was then removed to a magnet and washed twice in 1×B+W buffer (5 mM TRIS pH 7.5, 0.5 mM EDTA, 1M NaCl) and then washed twice in Ada buffer (50 mM TRIS pH 8.3, 1 mM EDTA, 3 mM DTT, 1 mg/ml BSA). The DNA was then incubated in Ada buffer with Ada protein (225 pmoles) at 37° C. for 3 h (3). The DNA was then removed to a magnet and washed twice in 1×B+W and then twice in NEB 3 buffer and then divided into 2 aliquots. To one aliquot (4) (2 pmoles) was added Pol 217 (15 µg/ml), E. coli EndoIV 10 U and FFT (5 µM) in NEB 3 buffer to a total volume of 100 µl. The sample was incubated at 37° C. and at time points of 0, 3, 10, 30, 60 and 120 mins a 5 µl sample was removed and quenched for 12% gel analysis. After 120 mins 10 µl of 100 µM dNTP was added to the remaining sample to chase the primer to the end (if not blocked) and an aliquot was taken and quenched after a further 20 mins at 37° C. (chase). The second aliquot (2 pmoles) was treated similarly, but no E. coli Endo IV was added to the reaction mixture (w/o EndoIV).

A photograph of the gel produced by the above reaction is shown in FIG. 9. The gel demonstrates that as DNA (1) is incubated with Pol 217 and pppT3'$PO_4$MeBu it is converted to n+1 (2). Following Ada treatment (3) there is no noticeable change in template size-consistent with removal of only a methyl group. As time progresses the n+1 band is unblocked by EndoIV to produce a free 3'OH on the n+1 DNA, to which Pol 217 can then incorporate a 3' blocked FFT to give a shift to n+1+FFT. In the absence of Endo IV the DNA remains the same across the time course as the n+1 band is not unblocked so no subsequent incorporation of FFT occurs. (N.B. the smear at n+1 in the starting material appears to be an artifact of gel running or a primer impurity, but it follows the trend of incorporation similar to the main primer band).

The above data demonstrate the surprising result that Ada has methyltransferase activity at the 3' end of DNA. The data also surprisingly demonstrates that Ada alone did not remove the phosphate moiety from the 3' position of the nucleotide analog.

Figure 10:
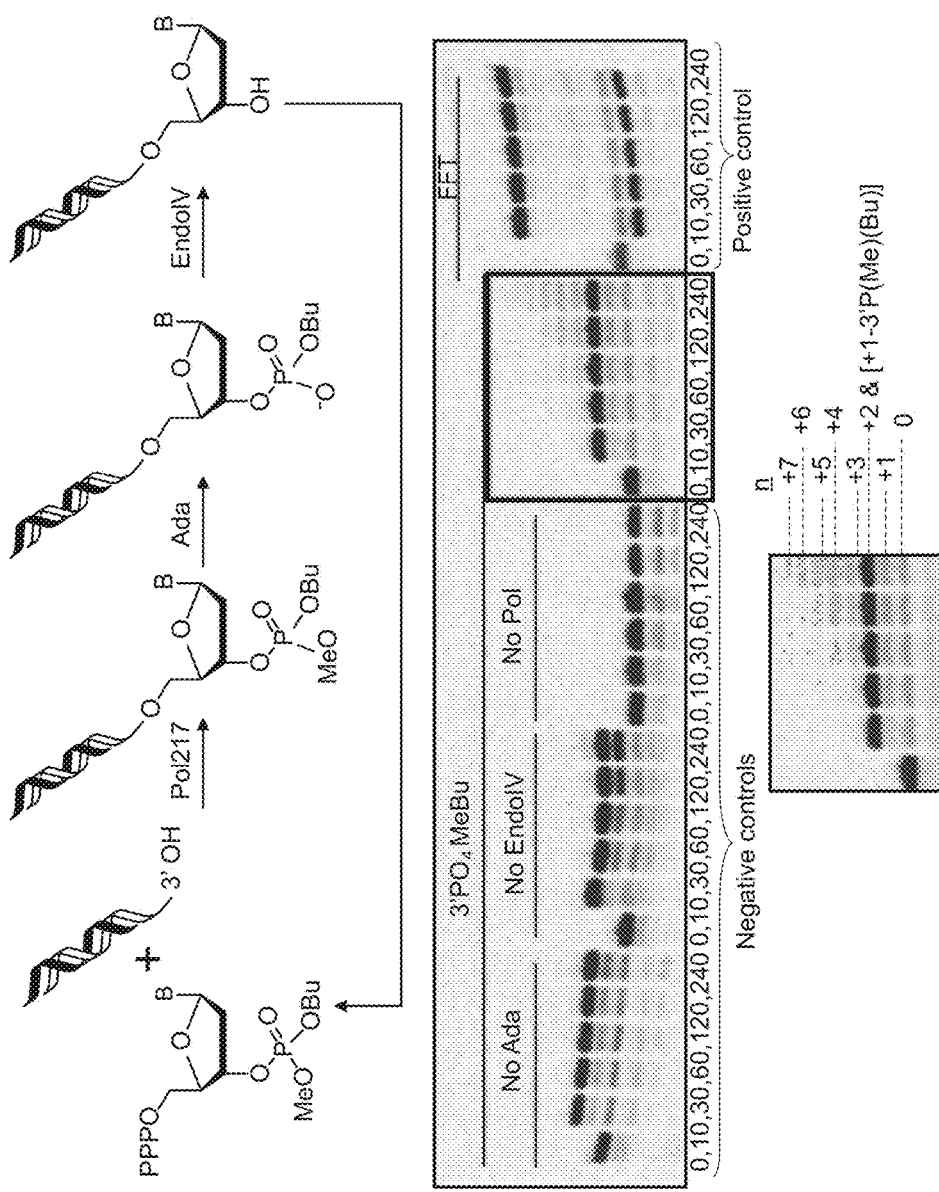
FIG. 10 shows data demonstrating a single pot reaction including multiple cycles whereby Pol217 extends a primer to incorporate a nucleotide analog having a phosphotriester blocking moiety, Ada protein catalyzes conversion of the phosphotriester blocking moiety on the extended primer to a phosphodiester and Endonuclease IV removes the phosphodiester blocking moiety from the extended primer.

FIG. 10 includes a diagrammatic representation of the following reaction. A tube was incubated at 37° C. containing Pol 217 (15 µg/ml-16.5 pmoles), E. coli Endo IV (10 U), Ada protein (1000 pmoles) in 100 µl of 50 mM TRIS pH 8.0, 1 mg/ml BSA, 50 mM NaCl, 10 mM $MgSO_4$ with 2 pmoles of primer (21mer) annealed to 10 A template DNA. After a time zero aliquot was removed and quenched for gel analysis, the reaction was started by the addition of 10 µM pppT3'$PO_4$MeBu. At time points of 10, 30, 60, 120 and 240 minutes an aliquot was removed and quenched for gel analysis. Negative controls are shown where one protein was left out of the mixture in turn. A positive control for incorporation is shown of 10 µM FFT.

The results on the gel shown in FIG. 10 demonstrate that in the absence of Ada (no Ada) or EndoIV (no EndoIV) a single incorporation event occurred. In the absence of polymerase (no pol) no incorporation was seen. In the presence of all three proteins the length of the extension product gradually increased over the time course from n+1 to n+2, then n+3, then n+4 etc. showing several 3'PO$_4$MeBu incorporation events. This only occurred when all three proteins were present showing that each single incorporation event includes processing by both Ada and EndoIV. N.B. the first incorporation band of 3'PO$_4$MeBu is about the size of n+T+T as evidenced by the decrease in this band in the "no EndoIV" samples to n+1, where Ada can remove the methyl group but then the reaction is blocked from proceeding.

Example III

A Primer Extension Reaction Cycle Utilizing a Combination of Chemical and Enzymatic Deblocking This example demonstrates a reaction cycle that included the steps of incorporating a nucleotide analog (having a phosphotriester blocking moiety wherein one of the esters is further linked to a moiety having a disulfide linkage) into a primer by the Pol217 polymerase, converting the phosphotriester blocking moiety on the primer to a phosphodiester blocking moiety by cleaving the moiety having a disulfide linkage with THP, and removing the phosphodiester blocking moiety from the primer by the Endonuclease IV enzyme.

Figure 11:
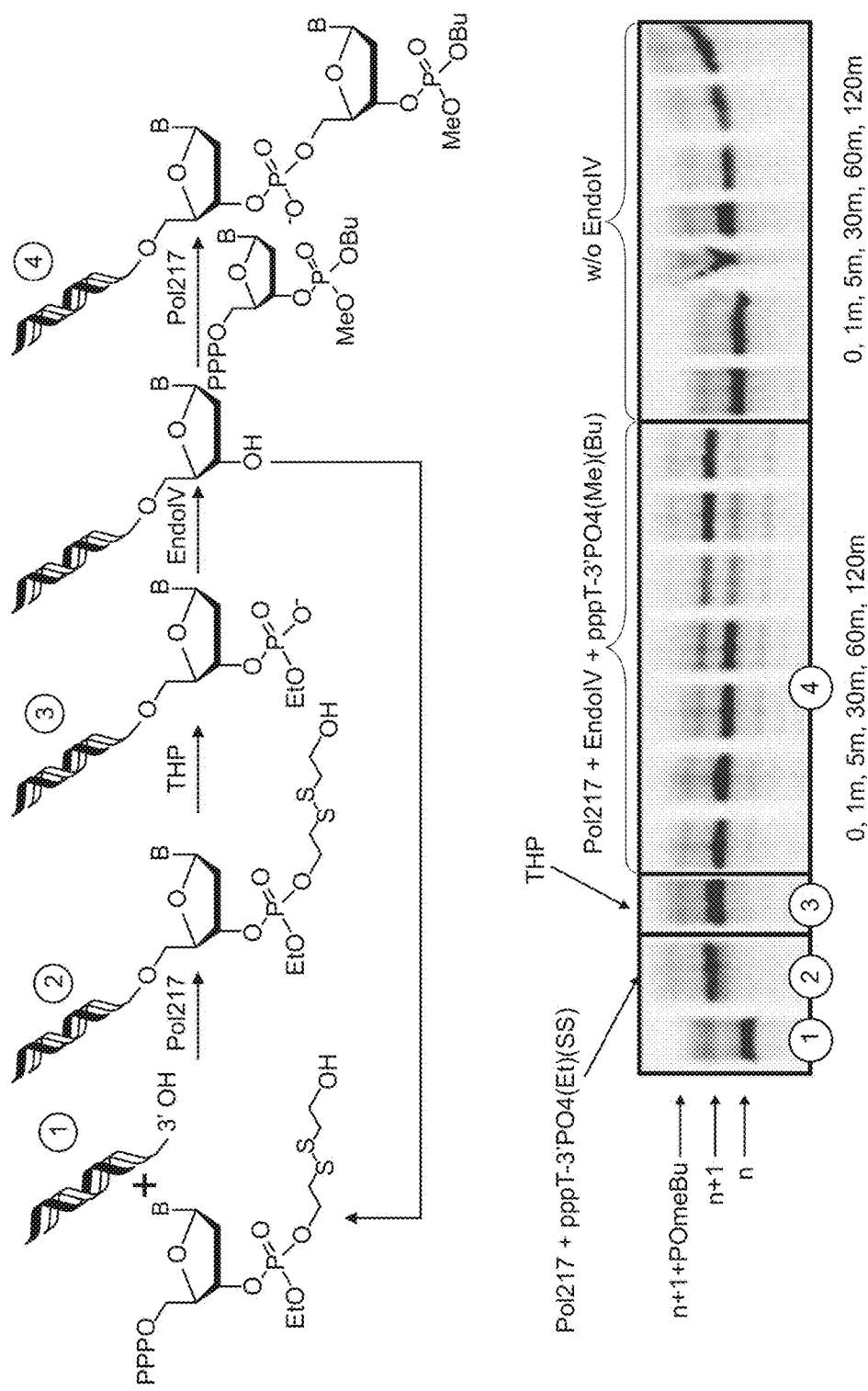
FIG. 11 shows data demonstrating activity of Pol217 for extending a primer to incorporate a nucleotide analog having a phosphotriester blocking moiety with a disulfide linkage, activity of tri(hydroxylpropyl)phosphine (THP) for converting the phosphotriester blocking moiety to a phosphodiester and activity of Endonuclease IV for removing the phosphodiester blocking moiety from the extended primer.

FIG. 11 includes a diagrammatic representation of the following reaction. Eight pmoles of biotinylated 10 A hairpin DNA (62mer) bound to magnetic streptavidin beads (1) was incubated with Pol 217 (15 µg/ml) in Pol buffer with 10 µM pppT3'PO$_4$(Et)(SSOH) in 200 µl at 55° C. for 15 mins (2). Then 2 µl of 100 mM tri(hydroxylpropyl)phosphine (THP) was added to the tube and the samples incubated for a further 5 mins at 55° C. (3). The DNA was then removed to a magnet and washed twice in 1×B+W and twice in NEB 3 buffer. The DNA was then divided into two aliquots. To the first aliquot (4 pmoles) was added 4 U *E. coli* EndoIV, 15 µg/ml Pol 217, 10 µM pppT3'PO$_4$MeBu in 100 µl of NEB3 buffer (4) and the other aliquot (4 pmoles) had the same additions but no EndoIV (w/o EndoIV). At time points of 0, 1, 5, 10, 30, 60 and 120 mins and sample was removed and quenched for 12% gel analysis.

The gel of FIG. 11 show a shift from (1) 10 A hairpin DNA to (2) indicative of the incorporation of pppT3'PO$_4$ (Et)(SSOH) having gone to completion in 15 mins. After THP treatment (3) there is no noticeable change in the band, as expected for the relatively small change in mass for the 3' block after THP treatment. In the presence of EndoIV, polymerase and a second nucleotide the 3'PO$_4$Et blocking moiety was removed over time allowing the polymerase to incorporate a second nucleotide. In the absence of EndoIV no second incorporation was observed as the DNA remains 3' blocked.

The reaction cycle exemplified above is well suited for polynucleotide synthesis schemes and SBS schemes where the chemical deblocking reagent contacts primer extension products but does not come into contact with monomeric nucleotides. Such separation of sequencing reagents occurs, for example, in schemes that use fluid cycling of reagents. Separation of the THP chemical deblocking reagent from monomeric nucleotides can be used to compensate for insufficient specificity of the chemical deblocking reagent for primer extension products (compared to monomeric nucleotides).

Example IV

A Primer Extension Reaction Cycle Utilizing a Combination of Photo-Chemical and Enzymatic Deblocking This example demonstrates a reaction cycle that included the steps of incorporating a nucleotide analog (having a phosphotriester blocking moiety with a photo-labile NPIP moiety) into a primer by the Pol427 polymerase, converting the phosphotriester blocking moiety on the primer to a phosphodiester blocking moiety by irradiating the NPIP moiety with light at 365 nm, and removing the phosphodiester blocking moiety from the primer by the Endonuclease IV enzyme.

Figure 12:
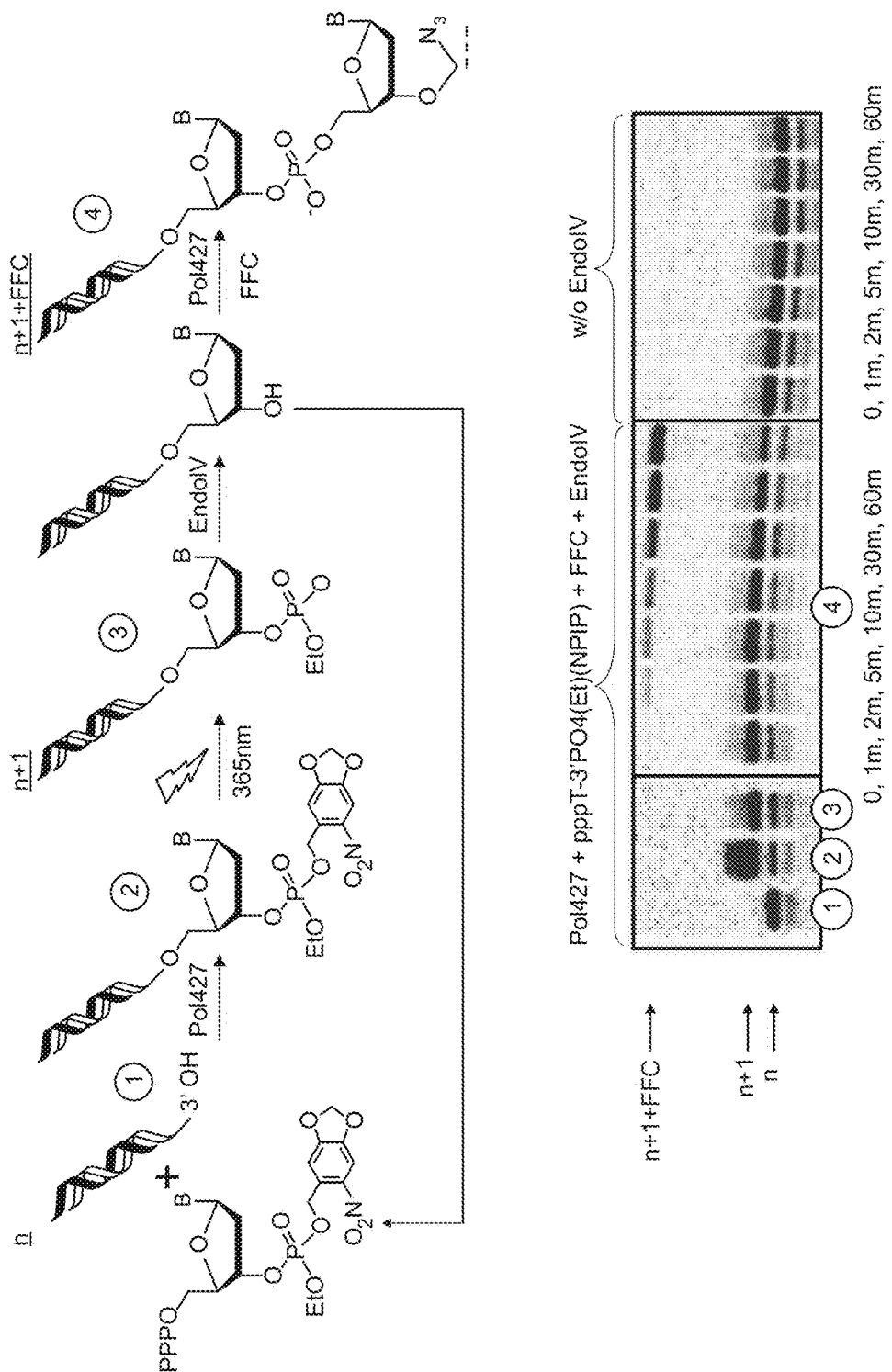
FIG. 12 shows data demonstrating activity of Pol427 for extending a primer to incorporate a nucleotide analog having a phosphotriester blocking moiety with a photo-labile moiety, activity of light at 365 nm for converting the phosphotriester blocking moiety to a phosphodiester and activity of Endonuclease IV for removing the phosphodiester blocking moiety from the extended primer.

FIG. 12 includes a diagrammatic representation of the following reaction. Pol 427 (30 µg/ml) was incubated in Pol buffer with Primer (P21) annealed to template AG and a time 0 sample was taken (1). The reaction was initiated by the addition of pppT3'PO$_4$(Et)(NPIP) and incubated for 1 h at 37° C. An aliquot was quenched for 15% gel analysis (2). The sample was then transferred to a cuvette and irradiated for 2 hours at 365 nm by a low energy light source. An aliquot was quenched for gel analysis (3). The sample was then divided into 2 portions and to the first portion was added fresh Pol 427 (30 µg/ml), 5 µM FFC (reversibly blocked cytosine triphosphate nucleotide, (Illumina, Inc. San Diego, Calif.) that complements the G at the second position of the template) and 4 U of *E. coli* EndoIV (4). To the second portion was added Pol 427 (30 µg/ml) and 5 µM FFC (w/o EndoIV). At 0, 1, 2, 5, 10, 30 and 60 mins a sample was quenched for gel analysis from both portions.

The results in the gel of FIG. 12 show that the starting DNA (1) is converted to n+1 (2), but with a smeary wide, incorporation band. After light treatment this band is sharper (3) reflecting the removal of the relatively large NPIP moiety by the light treatment. On addition of Pol 427, *E. coli* EndoIV and a second nucleotide, the n+1 band is converted into an n+1+FFC band only in the presence of EndoIV. This demonstrates EndoIV removal of the 3' block allowing subsequent incorporation of FFC by Pol 427 over time (4). In the absence of Endo IV (w/o EndoIV) there was no subsequent incorporation event demonstrating that Endo IV removed the 3' block on the primer DNA to allow a second incorporation.

Example V

Incorporation of Gamma Hexynyl Nucleotide Analog in a Prime Extension Reaction

This Example demonstrates polymerase catalyzed extension of a primer to incorporate a nucleotide analog having a hexynyl moiety on the gamma phosphate.

Figure 13:
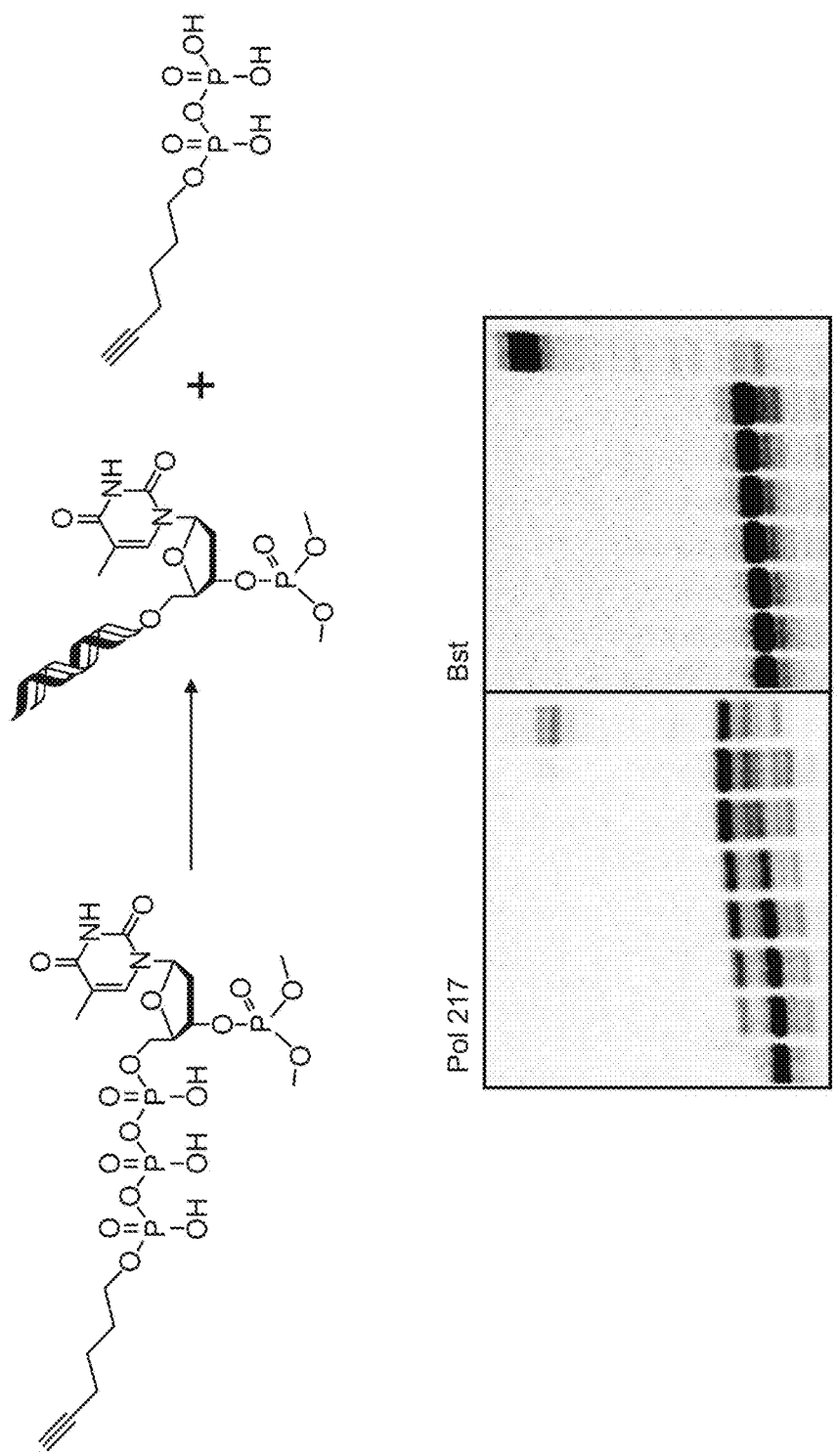
FIG. 13 shows data demonstrating polymerase catalyzed extension of a primer to incorporate a nucleotide analog having a synthetic moiety on the gamma phosphate.

FIG. 13 includes a diagrammatic representation of the following reaction. Incorporation of gamma hexynyl-pppT3'PO$_4$Me$_2$ was tested in Pol buffer at 65° C. with 10 µM nucleotide and 15 µg/ml polymerase (Pol217 or Bst). A time zero sample was removed before initiation of the reaction with nucleotide and aliquots were quenched for gel analysis at 0.33, 0.66, 1, 2, 5 and 15 minutes. After 15 minutes, 5 µl of 100 µM dNTPs was added to the remaining reaction tubes (~20 µl) and incubation continued for 10 mins before a chase aliquot was taken for gel analysis. Thus, for each polymerase there was a time course of 0, 0.33, 0.66, 1, 2, 5, 15 mins and chase shown from left to right across the gel in FIG. 13.

It can be seen from the gel that for Pol 217 an incorporation band of n+1 was generated over time which did not chase away. This indicated that the primer extension product was effectively blocked. The band for extended primer was absent for the Bst sample. The results showed that the gamma hexynyl-pppT3'PO4Me2 was specific for Pol217 compared to Bst under the conditions tested.

Example VI

Synthesis of a Phosphodiester Blocked Nucleotide Analog

Figure 14:
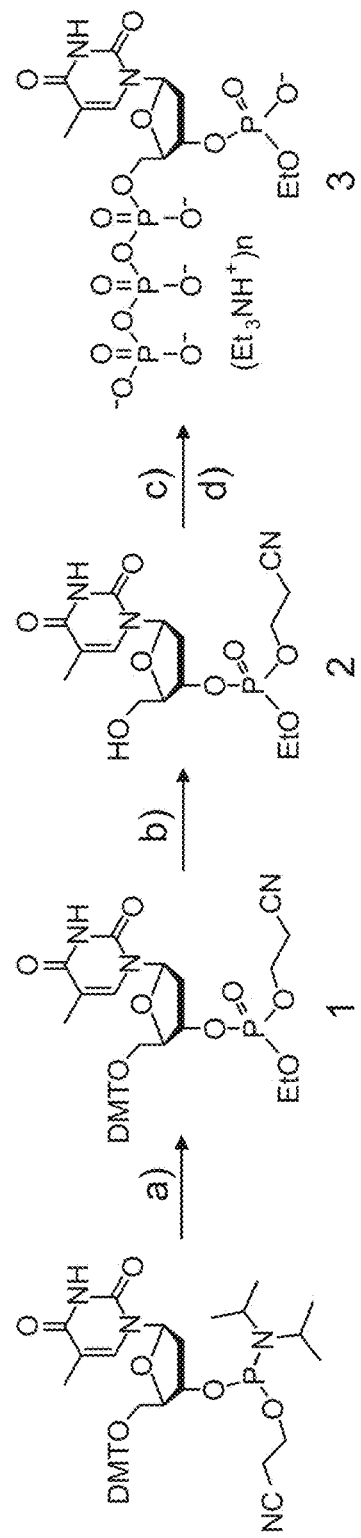
FIG. 14 shows synthesis of a nucleotide 5'triphosphate 3'phosphodiester (pppT-3'PO$_4$Et) using the following reagents: a) 1) ETT, EtOH, MeCN; 2) I$_2$, THF, Pyridine, H$_2$O; b) 3% TCA in CH$_2$Cl$_2$; c) 1) POCl$_3$, proton Sponge®, PO(OEt)$_3$; 2) P$_2$O$_7^{2-}$(Bu$_3$NH$^+$)$_2$, DMF, Bu$_3$N; 3) TEAB 1M, aq.; d) NH$_3$ aq. 35%.

This example demonstrates synthesis of a nucleotide 5' triphosphate 3' phosphodiester (pppT-3'PO$_4$Et) and various intermediate nucleotide analogs. The overall reaction scheme is shown in FIG. 14. Details of the reaction steps and analytical characterization of products follows.

5'-(4,4'-dimethoxytrityl) 3'-(O-ethyl, O-(2-cyanoethyl) phosphate) thymidine (1)

5'-(4,4'-Dimethoxytrityl) thymidine 3'-[(2-cyanoethyl)-N,N-diisopropyl]-phosphoramidite (1 g, 1.34 mmol) was dissolved in anhydrous acetonitrile (7 mL) under nitrogen. Anhydrous ethanol (154 µL, 2.68 mmol) was added, then a solution of 5-ethylthio-1H-tetrazole (ETT, 348 mg, 2.68 mmol) in dry acetonitrile (3 mL) was added dropwise to the phosphoramidite. The mixture was stirred for 30 minutes at room temperature. Then a 0.1 M solution of iodine in THF/pyridine/water 78:20:2 (14.7 mL, 1.47 mmol) was added and the mixture was stirred at room temperature for 10 minutes. The solution was then diluted with 200 mL of dichloromethane and added to a separating funnel containing 500 mL of 5% Na$_2$S$_2$O$_3$ in water. After extraction, the organic phase was separated and further extracted with 200 mL of saturated NaCl. The organic phase was then dried over anhydrous Na$_2$SO$_4$ and the solvent was removed under reduced pressure. The remaining residue was coevaporated twice with 10 mL of toluene. The compound 5'(4,4'-dimethoxytrityl)-3' (O-ethyl, 0'(2-cyanoethyl) phosphate) thymidine (1) was obtained as a mixture of two diastereoisomers and it was utilised in the next step without further purification. Yield: 934 mg (1.32 mmol, 98%). R$_f$ (CH$_2$Cl$_2$/MeOH 95:5): 0.25. $^1$H NMR (400 MHz, CDCl$_3$): δ (ppm) 8.24 (d, J=8.3 Hz, 1H, NH), 7.50 (s, 1H, 5-CH T), 7.17 (m, 9H, Ar DMT), 6.75 (m, 4H, Ar DMT), 6.38 (dd, J=5.4 Hz, J=8.6 Hz, 1H, 1'-CH), 5.07 (s, 1H, 3'-CH), 4.21 (s, 1H, 4'-CH), 4.09 (m, 4H, CH$_2$OP), 3.74 (s, 6H, OCH$_3$ DMT), 3.47 (m, 1H, 5'-CH$_a$), 3.32 (d, J=10.4 Hz, 1H, 5'-CH$_b$), 2.66 (m, 1H, CH$_a$—CN), 2.60 (m, 2H, CH—CN and 2'-CH$_a$), 2.37 (m, 1H, 2'-CH$_b$), 1.38 (m, 3H, CH$_3$ T), 1.25 (m, 3H, CH$_3$ Et). $^{31}$P NMR (162 MHz, CDCl$_3$): δ (ppm) −2.48, −2.66. LC-MS (ES and CI): (negative ion) m/z 704 (M−H$^+$).

3'-(O-ethyl, O'-(2-cyanoethyl) phosphate) thymidine (2)

5'-(4,4'-dimethoxytrityl) 3'-(O-ethyl, O'-(2-cyanoethyl) phosphate) thymidine (1) (934 mg, 1.32 mmol) was dissolved in a solution of trichloroacetic acid 3% (v/v) in anhydrous dichloromethane (10 mL). The reaction was stirred at room temperature for 2 hours. The reaction was diluted with dichloromethane (20 mL) then poured into saturated aqueous NaHCO$_3$ (200 mL). The organic phase was extracted and separated. The aqueous phase was then extracted twice with 50 mL of dichloromethane. The organic phases were pooled, dried over anhydrous Na$_2$SO$_4$ and the solvents were removed under reduced pressure. The crude product was then purified by chromatography on silica gel using a linear gradient of methanol (0% to 10%) in dichloromethane. The compound 3'-(O-ethyl, O'-(2-cyanoethyl) phosphate) thymidine (2) was obtained as a mixture of to diastereoisomers. Yield: 228 mg (0.56 mmol, 42%). R$_f$ (CH$_2$Cl$_2$/MeOH 9:1): 0.4. $^1$H NMR (400 MHz, d6-DMSO): δ (ppm) 11.43 (s, 1H, NH), 7.76 (s, 1H, 5-CH), 6.26 (dd, J=6.0 Hz, J=8.2 Hz, 1H, 1'-CH), 5.30 (m, 1H, OH), 5.02 (s, 1H, 3'-CH), 4.25 (dd, J=6.0 Hz J=12.6 Hz, 1H, 4'-CH), 4.17 (m, 4H, CH$_2$OP), 3.68 (m, 2H, 5'-CH$_2$), 3.00 (t, J=5.8 Hz, 2H, CH$_2$—CN), 2.42 (m, 2H, 2'-CH$_2$), 1.84 (s, 3H, CH$_3$ T), 1.35 (t, J=7.0 Hz, 3H, CH$_3$ Et). $^{31}$P NMR (162 MHz, d6-DMSO): δ (ppm) −2.57, −2.60. LC-MS (ES and CI): (positive ion) m/z 404 (M+H$^+$), 426 (M+Na$^+$).

5' triphosphate 3' (O-ethyl phosphate) thymidine (pppT-3'PO$_4$Et) (3)

3'-(O-ethyl, O'-(2-cyanoethyl) phosphate) thymidine (2) (220 mg, 0.546 mmol) was dried under reduced pressure over P$_2$O$_5$ in a round-bottomed flask with a magnetic stirring bar for 18 hrs. The flask was flushed with nitrogen and sealed with a rubber septum. Anhydrous triethyl phosphate (2.5 mL) was added at room temperature, then the reaction flask was cooled to 0° C. in an ice-bath. Freshly distilled POCl$_3$ (60 µL, 0.65 mmoles) was added drop-wise followed by proton Sponge® (242 mg, 1.13 mmol). After the addition, the reaction was further stirred at 0° C. for 15 minutes. Then, a 0.5 M solution of pyrophosphate as bis-tri-n-butylammonium salt (5.48 mL, 2.74 mmol) in DMF was quickly added to the above reaction, followed immediately by tri-n-butyl amine (550 µL, 2.3 mmol). The reaction was kept in the ice-water bath for another 5 minutes, then quenched by pouring it into 1 M aqueous triethylammonium bicarbonate (TEAB, 20 mL) and stirred at room temperature for 4 hours. All the solvents were evaporated under reduced pressure. A 35% aqueous solution of ammonia (20 mL) was added to the above residue and the mixture was stirred at room temperature for at least 5 hours. The solvents were then evaporated under reduced pressure. The crude product was purified firstly by ion-exchange chromatography on DEAE-Sephadex A25 (100 g). The column was eluted with a linear gradient of aqueous triethylammonium bicarbonate (TEAB, from 0.05 M to 1 M over 1.7 L). The fractions containing the triphosphate were pooled and the solvent was evaporated to dryness under reduced pressure. The crude material was further purified by preparative scale HPLC using a YMC-Pack-Pro C18 column, eluting with 0.1 M TEAB and acetonitrile. The compound 5' triphosphate 3' (O-ethyl phosphate) thymidine (pppT-3'PO$_4$Et) (3) was obtained as triethylammonium salt. Yield: 210 µmol (38%). $^1$H NMR (400 MHz, D$_2$O): δ (ppm) 7.64 (s, 1H, 5-CH), 6.23 (dd, J=4.8 Hz, J=9.0 Hz, 1H, 1'-CH), 4.69 (3'-CH, covered by HDO) 4.22 (s, 1H, 4'-CH), 4.04 (m, 2H, 5'-CH$_2$), 3.77 (m, 2H, CH$_2$OP), 3.01 (q, Et$_3$NH' counter ion), 2.34 (dd, J=5.4 Hz, J=13.9 Hz, 1H, 2'-CH), 2.22 (m, 1H, 2'-CH), 1.77 (s, 3H, CH$_3$ T), 1.05 (t, Et$_3$NH' counter ion), 1.04 (CH$_3$ Et). $^{31}$P NMR (162 MHz, D$_2$O): δ (ppm) −0.73 (s, 3'P), −7.05 (d, J=20.8 Hz, $^\gamma$P), −11.46 (d, J=19.3 Hz, $^\alpha$P), −22.79 (t, J=20.0 Hz, $^\beta$P). LC-MS (ES and CI): (negative ion) m/z 589 (M−H$^+$); (positive ion) m/z 793 (M+Et$_3$NH$^+$).

Using the methods set forth in this example, the compounds pppT-3'PO$_4$(PrOH), pppT-3'PO$_4$ and pppT-3'PO$_4$C12-biotin were synthesised.

Example VII

Synthesis of Phosphotriester Blocked Nucleotide Analogs

This example demonstrates 3 methods for synthesis of phosphotriester blocked nucleotide analogs. The methods are presented as routes A, B and C below.

Figure 15:
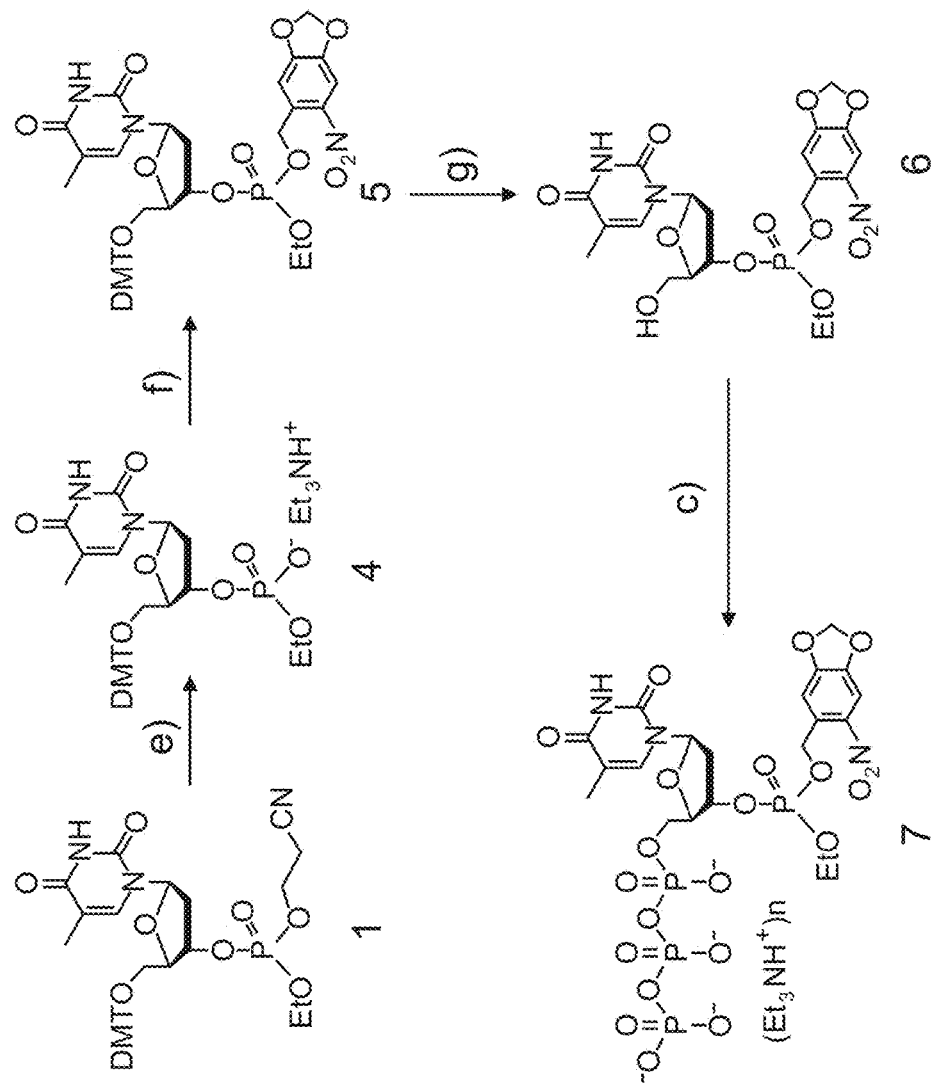
FIG. 15 shows synthesis of a nucleotide 5'-triphosphate 3'-phosphotriester (pppT3'PO$_4$(Et)(NPIP)). Reagents used were e) 35% NH$_3$ aq., MeOH; f) PyBOP, CH$_2$Cl$_2$, DIPEA, 6-nitropiperonyl alcohol; g) AcOH, H$_2$O, MeCN; c) 1) POCl$_3$, proton Sponge®, PO(OEt)$_3$; 2) P$_2$O$_7^{2-}$(Bu$_3$NH$^+$)$_2$, DMF, Bu$_3$N; 2) TEAB 1M, aq.

FIG. 15 shows the overall reaction scheme for route A to the synthesis of a nucleotide 5'-triphosphate 3'-phosphotriester (pppT3'PO$_4$(Et)(NPIP)). Details of the reaction steps follow.

5'-(4,4'-dimethoxytrityl) 3'-(O-ethyl phosphate) thymidine (4)

5'-(4,4'-dimethoxytrityl) 3'-(O-ethyl, O'-(2-cyanoethyl) phosphate) thymidine (1) (924 mg, 1.31 mmol) was dissolved in 10 mL of methanol, then 10 mL of aqueous ammonium hydroxide 35% were added. The solution was stirred at room temperature for 0.5 hours. The solvent was evaporated under reduced pressure, the residue was coevaporated twice with 20 mL of toluene and the crude product was purified by chromatography on silica gel using a linear gradient of methanol (0% to 15%) in dichloromethane with 1% triethylamine. The compound 5'-(4,4'-dimethoxytrityl) 3'-(O-ethyl phosphate) thymidine (4) was obtained as triethylammonium salt. Yield: 817 mg (1.08 mmol, 82%). $R_f$ (CH$_2$Cl$_2$/MeOH/Et$_3$N 85:15:1): 0.5. $^1$H NMR (400 MHz, d6-DMSO): δ (ppm) 11.37 (s, 1H, NH), 7.51 (s, 1H, 5-CH), 7.29 (m, 9H, DMT Ar), 6.89 (dd, J=2.0 Hz J=9.0 Hz, DMT-Ar), 6.19 (dd, J=6.0 Hz J=8.7 Hz, 1H, 1'-CH), 4.63 (m, 1H, 3'-CH), 4.09 (br s, 1H, 4'-CH), 3.73 (s, 6H, CH$_3$ DMT), 3.56 (m, 2H, CH$_2$OP), 3.20 (m, 2H, 5'-CH$_2$), 3.00-2.50 (br, Et$_3$NH$^+$ counter ion), 2.35-2.23 (m, 2H, 2'-CH$_2$), 1.38 (s, 3H, CH$_3$ T), 1.05 (br, Et$_3$NH' counter ion), 1.02 (t, J=7.0 Hz, 3H, CH$_3$ Et). $^{31}$P NMR (162 MHz, d6-DMSO): δ (ppm) −1.86. LC-MS (ES and CI): (negative ion) m/z 651 (M−H).

5'-(4,4'-dimethoxytrityl) 3'-(O-ethyl, O'-(6-nitropiperonyl)phosphate) thymidine (5)

5'-(4,4'-dimethoxytrityl) 3'-(O-ethyl phosphate) thymidine (4) (462 mg, 0.613 mmol) was dissolved in 5 mL of anhydrous dichloromethane. The solution was cooled to 0° C. in an ice bath, then diisopropyl ethyl amine (224 μL, 1.22 mmol) was added, followed by (benzotriazol-1-yloxy)tripyrrolidinophosphonium hexafluorophosphate (PyBOP, 637 mg, 1.22 mmol). The solution was stirred for 1 hour at 0° C., then 6-nitropiperonyl alcohol was added (242 mg, 1.22 mmol). The reaction was allowed to reach room temperature and stirred for 18 hours, wrapped in foil. The reaction was then diluted with 150 mL of dichloromethane and extracted twice with 150 mL of saturated NaHCO$_3$ and 150 mL of water. The organic phase was dried over anhydrous Na$_2$SO$_4$ and evaporated under reduced pressure. The crude product was purified by chromatography on silica gel using a linear gradient of ethyl acetate (from 0% to 100%) in dichloromethane. The compound 5'-(4,4'-dimethoxytrityl) 3'-(O-ethyl, O'-(6-nitropiperonyl)phosphate) thymidine (5) was obtained as a mixture of two diastereoisomers. Yield: 257 mg (0.31 mmol, 50%). $R_f$ (CH$_2$Cl$_2$/MeOH 95:5): 0.55. $^1$H NMR (400 MHz, CDCl$_3$): δ (ppm) 8.27 (d, J=5.6 Hz, 1H, NH), 7.59 (d, J=6.5 Hz, 1H, 5-CH NPIP), 7.50 (s, 1H, 5-CH), 7.29-7.16 (m, 10H, DMT Ar and 2-CH NPIP), 6.75 (m, 4H, DMT-Ar), 6.36 (m, 1H, 1'-CH), 6.08 (d, J=6.3 Hz, 2H, OCH$_2$O), 5.33 (dd, J=7.0 Hz J=22.0 Hz, 2H, POCH$_2$—Ar), 5.11 (t, J=5.7 Hz, 1H, 3'-CH), 4.22 (br s, 1H, 4'-CH), 4.07 (m, 2H, POCH$_2$ Et), 3.71, 3.72 (two s, 6H, CH$_3$ DMT), 3.44 (m, 1H, 5'-CH$_a$), 3.32 (m, 1H, 5'-CH$_b$), 3.01 (q, Et$_3$NH' counter ion), 2.55 (m, 1H, 2'-CH$_a$), 2.36 (m, 1H, 2'-CH$_b$), 1.32 (s, 3H, CH$_3$ T), 1.19 (m, 3H, CH$_3$ Et), 1.07 (t, Et$_3$NH$^+$ counter ion). $^{31}$P NMR (162 MHz, CDCl$_3$): δ (ppm) −2.19, −2.35. LC-MS (ES and CI): (negative ion) m/z 830 (M−H$^+$).

3'-(O-ethyl, O'-(6-nitropiperonyl) phosphate) thymidine (6)

3'-(O-ethyl, O'-(6-nitropiperonyl) phosphate) thymidine (5) (431 mg, 0.52 mmol) was dissolved in 2 mL of acetonitrile then 10 mL of a solution of acetic acid/water 8:2 was added. The reaction was stirred at room temperature for 1.5 hours, then it was diluted with 20 mL of acetonitrile and the solvents were removed under reduced pressure. The residue was coevaporated twice with 10 mL of toluene. The crude product was purified by chromatography on silica gel using a linear gradient of methanol (1% to 10%) in dichloromethane. The compound 3'-(O-ethyl, O'-(6-nitropiperonyl)phosphate) thymidine (6) was obtained as a mixture of two diastereoisomers. Yield: 223 mg (0.42 mmol, 80%). $R_f$ (CH$_2$Cl$_2$/MeOH 95:5): 0.2. $^1$H NMR (400 MHz, CDCl$_3$): δ (ppm) 8.75 (s, 1H, NH), 7.67 (d, J=2.2 Hz, 1H, 5-CH NPIP), 7.48 (s, 1H, 5-CH T), 7.18 (s, 1H, 2-CH NPIP), 6.19 (m, 3H, 1'-CH and OCH2O), 5.47 (dd, J=7.0 Hz J=1.4 Hz, 2H, POCH2-Ar), 5.19 (m, 1H, 3'-CH), 4.22 (m, 3H, 4'-CH and POCH$_2$ Et), 3.92 (m, 2H, 5'-CH$_2$), 3.1 (br, 1H, OH), 1.88 (m, 2H, 2'-CH$_2$), 1.93 (s, 3H, CH$_3$ T), 1.40 (t, J=7.0 Hz, 3H, CH$_3$ Et). $^{31}$P NMR (162 MHz, CDCl$_3$): δ (ppm) −2.03. LC-MS (ES and CI): (negative ion) m/z 528 (M−H$^+$).

5'-triphosphate 3'-(O-ethyl, O'-(6-nitropiperonyl) phosphate) thymidine (pppT-3'PO$_4$(Et)(NPIP)) (7)

3'-(O-ethyl, O'-(6-nitropiperonyl) phosphate) thymidine (6) (105 mg, 0.20 mmol) was dried under reduced pressure over P$_2$O$_5$ in a round-bottomed flask with a magnetic stirring bar for 18 hrs. The flask was flushed with nitrogen and sealed with a rubber septum. Anhydrous triethyl phosphate (1 mL) was added at room temperature, then the solution was cooled with an ice-bath. Freshly distilled POCl$_3$ (23 μL, 0.23 mmol) was added drop-wise followed by proton Sponge® (64 mg, 0.297 mmol). After addition, the reaction was further stirred at 0° C. for 15 minutes. A 0.5 M solution of pyrophosphate as bis-tri-n-butylammonium salt (1.98 mL, 0.99 mmol) in DMF was quickly added to the above reaction, followed immediately by tri-n-butyl amine (200 μL, 0.83 mmol). The reaction was kept in the ice-water bath for another 5 minutes, then quenched by pouring it into 1 M aqueous triethylammonium bicarbonate (TEAB, 15 mL) and stirred at room temperature for 4 hours. Then, all the solvents were evaporated under reduced pressure. The crude product was purified firstly by ion-exchange chromatography on DEAE-Sephadex A25 (50 g). The column was eluted with a linear gradient of aqueous triethylammonium bicarbonate (TEAB, from 0.05 M to 1 M over 1.2 L). The fractions containing the triphosphate were pooled and the solvent was evaporated to dryness under reduced pressure. The crude material was further purified by preparative scale HPLC using a YMC-Pack-Pro C18 column eluting with 0.1

M TEAB and acetonitrile. The compound 5'-triphosphate 3'-(O-ethyl, O'-(6-nitropiperonyl)phosphate) thymidine (pppT-3'PO$_4$(Et)(NPIP)) (7) was obtained as triethylammonium salt and as a mixture of two diastereoisomers. Yield: 0.055 mmol (28%). $^1$H NMR (400 MHz, D$_2$O): δ (ppm) 7.59 (dd, J=1.0 Hz J=4.0 Hz, 1H, 5-CH NPIP), 7.47 (s, 1H, 5-CH T), 6.99 (d, J=2.0 Hz, 1H, 2-CH NPIP), 6.09 (m, 1H, 1'-CH), 6.01 (s, 2H, OCH$_2$O), 5.26 (d, J=8.3 Hz, 2H, POCH$_2$ NPIP), 5.10 (m, 1H, 3'-CH), 4.22 (d, J=14.2 Hz, 1H, 5'-CH$_a$), 4.05 (m, 3H, 5'-CH$_b$ and POCH$_2$ Et), 2.34 (m, 2H, 2'-CH$_2$), 1.73 (s, 3H, CH$_3$ T), 1.17 (t, J=7.0 Hz, 3H, CH$_3$ Et). $^{31}$P NMR (162 MHz, D$_2$O): δ (ppm) −2.73, −2.84 (two s, 3'P, diasteoreois), −6.65 (d, J=20.9 Hz, $^γ$P), −11.46 (d, J=19.5 Hz, $^α$P), −22.69 (t, J=20.0 Hz, $^β$P). LC-MS (ES and CI): (negative ion) m/z 768 (M−H$^+$), 383 (M−2H$^+$).

Using route A, the compounds pppT3'PO$_4$(Et)(Pr-Cap), pppT3'PO$_4$(Et)(PrOH), pppT3'PO$_4$(Et)(SSOH) were also prepared.

Figure 16:
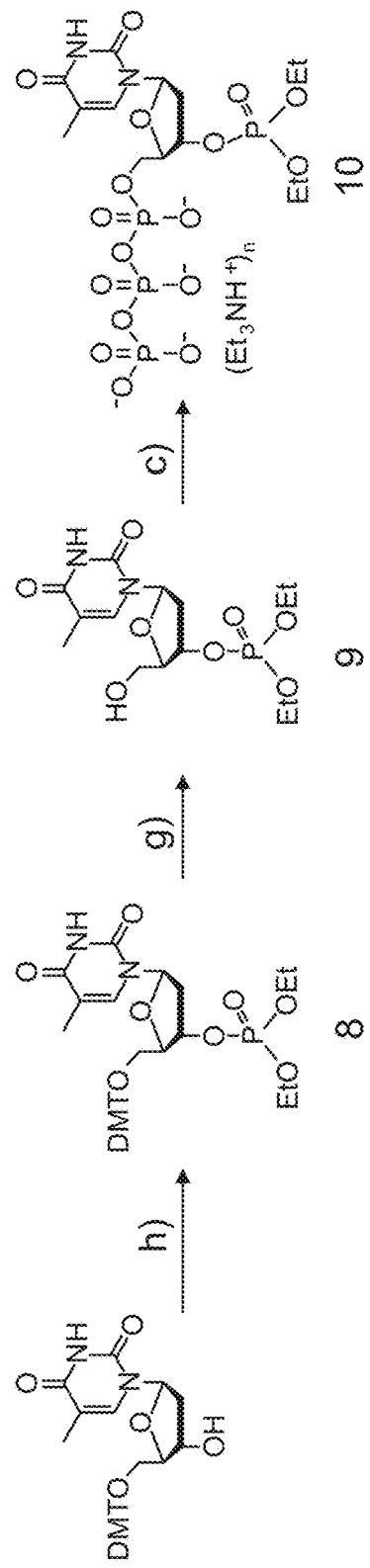
FIG. 16 shows synthesis of a nucleotide 5'-triphosphate 3'-phosphotriester (pppT3'PO$_4$Et$_2$). Reagents: h) PO(OEt)$_2$Cl, N-methylimidazole, dichloromethane; g)

FIG. 16 shows the overall reaction scheme for route B to the synthesis of a nucleotide 5'-triphosphate 3'-phosphotriester (pppT3'PO$_4$Et$_2$). Details of the reaction steps follow.

5'-(4,4'-dimethoxytrityl) 3'-(O,O'-diethyl phosphate) thymidine (8)

5'-(4,4'-dimethoxytrityl) thymidine (544 mg, 1 mmol) was dissolved in anhydrous dichloromethane (10 mL) under nitrogen. N-methylimidazole (123 µL, 1.5 mmol) was added and the solution was cooled at 0° C. in an ice bath. Then, diethyl chlorophosphate (172 µL, 1.2 mmol) was added dropwise and the reaction was stirred at 0° C. for 1 hour. Then, the reaction was then quenched with 50 mL of saturated aqueous NaHCO$_3$, diluted with dichloromethane (50 mL) and transferred to a separating funnel. The two phases were separated and the water phase was further extracted with dichloromethane (50 mL). The organic phases were then pooled, dried over anhydrous Na$_2$SO$_4$ and evaporated under reduced pressure. The crude product was purified by chromatography on silica gel using a linear gradient of methanol (from 0% to 10%) in dichloromethane. Yield: 646 mg (0.95 mmol, 95%). R$_f$ (CH$_2$Cl$_2$/MeOH 95:5): 0.4. $^1$H NMR (400 MHz, CDCl$_3$): δ (ppm) 8.26 (s, 1H, NH), 7.51 (s, 1H, 5-CH T), 7-31-7.18 (m, 9H, Ar DMT), 6.77 (d, J=8.8 Hz, 4H, DMT-Ar), 6.39 (dd, J=8.6 Hz J=5.6 Hz, 1H, 1'-CH), 5.06 (m, 1H, 3'-CH), 4.19 (m, 1H, 4'-CH), 3.97 (m, 4H, POCH$_2$ Et), 3.72 (s, 6H, OCH$_3$ DMT), 3.45 (dd, J=2.6 Hz J$_{gem}$=10.6 Hz, 1H, 5'-CH$_a$), 3.31 (dd, J=2.4 Hz J$_{gem}$=10.6 Hz, 1H, 5'-CH$_b$), 2.99 (q, Et$_3$NH' counter ion), 2.55 (ddd, J=1.5 Hz J=5.4 Hz J=13.8 Hz, 1H, 2'-CH$_a$), 2.35 (m, 1H, 2'-CH$_b$), 1.30 (s, 3H, CH$_3$ T), 1.25 (dt, J=7.0 Hz J$_{PH}$=1.0 Hz, 3H, CH$_3$ Et), 1.21 (dt, J=7.0 Hz J$_{PH}$=1.0 Hz, 3H, CH$_3$ Et), 1.05 (q, Et$_3$NH$^+$ counter ion). $^{31}$P NMR (162 MHz, CDCl$_3$): δ (ppm) −1.95. LC-MS (ES and CI): (negative ion) m/z 679 (M−H$^+$).

3'-(O,O'-diethyl phosphate) thymidine (9)

3'-(O,O'-diethyl phosphate) thymidine (9) was prepared from 5'-(4,4'-dimethoxytrityl) 3'-(O,O'-diethyl phosphate) thymidine (8) (521 mg, 0.68 mmol) using the same reagents and conditions described for 3' (O-ethyl, O'-(6-nitropiperonyl) phosphate) (6). Yield: 160 mg (0.42 mmol, 63%). R$_f$ (CH$_2$Cl$_2$/MeOH 9:1): 0.4. $^1$H NMR (400 MHz, d6-DMSO): δ (ppm) 11.36 (s, 1H, NH), 7.68 (s, 1H, 5-CH T), 6.18 (dd, J=8.5 Hz J=8.6 Hz, 1H, 1'-CH), 5.23 (t, J=5.1 Hz, 1H, OH), 4.91 (s, 1H, 3'-CH), 4.04 (m, 5H, 4'-CH and POCH$_2$ Et), 3.60 (m, 2H, 5'-CH$_2$), 2.32 (m, 2H, 2'-CH$_2$), 1.78 (s, 3H, CH$_3$ T), 1.24 (t, J=7.0 Hz, 6H, CH$_3$ Et). $^{31}$P NMR (162 MHz, d6-DMSO): δ (ppm) −2.03. LC-MS (ES and CI): (positive ion) m/z 401 (M+Na$^+$), 779 (2M+Na$^+$); (negative ion) m/z 377 (M−H$^+$), 755 (2M−H$^+$), 777 (2M−2H++Na+).

5'-triphosphate 3'-(O,O'-diethyl phosphate) thymidine (pppT-3'PO$_4$Et2) (10)

5'-triphosphate 3'-(O,O'-diethyl phosphate) thymidine (10) was prepared from 3'-(O,O'-diethyl phosphate) thymidine (9) (160 mg, 0.42 mmol) using the same reagents and conditions described for 5'-triphosphate 3'-(O-ethyl, O'-(6-nitropiperonyl)phosphate) thymidine (7). Yield: 0.0063 mmol (1.4%). $^1$H NMR (400 MHz, D$_2$O): δ (ppm) 7.66 (s, 1H, 5-CH T), 6.27 (dd, J=5.6 Hz J=9.2 Hz, 1H, 1'-CH), 5.13 (t, J=5.2 Hz, 1H, 3'-CH), 4.37 (m, 1H, 4'-CH), 4.10 (m, 4H, 5'-CH$_2$ and POCH$_2$ Et), 2.45 (dd, J$_3$=5.5, J$_{gem}$=14.5, 1H, 2'-CH$_a$), 2.34 (m, 1H, 2'-CH$_b$), 1.81 (s, 3H, CH$_3$ T), 1.23 (dt, J$_{PH}$=1.0, J$_3$=7.0, 6H, CH$_3$ Et). $^{31}$P NMR (162 MHz, D$_2$O): δ (ppm) −2.17 (s, 3'P), −6.42 (d, J=19.6 Hz, $^γ$P), −11.80 (d, J=19.3 Hz, $_α$P), −22.46 (t, J=19.8 Hz, $^β$P). LC-MS (ES and CI): (negative ion) m/z 617 (M−H$^+$), 308 (M−2H$^+$); (positive ion) m/z 720 (M+Et$_3$NH$^+$).

Compound pppT-3'PO$_4$Me$_2$ was also prepared by the general method of route B.

FIG. 17 shows the overall reaction scheme for route C to the synthesis of a nucleotide 5'-triphosphate 3'-phosphotriester (pppT-3'PO$_4$MeBu). Details of the reaction steps follow.

5'-(4,4'-dimethoxytrityl) 3'-(O-methyl, O'-butyl phosphate) thymidine (11)

5'-(4,4'-Dimethoxytrityl)-thymidine 3'-[O-methyl N,N-diisopropyl]-phosphoramidite (500 mg, 0.7 mmol) was dissolved in 3 mL of anhydrous acetonitrile under nitrogen. Anhydrous n-butanol (208 µL, 1.41 mmol) was added, then a solution of 5-ethylthio-1H-tetrazole (ETT, 183 mg, 1.41 mmol) in dry acetonitrile (2 mL) was added dropwise to the phosphoramidite. The mixture was stirred for 30 min at room temperature. Then a 0.1 M solution of iodine (7.7 mL, 0.77 mmol) in THF/pyridine/water (78:20:2) was added and the mixture was stirred at room temperature for 10 minutes. The solution was then diluted with 100 mL of dichloromethane and added to a separating funnel containing 100 mL of 5% Na$_2$S$_2$O$_3$ in water. After extraction, the organic phase was separated and further extracted with 50 mL of water. The organic phase was then dried over Na$_2$SO$_4$ anhydrous and the solvent was removed under reduced pressure. The remaining residue was coevaporated twice with 10 mL of toluene. The crude was purified by chromatography on silica gel using a linear gradient of ethyl acetate (from 60% to 100%) in dichloromethane. The product was further repurified using a linear gradient of methanol (from 0.4% to 5%) in dichloromethane. The compound 5'-(4,4'-dimethoxytrityl) 3'-(O-methyl, O'-butyl phosphate) thymidine (11) was obtained as a mixture of two diastereoisomers. Yield: 160 mg (0.23 mmol, 33%). R$_f$ (CH$_2$Cl$_2$/MeOH 95:5): 0.5. $^1$H NMR (400 MHz, CDCl$_3$): δ (ppm) 8.14 (d, J=2.9 Hz, 1H, NH), 7.59 (s, 1H, 5-CH T), 7-39-7.26 (m, 9H, Ar DMT), 6.85 (d, J=8.9 Hz, 4H, DMT-Ar), 6.47 (ddd, J=8.6 Hz J=5.4 Hz J=1.8 Hz, 1H, 1'-CH), 5.15 (t, J=6.1 Hz, 1H, 3'-CH), 4.28 (t, J=2.1 Hz, 1H, 4'-CH), 4.04 (m, 2H, POCH$_2$ Bu), 3.81 (s, 6H, OCH$_3$ DMT), 3.76, 3.71 (two d, J$_{PH}$=11.3, 3H, POCH$_3$, two diastereoisomers), 3.54 (dt, J=2.5 Hz J$_{gem}$=10.7 Hz, 1H, 5'-CH$_a$), 3.40 (dd, J=2.4 Hz J$_{gem}$=10.6 Hz, 1H, 5'-CH$_b$), 2.55 (dd, J=5.5 Hz J=14.0 Hz, 1H, 2'-CH$_a$), 2.35 (m, 1H, 2'-CH$_b$), 1.65 (m, 2H, CH2 Bu), 1.38 (m, 5H, CH$_2$ Bu and CH$_3$ T), 0.95, 0.92 (two t, J=7.4 Hz, 3H, CH$_3$ Bu, two diastereoisomers). $^{31}$P NMR (162 MHz, CDCl$_3$): δ (ppm) −0.71. LC-MS (ES and CI): (negative ion) m/z 693 (M−H$^+$).

3'-(O-methyl, O'-butyl phosphate) thymidine (12)

The compound 3'-(O-methyl, O'-butyl phosphate) thymidine (12) was prepared from 5'-(4,4'-dimethoxytrityl) 3'-(O-methyl, O'-butyl phosphate) thymidine (11) (160 mg, 0.23 mmol) using the same reagents and conditions described for 3'-(O-ethyl, O'-(6-nitropiperonyl) phosphate) (6). The compound 12 was obtained as a mixture of two diastereoisomers. Yield: 85 mg (0.21 mmol, 94%). R$_f$ (CH$_2$Cl$_2$/MeOH 9:1): 0.5. $^1$H NMR (400 MHz, CDCl$_3$): δ (ppm) 8.81 (s, 1H, NH), 7.49 (s, 1H, 5-CH T), 6.22 (t, J=7.5 Hz, 1H, 1'-CH), 5.12 (m, 1H, 3'-CH), 4.22 (d, J=2.3 Hz, 1H, 4'-CH), 4.08 (m, 2H, POCH$_2$ Bu), 3.93 (dt, J=2.6 Hz J$_{gem}$=12.1 Hz, 1H, 5'-CH$_a$), 3.88 (dd, J=2.4 Hz J$_{gem}$=12.1 Hz, 1H, 5'-CH$_b$), 3.80, 3.79 (two d, J$_{PH}$=10.4 Hz, 3H, POCH$_3$ two diastereoisomers), 2.50 (m, 2H, 2'-CH$_2$), 1.93 (s, 3H, CH$_3$ T), 1.69 (quin, J=7.8 Hz, 2H, CH$_2$ Bu), 1.42 (sext, J=7.6 Hz, 2H, CH$_2$ Bu), 0.96, 0.95 (two t, J=7.4 Hz, 3H, CH$_3$ Bu, two diastereoisomers). $^{31}$P NMR (162 MHz, d6-DMSO): δ (ppm) −0.43. LC-MS (ES and CI): (positive ion) m/z 415 (M+Na$^+$), 807 (2M+Na$^+$); (negative ion) m/z 391 (M−H$^+$), 783 (2M−H$^+$).

5' triphosphate 3' (O-methyl, O'-butyl phosphate) thymidine (pppT3'PO$_4$MeBu) (13)

The compound 5' triphosphate 3' (O-methyl, O'-butyl phosphate) thymidine (13) was prepared from 3' (O-methyl, O'-butyl phosphate) thymidine (12) (80 mg, 0.20 mmol) using the same reagents and conditions described for 5' triphosphate 3' (O-ethyl, O'-(6-nitropiperonyl) phosphate) thymidine (7). The compound (13) was obtained as triethylammonium salt and as a mixture of two diastereoisomers. Yield: 0.082 mmol (41%). $^1$H NMR (400 MHz, D$_2$O): δ (ppm) 7.58 (s, 1H, 5-CH T), 6.20 (dd, J=5.6 Hz J=9.2 Hz, 1H, 1'-CH), 5.05 (t, J=5.3 Hz, 1H, 3'-CH), 4.27 (m, 1H, 4'-CH), 3.99 (m, 4H, 5'-CH$_2$ and POCH$_2$ Bu), 3.65 (d, J$_{PH}$=11.3, 3H, POCH$_3$), 2.99 (q, Et$_3$NH$^+$ counter ion), 2.34 (m, 2H, 2'-CH$_2$), 1.73 (s, 3H, CH$_3$ T), 1.51 (quin, J=7.2 Hz, 2H, CH$_2$ Bu), 1.21 (sext, J=7.6 Hz, 2H, CH$_2$ Bu), 1.05 (t, Et$_3$NH$^+$ counter ion), 0.73 (t, J=7.4 Hz, 3H, CH$_3$ Bu). $^{31}$P NMR (162 MHz, D$_2$O): δ (ppm) −0.95, −1.02 (two s, 3'P, two diastereoisomers), −6.61 (d, J=21.0 Hz, $^γ$P), −11.00 (d, J=19.3 Hz, $^α$P), −22.75 (t, J=20.1 Hz, $^β$P). LC-MS (ES and CI): (negative ion) m/z 315 (M−2H$^+$), 631 (M−H$^+$); (positive ion) m/z 734 (M+Et$_3$NH$^+$).

Example VIII

Synthesis of 5'-(γ-alkyl)triphosphate 3'-phosphotriester

This example demonstrates synthesis of 5'-(γ-alkyl) triphosphate 3'-phosphotriester. The overall reaction scheme is shown in FIG. 18. Details of the reaction steps and analytical characterization follow.

3'-(O,O'-dimethyl phosphate) thymidine (14) (96 mg, 0.27 mmol) was dried under reduced pressure over P$_2$O$_5$ in a round-bottomed flask with a magnetic stirring bar for 18 hrs. The flask was flushed with nitrogen and sealed with a rubber septum. Anhydrous triethyl phosphate (1 mL) was added at room temperature then the solution was cooled with ice-bath. Freshly distilled POCl$_3$ (31 μL, 0.33 mmol) was added drop-wise, followed by proton sponge (88 mg, 0.41 mmol). After addition, the reaction was further stirred at 0° C. for 15 minutes. A 0.5 M solution of pyrophosphate as bis-tri-n-butylammonium salt (0.65 mL, 0.33 mmol) in DMF was quickly added to the above reaction, followed immediately by tri-n-butyl amine (65 μL, 0.27 mmol). The reaction was kept in the ice-water bath for another 5 minutes. Then, 5-hexyn-1-ol (2.7 mL, 27.4 mmol) was added and the mixture was stirred overnight at room temperature. The reaction was then quenched by pouring it into 1 M aqueous triethylammonium bicarbonate (TEAB, 10 mL) and stirred at room temperature for 4 hours. Then, all the solvents were evaporated under reduced pressure. The crude product was purified firstly by ion-exchange chromatography on DEAE-Sephadex A25 (50 g). The column was eluted with a linear gradient of aqueous triethylammonium bicarbonate (from 0.05 M to 1 M over 1.2 L). The fractions containing the triphosphate were pooled and the solvent was evaporated to dryness under reduced pressure. The crude material was further purified by preparative scale HPLC using a YMC-Pack-Pro C18 column eluting with 0.1 M TEAB and acetonitrile. The compound 5'-(γ-(5-hexynyl) triphosphate) 3'-(O,O'-dimethyl phosphate) thymidine (γ-hexynyl-pppT-3'PO$_4$Me$_2$) (15) was obtained as triethylammonium salt. Yield: 4.15 μmol, (1.5%). $^1$H NMR (400 MHz, D$_2$O): δ (ppm) 7.65 (s, 1H, 5-CH T), 6.37 (dd, J=5.5 Hz J=9.2 Hz, 1H, 1'-CH), 5.15 (t, J=5.2 Hz, 1H, 3'-CH), 4.39 (m, 1H, 4'-CH), 4.13 (m, 2H, 5'-CH$_2$), 3.89 (m, 2H, $^γ$POCH$_2$ hex), 3.79 (d, J$_{PH}$=11.3, 6H, POCH$_3$), 3.06 (q, Et$_3$NH$^+$ counter ion), 2.50 (dd, J=5.4 Hz J=14.5 Hz, 1H, 2'-CH$_a$), 2.35 (m, 1H, 2'-CH$_b$), 2.24-2.13 (m, 3H, CH$_2$ hex and CCH hex), 1.85 (s, 3H, CH$_3$ T), 1.64 (m, 2H, CH$_2$ hex), 1.51 (m, 2H, CH$_2$ hex), 1.18 (t, Et$_3$NH$^+$ counter ion). $^{31}$P NMR (162 MHz, D$_2$O): δ (ppm) −0.20 (s, 3'P), −11.08 (d, J=19.3 Hz, $^α$P), −12.03 (d, J=18.9 Hz, $^γ$P), −23.39 (t, J=18.2 Hz, $^β$P). LC-MS (ES and CI): (negative ion) m/z 334 (M−2H$^+$), 669 (M−H$^+$); (positive ion) m/z 772 (M+Et$_3$NH$^+$).

Example IX

A Primer Extension Reaction Cycle Utilizing Nucleotides Having Phosphodiester Blocking Moieties, Polymerase and Phosphodiesterase This example demonstrates a reaction cycle that includes the steps of incorporating a nucleotide analog (having a phosphodiester blocking moiety) into a primer by the Pol427 polymerase, and removing the phosphodiester blocking moiety from the primer by the Endonuclease IV enzyme.

5' radiolabelled primer DNA with a penultimate 3' phosphorothioate linkage was annealed to a template with a 10 A base overhang and incubated at 20 nM in incorporation buffer (50 mm TRIS pH 9.0, 50 mM NaCl, 6 mM MgSO$_4$, 0.05% tween 20, 1 mm EDTA) at 65° C. with 200 μM pppT3' phosphate C12 biotin (diester nucleotide) plus or minus 4 units of E. coli endonuclease IV. To start the reaction Pol 427 (30 μg/ml final) was added to the reaction mix and aliquots removed to quench solution (EDTA, urea loading dye) immediately, 30 min, 1, 2, 3, 4, 6 hours and after overnight incubation. The quenched aliquots were analyzed by 12% urea sequencing gels to give the result in FIG. 19.

In the absence of endo IV (No endo IV) the starting primer (n) was gradually replaced with a larger species due to the incorporation of the diester nucleotide onto the 3' end of the primer (n+dn). When endo IV was present (4 U E. coli endo IV) a very different banding pattern was observed with early time points showing n and bands of smaller increase in size (e.g. n+T). The band n+T represents DNA which has been extended by addition of a diester nucleotide and then subsequently unblocked by endo IV to give a primer extended by one T base (now lacking the 3' block). As time progressed this n+T band underwent incorporation of a second diester nucleotide and subsequent unblocking until several bases were incorporated generating a growing strand of DNA. Since each strand proceeded at a different rate many species were present at any one time giving multiple bands on the gel, but all gradually growing over time.

Example X

Evaluation of Nucleotide Analogs Having Various 5' Phosphate Modifications

This example demonstrates the effect of 5' phosphate modifications on polymerase incorporation activity.

Polymerase incorporation reactions were performed with a series of dT 3' phosphate (Et)2 nucleotide analogs having 3, 4 or 5 phosphates at the 5' position. Several of the analogs also had a small hexynyl attachment. Also one of the analogs had 5 phosphates at the 5' position and a black hole quencher (BHQ) attached to the hexynyl arm.

Incorporation reactions were carried out at 65° C. in incorporation buffer (as described in Example IX) with Pol217 and testing the nucleotides at 10 µM. Again aliquots were removed for quenching and gel analysis. Time points were taken as labeled (in minutes) in FIG. 20.

The top gel of FIG. 20 shows that a 5' of just triphosphate ((P)3-T-3'PO$_4$Et$_2$) is incorporated very rapidly and completely within 20 seconds. However, addition of a hexynyl linker to the 5' phosphate (Hexy(P)3-T-3'PO$_4$Et$_2$) slowed down incorporation to such an extent that the DNA degraded. Adding an extra phosphate (Hexy(P)4-T-3'PO$_4$Et$_2$) allowed incorporation within 10 minutes and adding another phosphate to give a pentaphosphate attachment (Hexy(P)5-T-3'PO$_4$Et$_2$) accelerated incorporation further to be within 2 minutes. The lower gel of FIG. 20 shows a repeat of the incorporation reactions for ((P)$_3$-T-3'PO$_4$Et$_2$ (identified as pppEt$_2$ in the lower gel of FIG. 20) and Hexy(P)5-T-3'PO$_4$Et$_2$ (identified as hexpppppEt2 in the lower gel of FIG. 20) nucleotides and also shows that adding a bulky black hole quencher to the hexynyl pentaphosphate linker of the nucleotide (identified as BHQpppppEt2 in the lower gel of FIG. 20) enables incorporation to be complete within 5 minutes.

Structures for the nucleotides are shown in FIG. 24. The nomenclature in the figures is as follows: hex-pppT-3'PO4ET$_2$ is the same as Hexy(P)3-T-3'PO$_4$Et$_2$; hex-ppppT-3'PO4ET$_2$ is the same as Hexy(P)4-T-3'PO$_4$Et$_2$; hex-pentaPT-3'PO4ET$_2$ is the same as Hexy(P)5-T-3'PO$_4$Et$_2$; and BHQ2-pentaPT-3'PO4ET$_2$ is the same as BHQpppppEt2.

Example XI

Synthesis of a Quencher/Dye Labeled Nucleotide 5'-Triphosphate 3'-Phosphodiester This example describes synthesis of a quencher/dye labeled nucleotide 5'-triphosphate 3'-phosphodiester. A diagrammatic representation of the synthesis scheme is shown in FIG. 21.

1-Hex-5-ynyl methanesulfonate (16)

5-Hexyn-1-ol (2 g, 20 mmol) was dissolved in anhydrous dichloromethane and placed in an ice bath. Triethylamine (4.3 mL, 30 mmol) was added, followed by methanesulfonyl chloride (1.82 mL, 24 mmol). After stirring for 10 minutes, the solution turned yellow and a precipitate formed. The ice bath was removed and the reaction was stirred at room temperature for 1 hour. The solution was then diluted with 150 mL of dichloromethane, extracted with 3×150 mL of 0.05 M HCl, with 3×150 mL of sat. NaHCO$_3$, then with 150 mL of water. The organic phase was dried over Na$_2$SO$_4$ anhydrous and the solvent was removed under reduced pressure. The product appeared as a yellow oil. Yield: 3.41 g, 19.2 mmol, 96%. R$_f$ (CH$_2$Cl$_2$/Pet. Ether 8:2): 0.7. $^1$H NMR (400 MHz, CDCl$_3$): δ (ppm) 4.20 (t, J=6.3 Hz, 2H, CH$_2$—O), 2.95 (s, 3H, CH$_3$—S), 2.19 (dt, J$_4$=2.6 Hz, J=6.9 Hz, 2H, CH$_2$(4)), 1.91 (t, J$_4$=2.6 Hz, 1H, CH(6)), 1.82 (m, 2H, CH$_2$(2)), 1.58 (m, 2H, CH$_2$(3)).

1-Hex-5-ynyl pyrophosphate tris(tri-n-butylammonium) salt (17)

Pyrophosphate tetrakis(tetra-n-butylammonium) salt (0.5 M in dry acetonitrile, 10 mmol) was placed in a round bottomed flask containing activated molecular sieves under nitrogen gas. 1-Hex-5-ynyl methanesulfonate (16) (1.76 g, 10 mmol) was added dropwise via a syringe and the solution was stirred at room temperature for 4 hours. After this time, TLC (CH$_2$Cl$_2$) indicated that most of 16 had reacted. The solvent was evaporated under reduced pressure, the residue was dissolved in 50 mL of water and passed through a column of Dowex 50WX8-200 (acid form, 40 g), previously equilibrated with water. The acidic fractions were collected in a flask containing ethanol (50 mL) and tri-n-butylamine (7.2 mL, 30 mmol), stirring vigorously. The solution was then evaporated under reduced pressure. The residue was further coevaporated with 2×100 mL of ethanol and 2×50 mL of anhydrous DMF. The final product (17) was quantified by $^1$H NMR titration, using acetonitrile as standard, then dissolved in dry DMF to 0.5 M concentration. Yield: 9.97 g (7.1 mmol, 71%). $^1$H NMR (400 MHz, D2O): δ (ppm) 3.84 (t, J=6.3 Hz, 2H, CH$_2$—O), 3.00 (m, 24H, CH$_2$N Bu), 2.21 (t, J$_4$=2.6 Hz, 1H, CH(6)), 2.15 (dt, J$_4$=2.6 Hz, J=7.0 Hz, 2H, CH$_2$(4)), 1.57 (m, 2H, CH$_2$(2)), 1.54 (m, 24H, CH$_2$CH$_2$N Bu), 1.25 (sext, J=7.5 Hz, 24H, CH$_2$CH$_2$CH$_2$N Bu), 0.82 (t, J=7.3 Hz, 36H, CH$_3$ Bu). $^{31}$P NMR (162 MHz, CD$_3$CN): δ (ppm) −10.18 (d, 1P, J=17.4 Hz), −10.57 (d, 1P, J=17.4 Hz).

3'-(O-(12-trifluoroacetylaminododecyl), O'-(2-cyanoethyl)phosphate)thymidine (18)

The compound 3'-(O-(12-trifluoroacetylaminododecyl), O'-(2-cyanoethyl)phosphate)thymidine (18) was synthesised from 5'-(4,4'-Dimethoxytrityl)thymidine 3'-[(2-cyanoethyl)-N,N-diisopropyl]-phosphoramidite (2.10 g, 2.82 mmol) as described for Compounds 2 and 3. Yield over two steps: 1.29 g (1.97 mmol, 70%). R$_f$ (CH$_2$Cl$_2$/MeOH 9:1): 0.4. $^1$H NMR (400 MHz, CDCl$_3$): δ (ppm) 9.17 (s, 1H, NH), 7.51 (s, 1H, 5-CH), 6.65 (br, 1H, NH), 6.23 (t, J=7.0 Hz, 1H, 1'-CH), 5.17 (m, 1H, 3'-CH), 4.34-4.22 (m, 3H, 4'-CH and CH$_2$OP), 4.12 (q, 2H, J=6.8 Hz, CH$_2$OP), 3.92 (m, 2H, 5'-CH$_2$), 3.35 (q, J=6.8 Hz, 2H, CH$_2$NHTFA), 3.2 (br, 1H, OH), 2.81 (m, 2H, CH$_2$—CN), 2.51 (m, 2H, 2'-CH$_2$), 1.92 (s, 3H, CH$_3$ T), 1.71 (quin, J=7.0 Hz, 2H, CH$_2$Cl$_2$), 1.58 (quin, J=7.0 Hz, 2H, CH$_2$Cl$_2$), 1.31 (m, 16H, CH$_2$Cl$_2$). $^{31}$P NMR (162 MHz, CDCl$_3$): δ (ppm) −2.33-2.37. LC-MS (ES and CI): (positive ion) m/z 655 (M+H$^+$); (negative ion): 653 (M−H$^+$).

5'-(γ-(1-hex-5-ynyl)triphosphate) 3'-(O-(12-aminododecyl)phosphate)thymidine (hex-pppT-3'PO$_4$C12NH$_2$) (19)

3'-(O-(12-trifluoroacetylaminododecyl), O'-(2-cyanoethyl) phosphate) thymidine (18) (196 mg, 0.3 mmol) was dried under reduced pressure over P$_2$O$_5$ in a round-bottomed flask for 18 hrs. The flask was flushed with nitrogen and sealed with a rubber septum Anhydrous triethyl phosphate (3 mL) was added at room temperature then the solution was cooled with an ice bath. Freshly distilled POCl$_3$ (34 µL, 0.36 mmol) was added dropwise, followed by Proton Sponge (96 mg, 0.45 mmol). After the addition, the reaction was stirred at 0° C. for 15 minutes. A 0.5 M solution of 1-hex-5-ynyl pyrophosphate as tris(tri-n-butylammonium) salt (3 mL, 1.5 mmol) in DMF was quickly added to the above reaction, followed immediately by tri-n-butyl amine (300 µL, 1.41 mmol). The reaction was kept in the ice-water bath for another 5 minutes, then quenched by pouring it into 1 M aqueous triethylammonium bicarbonate (TEAB, 30 mL) and stirred at room temperature for 4 hours. All the solvents were evaporated under reduced pressure. A 35% aqueous solution of ammonia (30 mL) was added to the residue and the mixture was stirred at room temperature for 5 hours. The solvents were then evaporated under reduced pressure. The crude product was purified firstly by ion-exchange chromatography on DEAE-Sephadex A25 (100 g). The column was eluted with a linear gradient of aqueous triethylammonium bicarbonate (from 0.05 M to 1 M over 2 L). The fractions containing the triphosphate were pooled and the solvent was evaporated to dryness under reduced pressure. The crude material was further purified by preparative scale HPLC using a YMC-Pack-Pro C18 column eluting with 0.1 M TEAB and acetonitrile. Compound 19 was obtained as triethylammonium salt. Yield: 116 µmol (38%). $^1$H NMR (400 MHz, D$_2$O): δ (ppm) 7.59 (s, 1H, 5-CH T), 6.14 (dd, J=5.5 Hz J=9.1 Hz, 1H, 1'-CH), 4.65 (m, 3'-CH), 4.13 (m, 1H, 4'-CH), 3.95 (m, 2H, 5'-CH$_2$), 3.72 (q, 2H, J=6.5 Hz, POCH$_2$), 3.63 (m, 2H, POCH$_2$), 2.95 (q, Et$_3$NH$^+$ counter ion), 2.71 (t, J=7.6 Hz, 2H, C$_{H2}$NH$_2$), 2.25 (dd, J=5.6, Hz J=13.6 Hz, 1H, 2'-CH$_a$), 2.12 (m, 1H, 2'-CH$_b$), 2.07 (t, J=2.6 Hz, 1H, CH hex), 1.96 (dt, J=2.3 Hz J=7.1 Hz, 2H, CH$_2$ hex), 1.71 (s, 3H, CH$_3$ T), 1.44-1.30 (m, 8H, CH$_2$ hex and CH$_2$C12), 1.10-0.98 (m, CH$_2$ hex and CH$_2$Cl$_2$ and Et$_3$NH$^+$ counter ion). $^{31}$P NMR (162 MHz, D$_2$O): δ (ppm) −0.65 (s, 1P, 3'P), −11.20 (d, J=19.3 Hz, 1P, $^γ$P), −12.94 (d, J=18.4 Hz, 1P, $^α$P), −23.35 (t, J=18.7 Hz, 1P, $^β$P). LC-MS (ES and CI): (negative ion) m/z 412 (M−2H$^+$), 825 (M−H$^+$); (positive ion) m/z 827 (M+Et$_3$NH$^+$).

1-(Black Hole Quencher 2)amido-3,6,9-trioxaundecan-11-azide (BHQ2-Peg3-N3) (20)

Black Hole Quencher 2 carboxylic acid (Biosearch Technologies, CA) (55 mg, 0.1 mmol) was dissolved in 5 mL of anhydrous DMF, and flushed with dry nitrogen gas. N,N-Diisopropylethylamine (DIPEA, 161 µL, 1 mmol), and N,N,N',N'-tetramethyl-O—(N-succinimidyl)uronium tetrafluoroborate (TSTU, 33 mg, 0.11 mmol) were added and the reaction was stirred at room temperature for 45 minutes. Then, 1-amino-3,6,9-trioxaundecan-11-azide (73 µL, 0.3 mmol) was added to it and the reaction was stirred at room temperature for 1.5 hours. The solvent was evaporated, the residue was dissolved in 50 mL of CH$_2$Cl$_2$ and extracted with 2×50 mL of water. The organic phase was dried over Na$_2$SO$_4$ anhydrous, and the solvent was removed under reduced pressure. The residue was purified, firstly by chromatography on silica gel eluting with a gradient of methanol in dichloromethane (0-2%), then by RP chromatography on C18, eluting with a gradient of acetonitrile in water (50% to 100%). Yield: 54 mg (76 µmols, 76%). R$_f$ (CH$_2$Cl$_2$/MeOH 95:5): 0.8. $^1$H NMR (400 MHz, CDCl$_3$): δ (ppm) 8.34 (d, J=9.0 Hz, 2H, CH—C—NO$_2$), 8.02 (d, J=9.0 Hz, 2H, CH—CH—C—NO$_2$), 7.90 (d, J=9.1 Hz, 2H, CH$_3$—N—CH—CH—N=N), 7.47 (s, 1H, N=N—C—CH—C—OCH$_3$), 7.43 (s, 1H, N=N—C—CH—C—OCH$_3$), 6.75 (d, J=8.8 Hz, 2H, CH$_3$—N—CH—CH—N=N), 6.08 (m, 1H, NH), 4.07 (s, 3H, OCH$_3$), 4.02 (s, 3H, OCH$_3$), 3.63 (m, 16H, O—CH$_2$—CH$_2$—O), 3.55-3.41 (m, 6H, NH—CH$_2$—CH$_2$—O, N3-CH$_2$—CH$_2$—O), 3.35 (m, 2H, CH$_2$—N—CH$_3$), 3.07 (s, 3H, N—CH$_3$), 2.19 (m, 2H, CH$_2$—CONH), 1.97-1.88 (m, 4H, CH$_2$—N$_3$ and CH$_2$—CH$_2$—CH$_2$). LC-MS (ES and CI): (positive ion) m/z 707 (M+H$^+$); (negative ion): 706 (M−). UV-VIS λ$_{max}$=553 nm (acetonitrile).

5'-(γ-(BHQ2-peg3)triphosphate) 3'-(O-(12-aminododecyl)phosphate)thymidine (BHQ2-pppT-3'PO$_4$C12NH$_2$) (21)

A solution of compound 19 (1.7 mL, 25 µmol) was placed in a 10 mL flask and BHQ2-peg3-N3 (20) (25 µmol), dissolved in 2 mL of tert-butanol, was added. The solution was then evaporated to dryness under reduced pressure, the residue was suspended in 500 µL of tert-butanol and stirred for 10 minutes. Then water (500 µL) and DMF (100 µL) were added. The catalyst solution was prepared by adding to a microcentrifuge tube, in the following order, sodium ascorbate (125 µL from a freshly prepared 100 mM stock in water, 12.5 µmol), tris[(1-benzyl-1H-1,2,3-triazol-4-yl)methyl]amine (TBTA, 250 µL from a freshly prepared 10 mM stock in DMF, 2.5 mmol), tert-butanol (250 µL), CuSO$_4$ (125 µL from a 10 mM stock in water, 1.25 µmol). The solution was let stand for two minutes and then added to the reaction mixture. The reaction was stirred at room temperature under nitrogen flow until no more starting materials were observed by RP-HPLC (C18). The solvent was evaporated under reduced pressure, the residue was resuspended in water, filtered and purified by preparative scale HPLC using a Waters X-Bridge C18 column eluting with 0.1 M TEAB and acetonitrile. Compound 21 was obtained as triethylammonium salt. Yield: 10.5 µmol (40%). LC-MS (ES and CI): (negative ion) m/z 765 (M−2H$^+$), 1530 (M−H$^+$). RP-HPLC t$_R$ (20%-60% acetonitrile gradient in 0.1M TEAB, 20 min, YMC-C18): 19.2 min. UV-VIS λ$_{max}$=574 nm (0.1 M TEAB aq.).

5'-(γ-(BHQ2-peg3)triphosphate) 3'-(O-(12-(Atto532) amidododecyl)phosphate)thymidine (BHQ2-pppT-3'PO$_4$C12 Atto532) (22)

Nucleotide 21 (2.7 mL, 3 µmol) was placed in a 5 mL flask and evaporated under reduced pressure to dryness. The residue was re-dissolved in 100 µL of 0.1 M TEAB aq. Atto532 N-hydroxysuccinimide ester (4.4 mg, 6 µmol) was dissolved in 1 mL of anhydrous DMF, N,N-Diisopropylethylamine (DIPEA, 4.8 µL, 30 µmol) was added and the solution was added to 21 via a syringe. The reaction was stirred at room temperature for 3.5 hours, screened from light. The flask was placed in a water-ice bath, quenched with 3 mL of 0.1 M TEAB aq. and stirred for 30 minutes. The mixture was filtered and purified by preparative scale HPLC using a YMC-Pack-Pro C18 column eluting with 0.1 M TEAB and acetonitrile. Compound 22 was obtained as triethylammonium salt. LC-MS (ES and CI): (negative ion) m/z 626 (M−4H$^+$), 835 (M−3H$^+$), 1253 (M−2H$^+$). RP-HPLC t$_R$ (20%-60% acetonitrile gradient in 0.1 M TEAB, 20 min, YMC-C18): 18.7 min. UV-VIS λmax=538 nm (10 mM Tris, pH 8.0). Fluorescence: λmax=550 nm (10 mM Tris, pH 8.0).

Example XII

Synthesis of a Quencher/Dye Labeled Nucleotide 5'-Pentaphosphate 3'-Phosphotriester This example describes synthesis of a quencher/dye labeled nucleotide 5'-pentaphosphate 3'-phosphotriester. A diagrammatic representation of the synthesis scheme is shown in FIG. 22.

5' triphosphate 3' (O-methyl, O'-(12-trifluoroacetylaminododecyl)phosphate)thymidine (pppT-3'PO$_4$(Me)(C12TFA)) (23)

The compound 5' triphosphate 3' (O-methyl, O'-(12-trifluoroacetylaminododecyl)phosphate)thymidine (23) was prepared from 5'-(4,4'-Dimethoxytrityl)thymidine 3'-[O-methyl-N,N-diisopropyl]-phosphoramidite (1.5 g, 2.12 mmol) as described for compounds 11, 12, and 13. Compound 23 was obtained as triethylammonium salt and as a mixture of two diastereoisomers. LC-MS (ES and CI): (negative ion) m/z 426 (M–2H$^+$), 854 (M–H$^+$). RP-HPLC t$_R$ (5%-50% acetonitrile gradient in 0.1 M TEAB, 20 min, YMC-C18): 20.3, 20.5 min.

5'-(ε-(1-hex-5-ynyl)pentaphosphate) 3' (O-methyl, O'-(12-trifluoroacetylaminododecyl)phosphate)thymidine (hex-pentaPT-3'PO$_4$(Me)(C12TFA) (24)

1-Hex-5-ynyl pyrophosphate tris(tri-n-butylammonium) salt, 0.5 M in DMF (17) (1 mL, 0.5 mmol) was placed in a round bottomed flask. The solution was stirred under reduced pressure from an oil pump for 10 minutes to remove any water present. The flask was purged with N$_2$, then anhydrous DMF (1 mL) and 1,1'-carbonyldiimidazole (202 mg, 1.25 mmol) were added. The reaction was stirred for 2 hours at room temperature, then quenched with methanol (0.5 mL) and stirred further for 1.5 hours. In the meantime, a solution of 5' triphosphate 3' (O-methyl, O'-(12-trifluoroacetylaminododecyl) phosphate) thymidine (23) (19.6 mL, 0.1 mmol) was placed in a flask and evaporated under reduced pressure to dryness. The residue was then co-evaporated with 2 mL of anhydrous DMF. The pyrophosphate reaction was then quickly evaporated under reduced pressure to remove the methanol, then added to the stirring nucleotide residue, under N$_2$. ZnCl$_2$ (136 mg, 1 mmol), previously dried at 100° C. for 4 hours, was quickly added to the reaction. The salt dissolved after 10 minutes, and the mixture was stirred at room temperature for 24 hours. The solution was diluted with 5 mL of 0.1 M TEAB aq. and a precipitate formed immediately. The suspension was stirred at room temperature for 30 minutes, then the precipitate was removed by filtration on a synthered glass funnel. The filtrate was diluted with water (20 mL) and partially purified by ion-exchange chromatography on DEAE-Sephadex A25 (25 g). The column was eluted with a linear gradient of aqueous triethylammonium bicarbonate (from 0.05 M to 1 M over 600 mL). Yield: 50 µmol (50%). LC-MS (ES and CI): (negative ion) m/z 546 (M–2H$^+$), 1093 (M–H$^+$). RP-HPLC t$_R$ (25%-40% acetonitrile gradient in 0.1 M TEAB, 20 min, YMC-C18): 19.3, 19.7 min.

5'-(ε-(1-hex-5-ynyl)pentaphosphate) 3'(O-methyl, O'-(12-aminododecyl)phosphate)thymidine (hex-pentaPT-3'PO$_4$(Me)(C12NH2)) (25)

5'-(ε-(1-hex-5-ynyl)pentaphosphate) 3' (O-methyl, O'-(12-trifluoroacetylaminododecyl) phosphate) thymidine (24) (50 µmol, in TEAB aq.) was placed in a flask and evaporated to dryness. The residue was co-evaporated with 2×20 mL of water, then dissolved in 10 mL of freshly prepared 0.25 M K$_2$CO$_3$ in methanol/water 8:2. A precipitate formed immediately and the mixture was stirred vigorously for 18 hours at room temperature, then quenched with 0.5 M TEAB aq. The crude mixture was evaporated under reduced pressure, the residue resuspended in water and purified by preparative scale HPLC using a YMC-Pack-Pro C18 column eluting with 0.1 M TEAB and acetonitrile. Compound 25 was obtained as triethylammonium salt. Yield: 27 µmol (55%). LC-MS (ES and CI): (negative ion) m/z 332 (M–3H$^+$), 498 (M–2H$^+$), 998 (M–H$^+$). $^1$H NMR (400 MHz, D$_2$O): δ (ppm) 7.61 (s, 1H, 5-CH T), 6.32 (m, 1H, 1'-CH), 5.12 (m, 3'-CH), 4.33 (m, 1H, 4'-CH), 4.09 (m, 2H, 5'-CH$_2$ and POCH$_2$), 3.88 (q, 2H, J=6.5 Hz, POCH$_2$), 3.74, 3.73 (two d, J=11.3 Hz, 3H, POCH$_3$ two diast.), 2.98 (q, Et$_3$NH+ counter ion), 2.80 (t, J=7.4 Hz, 2H, CH$_2$NH$_2$), 2.42 (dd, J=5.1, Hz J=14.4 Hz, 1H, 2'-CH$_a$), 2.30 (m, 1H, 2'-CH$_b$), 2.20 (t, J=2.7 Hz, 1H, CH hex), 2.13 (dt, J=2.1, Hz J=9.2 Hz, 2H, CH$_2$ hex), 1.79 (s, 3H, CH$_3$ T), 1.64-1.45 (m, 8H, CH$_2$ hex and CH$_2$Cl$_2$), 1.29-0.78 (m, CH$_2$ hex and CH$_2$Cl$_2$ and Et$_3$NH$^+$ counter ion). $^{31}$P NMR (162 MHz, D$_2$O): δ (ppm) –1.00 (two s, 1P, 3'P two diast.), –10.96 (d, J=17.6 Hz, 1P, $^\epsilon$P), –11.98 (d, J=16.8 Hz, 1P, $^\alpha$P), –23.33 (m, 3P, $^\beta$P, $^\gamma$P, $^\delta$P). RP-HPLC t$_R$ (5%-40% acetonitrile gradient in 0.1M TEAB, 20 min, YMC-C18): 19.6, 19.8 min.

5'-(ε-(BHQ2-Peg3) pentaphosphate) 3' (O-methyl, O'-(12-aminododecyl)phosphate)thymidine (BHQ2-pentaPT-3'PO$_4$(Me)(C12NH2)) (26)

Compound 26 was synthesised from compound 25 (25 µmol) and BHQ2-peg3-N3 (20) (19 mg, 27 µmol) as described for compound 21. Yield: 22 µmol (89%). LC-MS (ES and CI): (negative ion) m/z 425 (M–4H$^+$), 567 (M–3H$^+$), 852 (M–2H$^+$), 1705 (M–H$^+$). RP-HPLC t$_R$ (30%-60% acetonitrile gradient in 0.1M TEAB, 20 min, YMC-C18): 17.6 min. UV-VIS λmax=575 nm (10 mM Tris, pH 8.0).

5'-(ε-(BHQ2-Peg3) pentaphosphate) 3' (O-methyl, O'-(12-(SJM643)amidododecyl)phosphate)thymidine (BHQ2-pentaPT-3'PO$_4$(Me)(C12-SJM643)) (27)

The fluorescent dye SJM643 carboxylate (3.8 mg, 6 µmol) was added to a 10 mL round bottomed flask and coevaporated twice with 1 mL of anhydrous DMF. Then, the flask was placed under N$_2$ flow and the solid residue was dissolved in 1 mL of anhydrous DMF. N,N-Diisopropylethylamine (DIPEA, 4.8 µL, 30 µmol), and N,N,N',N'-tetramethyl-O—(N-succinimidyl)uronium tetrafluoroborate (TSTU, 66 µL of 100 mM solution in dry DMF, 6.6 µmol) were added and the reaction was stirred at room temperature for 1 hour. In the meantime, nucleotide 21 (1.25 mL, 3 µmol) was placed in a 10 mL flask and evaporated under reduced pressure to dryness. The residue was re-dissolved in 100 µL of 0.1 M TEAB aq., then the solution of SJM643-N-hydroxysuccinimide ester was added to it via a syringe. The reaction was stirred at room temperature for 3 hours, screened from direct light. The flask was placed in a water-ice bath, quenched with 3 mL of 0.1 M TEAB aq. and stirred for 30 minutes. The mixture was filtered and purified by preparative scale HPLC using a YMC-Pack-Pro C18 column eluting with 0.1 M TEAB and acetonitrile. LC-MS (ES and CI): (negative ion) m/z 775 (M–3H$^+$), 1163 (M–2H$^+$).

RP-HPLC $t_R$ (30%-60% acetonitrile gradient in 0.1M TEAB, 20 min, YMC-C18): 18.1 min. UV-VIS $\lambda_{max}$=640 nm (10 mM Tris, pH 8.0), 581 nm (acetonitrile/Tris pH 8 9:1). Fluorescence: $\lambda_{max}$=662 nm (10 mM Tris, pH 8.0).

Example XIII

Fluorescence Properties of a Quencher/Dye Labeled Nucleotide (22)

The fluorescence emission of an approx. 4 µM solution of the quencher/dye labelled nucleotide 22, a 4 µM solution of Atto532 dye and an equimolar mixture of Atto532 dye and quencher labelled nucleotide 21 (4 µM) were measured in 10 mM Tris buffer pH 8.0, between 500 nm and 700 nm (excitation wavelength: 532 nm) (FIG. 23). The fluorescence of the nucleotide 22 was approximately 1500-fold lower than that of the free dye in solution, and approximately 1100-fold lower than the equimolar solution of the free dye and the quencher labelled nucleotide 21. This indicates that, when a nucleotide is labeled with both the Atto532 dye and the BlackHole Quencher 2 (BHQ2), the fluorescence emission is quenched by the BHQ2 very effectively (>99%). However, when the dye and the quencher are not both linked to the nucleotide, BHQ2 does not quench efficiently, resulting in a fluorescence level comparable to that of the free dye.

Throughout this application various publications, patents and patent applications have been referenced. The disclosures of these publications in their entireties are hereby incorporated by reference in this application.

The term "comprising" is intended herein to be open-ended, including not only the recited elements, but further encompassing any additional elements.

A number of embodiments have been described. Nevertheless, it will be understood that various modifications may be made. Accordingly, other embodiments are within the scope of the following claims.

What is claimed is:

1. A method of synthesizing a polynucleotide, comprising
   (a) providing a mixture comprising a nucleic acid, a collection of different nucleotide analogs, a polymerase having activity to incorporate a nucleotide analog comprising a blocking moiety into a nucleic acid, and a deblocking agent having activity to selectively remove a blocking moiety that has been incorporated into a nucleic acid compared to a blocking moiety attached to a monomeric nucleotide analog, wherein each different nucleotide analog comprises a blocking moiety, and
   (b) allowing sequential addition of a plurality of the different nucleotide analogs to the nucleic acid to proceed via several reaction cycles in the mixture, wherein the polymerase and the deblocking agent are simultaneously present in the mixture to carry out the reaction cycles,
   wherein each reaction cycle comprises:
      (i) the polymerase adding a nucleotide analog from the collection of different nucleotide analogs to the nucleic acid to form a transient nucleic acid species comprising the blocking moiety, and
      (ii) the deblocking agent modifying the transient nucleic acid species to remove the blocking moiety;
   wherein the blocking moiety is attached to the nucleotide analog at a 3' carbon of a pentose moiety of the nucleotide analog, and the blocking moiety comprises a phosphodiester moiety or a phosphotriester moiety.

2. The method of claim 1, wherein the blocking moiety further comprises a label moiety.

3. The method of claim 2, further comprising detecting the label in the mixture during each reaction cycle.

4. The method of claim 3, further comprising determining the sequence of the nucleic acid from a sequence of labels detected during the several reaction cycles.

5. The method of claim 2, wherein the different nucleotide analogs comprise different base moieties and different label moieties, individual label moieties of the different label moieties being correlated with a specific base moiety.

6. The method of claim 2, wherein the different nucleotide analogs further comprise a label-modifier moiety.

7. The method of claim 6, wherein the label moiety comprises a fluorophore and the label-modifier moiety comprises a quencher of the fluorophore, a FRET donor to the fluorophore or a FRET acceptor to the fluorophore.

8. The method of claim 6, further comprising detecting a signal from the label in the absence of the label-modifier moiety during each reaction cycle.

9. The method of claim 6, wherein each reaction cycle further comprises the polymerase removing the label-modifier moiety from the nucleotide analog.

10. The method of claim 6, wherein the nucleotide analog comprises a triphosphate moiety and wherein the label-modifier moiety is attached to the triphosphate moiety.

11. The method of claim 1, wherein the deblocking agent comprises a phosphoesterase enzyme.

12. The method of claim 1, wherein the phosphoesterase selectively removes the phosphodiester moiety or the phosphotriester moiety from the transient nucleic acid species.

13. The method of claim 1, wherein the phosphoesterase is selected from the group consisting of Endonuclease IV and AP endonuclease.

14. The method of claim 1, wherein the nucleic acid is one of a plurality of different nucleic acids in the mixture, wherein the plurality of the different nucleotides analogs are sequentially added to several of the different nucleic acids in the mixture by several reaction cycles in the mixture, wherein each reaction cycle comprises the polymerase adding nucleotide analogs to the several different nucleic acids to form several transient nucleic acid species comprising a blocking moiety and the deblocking agent modifies the several transient nucleic acid species to remove the blocking moiety.

15. The method of claim 14, wherein the several different nucleic acids in the mixture are attached to a solid-phase support.

16. The method of claim 14, wherein the blocking moiety of the several transient nucleic acid species further comprises a label moiety.

17. The method of claim 16, further comprising detecting the label during each reaction cycle.

18. The method of claim 17, wherein individual nucleic acids of the several different nucleic acids are individually resolved on the solid-phase support by the detecting.

19. The method of claim 17, wherein nucleic acids of the several different nucleic acids are detected as features on the solid-phase support during the detecting, wherein individual features comprise several copies having the same nucleic acid sequence.

20. The method of claim 14, wherein the several different nucleic acids comprise at least 1,000 different nucleic acid sequences.

21. The method of claim 1, wherein the transient nucleic acid species is present for at least 1 millisecond before the deblocking agent modifies the transient nucleic acid species to remove the blocking moiety.

22. The method of claim 21, wherein the transient nucleic acid species is present for no more than 30 seconds before the deblocking agent modifies the transient nucleic acid species to remove the blocking moiety.

23. The method of claim 1, wherein the several reaction cycles comprises at least 100 reaction cycles, whereby the nucleic acid is extended by addition of at least 100 nucleotide analogs.

24. The method of claim 23, further comprising adding any one of a nucleotide analog, a polymerase or a deblocking agent to the mixture after the first reaction cycle is complete and before the last reaction cycle is complete.

25. A method of synthesizing a polynucleotide, comprising
(a) providing a mixture comprising a nucleic acid, a collection of different nucleotide analogs, a polymerase having activity to incorporate a nucleotide analog comprising a blocking moiety into a nucleic acid, a phosphotriesterase and a phosphodiesterase, wherein the phosphotriesterase and the phosphodiesterase together have activity to selectively remove a blocking moiety that has been incorporated into a nucleic acid compared to a blocking moiety attached to a monomeric nucleotide analog,
wherein the different nucleotide analogs each comprise a phosphotriester blocking moiety, and
(b) sequentially adding a plurality of the different nucleotide analogs to the nucleic acid by several reaction cycles in the mixture, wherein the polymerase, phosphotriesterase and phosphodiesterase are simultaneously present in the mixture to carry out the reaction cycles,
wherein each reaction cycle comprises:
(i) the polymerase adding a nucleotide analog of the collection of different nucleotide analogs to the nucleic acid to form a transient nucleic acid species comprising the phosphotriester blocking moiety,
(ii) the phosphotriesterase converting the phosphotriester blocking moiety to a phosphodiester blocking moiety, and
(iii) the phosphodiesterase removing the phosphodiester blocking moiety from the nucleic acid.

26. The method of claim 25, wherein the phosphotriester blocking moiety further comprises a label moiety.

27. The method of claim 26, further comprising detecting the label in the mixture during each reaction cycle.

28. The method of claim 27, further comprising determining the sequence of the nucleic acid from a sequence of labels detected during the several reaction cycles.

29. The method of claim 26, wherein the different nucleotide analogs further comprise a label-modifier moiety.

30. The method of claim 29, further comprising detecting a signal from the label in the absence of the label-modifier moiety during each reaction cycle.

31. The method of claim 29, wherein each reaction cycle further comprises the polymerase removing the label-modifier moiety from the nucleotide analog.

32. The method of claim 25, wherein the nucleic acid is one of a plurality of different nucleic acids in the mixture, wherein the plurality of the different nucleotide analogs are sequentially added to several of the different nucleic acids in the mixture by several reaction cycles in the mixture, wherein each reaction cycle comprises the polymerase adding nucleotide analogs to the several different nucleic acids to form several transient nucleic acid species comprising a phosphotriester blocking moiety, the phosphodiesterase converts the phosphotriester blocking moiety on the several transient nucleic acid species to a phosphodiester blocking moiety and the phosphodiesterase removes the phosphodiester blocking moiety from the several transient nucleic acid species.

33. The method of claim 32, wherein the several different nucleic acids in the mixture are attached to a solid-phase support.

34. The method of claim 32, wherein the phosphotriester blocking moiety of the several transient nucleic acid species further comprises a label moiety.

35. The method of claim 34, further comprising detecting the label during each reaction cycle.

36. The method of claim 35, wherein individual nucleic acids of the several different nucleic acids are individually resolved on the solid-phase support by the detecting.

37. The method of claim 25, wherein, the several reaction cycles comprise a single pot reaction.

38. The method of claim 25, wherein the several reaction cycles comprise a single pot reaction.

* * * * *

UNITED STATES PATENT AND TRADEMARK OFFICE
CERTIFICATE OF CORRECTION

PATENT NO. : 10,378,051 B2
APPLICATION NO. : 13/627134
DATED : August 13, 2019
INVENTOR(S) : Wouter Meuleman et al.

It is certified that error appears in the above-identified patent and that said Letters Patent is hereby corrected as shown below:

In the Drawings

In sheet 23 of 24, in FIG. 23, X-axis, delete "wavelenght" and insert -- wavelength --, therefor.

In the Specification

In Column 6, Line 39, delete "tri(hydroxylpropyl)phosphine" and insert
-- tris(hydroxypropyl)phosphine --, therefor.

In Column 15, Line 63, delete "I" and insert -- 1 --, therefor.

In Column 17, Line 20, delete "No." and insert -- Nos. --, therefor.

In Column 20, Line 15 (approx.), delete "Malacite green," and insert -- Malachite green, --, therefor.

In Column 20, Line 17 (approx.), delete "phycoerythin," and insert -- phycoerythrin, --, therefor.

In Column 22, Line 36, delete "Freemont," and insert -- Fremont, --, therefor.

In Column 25, Line 53, delete "and or" and insert -- and/or --, therefor.

In Column 26, Line 9, after "in" delete "on".

In Column 43, Line 38, delete "tri(hydroxylpropyl)phosphine" and insert
-- tris(hydroxypropyl)phosphine --, therefor.

In Column 44, Line 62, delete "15 µg/mlpolymerase" and insert -- 15 µg/ml polymerase --, therefor.

In Column 45, Line 9, delete "hexynyl-pppT3'PO$_4$Me2" and insert -- hexynyl-pppT3'PO$_4$Me$_2$ --, therefor.

Signed and Sealed this
Seventeenth Day of December, 2019

Andrei Iancu
*Director of the United States Patent and Trademark Office*

In Column 45, Lines 43-44, delete "5'(4,4'-dimethoxytrityl)-3'" and insert -- 5'-(4,4'-dimethoxytrityl)-3' --, therefor.

In Column 45, Line 54, delete "CH—" and insert -- $CH_b$- --, therefor.

In Column 46, Line 26, delete "mmol)" and insert -- mmol), --, therefor.

In Column 46, Line 61, delete "(q, $Et_3NH'$ counter ion)," and insert -- (q, $Et_3NH^+$ counter ion), --, therefor.

In Column 46, Line 63, delete "(t, $Et_3NH'$ counter ion)," and insert -- (t, $Et_3NH^+$ counter ion), --, therefor.

In Column 47, Line 40, delete "(br, $Et_3NH'$ counter" and insert -- (br, $Et_3NH^+$ counter --, therefor.

In Column 48, Line 32, delete "OCH2O)," and insert -- $OCH_2O$), --, therefor.

In Column 48, Line 33, delete "POCH2-Ar)," and insert -- $POCH_2$-Ar), --, therefor.

In Column 49, Line 48, delete "(q, $ET_3NH'$ counter ion)," and insert -- (q, $Et_3NH^+$ counter ion), --, therefor.

In Column 50, Line 21, delete "$_\alpha P$)," and insert -- $^\alpha P$), --, therefor.

In Column 51, Line 1, delete "CH2" and insert -- $CH_2$ --, therefor.

In Column 52, Lines 29-30, delete "(q, $ET_3NH'$ counter ion)," and insert -- (q, $Et_3NH^+$ counter ion), --, therefor.

In Column 52, Line 55, delete "pppT3' phosphate" and insert -- pppT3'phosphate --, therefor.

In Column 54, Line 36, delete "D2O):" and insert -- $D_2O$): --, therefor.

In Column 55, Line 34, delete "$C_{H2}NH_2$)," and insert -- $CH_2NH_2$), --, therefor.

In Column 56, Line 29, delete "2.5 mmol)," and insert -- 2.5 µmol), --, therefor.

In Column 57, Line 52, delete "synthered" and insert -- sintered --, therefor.

In Column 58, Line 17, delete "NH+" and insert -- $NH^+$ --, therefor.

In the Claims

In Column 60, Line 59, in Claim 12, delete "claim 1," and insert -- claim 11, --, therefor.

CERTIFICATE OF CORRECTION (continued)
U.S. Pat. No. 10,378,051 B2

In Column 60, Line 62, in Claim 13, delete "claim 1," and insert -- claim 11, --, therefor.

In Column 62, Line 56, in Claim 37, delete "wherein," and insert -- wherein --, therefor.